(12) United States Patent
Czaja et al.

(10) Patent No.: US 11,596,832 B2
(45) Date of Patent: Mar. 7, 2023

(54) METHOD AND APPARATUS FOR EARLY DETECTION OF DIABETIC FOOT DISORDERS BY ANALYZING FOOT TEMPERATURE AND VERTICAL AND SHEAR FORCES ON FEET

(71) Applicant: IPComm LLC, Cardiff, CA (US)

(72) Inventors: Stanislaw Czaja, Cardiff, CA (US); Lora O'Leary, Cardiff, CA (US)

(73) Assignee: IPCOMM LLC, Cardiff, CA (US)

( * ) Notice: Subject to any disclaimer, the term of this patent is extended or adjusted under 35 U.S.C. 154(b) by 272 days.

(21) Appl. No.: 17/086,163

(22) Filed: Oct. 30, 2020

(65) Prior Publication Data

US 2021/0046356 A1 Feb. 18, 2021

Related U.S. Application Data

(63) Continuation-in-part of application No. 16/897,163, filed on Jun. 9, 2020, which is a continuation of
(Continued)

(51) Int. Cl.
*A41D 1/00* (2018.01)
*A43B 3/00* (2022.01)
(Continued)

(52) U.S. Cl.
CPC ............ *A63B 24/0006* (2013.01); *A43B 3/34* (2022.01); *A43B 5/00* (2013.01); *A43B 5/04* (2013.01); *A43B 5/0405* (2013.01); *A43B 5/16* (2013.01); *A43B 5/1616* (2013.01); *A43B 17/00* (2013.01); *A61B 5/1124* (2013.01); *A61B 5/6807* (2013.01); *A63B 71/0622* (2013.01); *A63C 3/00* (2013.01); *A63C 11/003* (2013.01);
(Continued)

(58) Field of Classification Search
CPC ..... A61B 5/002; A61B 5/0022; A61B 5/0024; A61B 5/4029; A61B 5/4047; A61B 5/6807; A61B 5/721; A61B 5/7275; A61B 5/7264; A61B 5/7282; A61B 5/746; A43B 3/34
See application file for complete search history.

(56) References Cited

U.S. PATENT DOCUMENTS

2009/0082694 A1* 3/2009 Poisner ............... A61B 5/4827
  600/555
2016/0335913 A1* 11/2016 Grant ...................... B32B 5/26

FOREIGN PATENT DOCUMENTS

WO  WO-2016142442 A1 * 9/2016 ............. A41D 1/002

* cited by examiner

Primary Examiner — Lawrence S Galka

(57) ABSTRACT

A system for analysis of user gait and foot disorder intended to minimize risks ulceration and limb amputation associated with the uncontrolled increase of the foot temperature in persons with diabetes. This system comprises a motion, force and temperature sensors and a processing element configured to process motion algorithms, measure ground reaction force (GRF) and changes in foot temperature embedded in the footwear insoles in communication with a smartphone based analysis application using wireless radio interface. The analysis application processes data received from the footwear sensors, compares the results with set of criteria and rules, and if any of the predefined criteria is exceeded, provides alerts to the user and the remote medical supervisor. Additionally, the insoles may be equipped with a haptic actuators configured to determine the level of the user neuropathy by measuring vibration perception threshold (VPT) level.

21 Claims, 31 Drawing Sheets

Related U.S. Application Data application No. 15/464,083, filed on Mar. 20, 2017, now abandoned, which is a continuation-in-part of application No. 14/747,179, filed on Jun. 23, 2015, now Pat. No. 9,968,840.

(51) Int. Cl.

| | |
|---|---|
| *A61B 5/01* | (2006.01) |
| *A63B 24/00* | (2006.01) |
| *A43B 5/00* | (2022.01) |
| *A63B 71/06* | (2006.01) |
| *A43B 5/04* | (2006.01) |
| *G09B 5/02* | (2006.01) |
| *G09B 19/00* | (2006.01) |
| *A43B 5/16* | (2006.01) |
| *A63C 11/00* | (2006.01) |
| *G06F 3/01* | (2006.01) |
| *A61B 5/11* | (2006.01) |
| *A61B 5/00* | (2006.01) |
| *A63C 3/00* | (2006.01) |
| *G16H 20/30* | (2018.01) |
| *G16H 40/63* | (2018.01) |
| *G16H 40/67* | (2018.01) |
| *A43B 17/00* | (2006.01) |
| *A43B 3/34* | (2022.01) |
| *G06V 40/20* | (2022.01) |
| *G01S 19/19* | (2010.01) |
| *A63B 69/18* | (2006.01) |
| *H04M 1/72412* | (2021.01) |

(52) U.S. Cl.
CPC .............. *G06F 3/011* (2013.01); *G06F 3/016* (2013.01); *G06V 40/25* (2022.01); *G09B 5/02* (2013.01); *G09B 19/0038* (2013.01); *G16H 20/30* (2018.01); *G16H 40/63* (2018.01); *G16H 40/67* (2018.01); *A61B 5/0024* (2013.01); *A61B 5/7225* (2013.01); *A61B 2503/10* (2013.01); *A61B 2505/09* (2013.01); *A61B 2562/0219* (2013.01); *A61B 2562/0247* (2013.01); *A63B 69/18* (2013.01); *A63B 2071/0636* (2013.01); *A63B 2071/0655* (2013.01); *A63B 2220/12* (2013.01); *A63B 2220/16* (2013.01); *A63B 2220/36* (2013.01); *A63B 2220/40* (2013.01); *A63B 2220/44* (2013.01); *A63B 2220/56* (2013.01); *A63B 2220/62* (2013.01); *A63B 2220/74* (2013.01); *A63B 2220/803* (2013.01); *A63B 2220/836* (2013.01); *A63B 2220/89* (2013.01); *A63B 2225/02* (2013.01); *A63B 2225/20* (2013.01); *A63B 2225/50* (2013.01); *A63B 2225/54* (2013.01); *A63B 2244/19* (2013.01); *A63C 2203/12* (2013.01); *A63C 2203/18* (2013.01); *A63C 2203/22* (2013.01); *A63C 2203/24* (2013.01); *G01S 19/19* (2013.01); *H04M 1/72412* (2021.01)

METHOD AND APPARATUS FOR EARLY DETECTION OF DIABETIC FOOT DISORDERS BY ANALYZING FOOT TEMPERATURE AND VERTICAL AND SHEAR FORCES ON FEET

CROSS REFERENCE TO RELATED APPLICATIONS—CLAIMS OF PRIORITY

This application is a continuation-in-part (CIP) of co-pending U.S. application Ser. No. 16/897,163 filed Jun. 9, 2020, entitled "METHOD AND APPARATUS FOR ANALYSIS OF GAIT AND TO PROVIDE HAPTIC AND VISUAL CORRECTIVE FEEDBACK"; and application Ser. No. 16/897,163 is a continuation of U.S. application Ser. No. 15/464,083 filed Mar. 20, 2017, abandoned; and U.S. application Ser. No. 15/464,083 is a continuation-in-part (CIP) of U.S. application Ser. No. 14/747,179, filed Jun. 23, 2015, entitled "METHOD AND APPARATUS TO PROVIDE HAPTIC AND VISUAL FEEDBACK OF SKIER FOOT MOTION AND FORCES TRANSMITTED TO THE SKI BOOT"; and application Ser. No. 14/747,179 issued as U.S. Pat. No. 9,968,840 on May 15, 2018; and the contents of the co-pending application, published applications, and issued patent cited above are incorporated by reference herein as if set forth in full.

BACKGROUND

(1) Technical Field

The present invention relates to the field of providing visualization and analysis of motion, vertical and horizontal (shear) ground reaction force (GRF) transferred to users' feet as result of activity (run, walk, skiing) and recorded by various sensors located in a shoe insole or a user's shoe. Such invention may be used for the purpose of monitoring forces projected through the foot to the ski or snowboard to the snow or an athlete shoe to aid in training and performance evaluation, or to allow analysis or user gait, or as an aid to improve performance; recovery after physical injuries, or early detection of abnormal conditions of the foot temperature to prevent ulcers in persons having diabetes. This analysis is achieved in part by embedding a gyroscope, accelerometer, magnetometer, pressure, force and temperature sensors into the insole (or sole of a user's shoe) to provide measurement of foot rotational and lateral motions and temperature, in relation to GRF transmitted to the foot. Furthermore, when one or more actuators are embedded in the shoe insole a haptic corrective feedback may be provided directly to the user's foot. Foot motion vectors, location and distribution of GRF, vectors and temperature measurements are sampled at specific intervals by a micro-controller embedded in the insole, and transmitted to the user's smartphone using Bluetooth, or other suitable short range radio interface for analysis. Results of said analysis are synchronized to GPS time and coordinates, a difference between optimal distribution of force and the recorded distribution of force is applied to an appropriate filter, then transmitted as a stimulus signal to one or more actuators embedded in the shoe insole, to provide haptic feedback to the user, indicating timing and location of force distribution required to perform a best turn or to correct running or walking patterns. Those results may also be transmitted to a remote location (via a "cloud service", for example) for post-processing using the user's smartphone cellular radio interface. The post-processing may include, for example, presentation of the foot motion and force distribution in a form of animation, superimposition of motion and force data on the 3D maps obtained from GPS coordinates, etc. The post-processed visual and numeric data may then be received from the cloud server by the user's smartphone or by a remote computer terminal. Furthermore, in some embodiments, deviation between current data and normal data due for example to an: an accident; a fall (without recovery over certain period of time is detected), could cause, an emergency SMS message containing relevant to be sent to the predefined recipients.

(2) Background

Skiing monitoring of progress relies on a few simple techniques, such as, for example: user feelings, instructor/coach observations and feedback, etc, and some empirical factors, such as: time measurements and video analysis. However, most of those techniques are not practical for the everyday training or diagnostics and recovery of physical injuries, as they cannot provide a real-time feedback, or require bulky equipment, large team of highly skilled technicians while lacking sufficient amount of data.

In analysis of gait or during convalescence after injuries, the monitoring relies on visual observation of the foot profile, type of walk, or a scan of the user's foot. In some laboratory cases measurements of a user's foot on a force plate with or without synchronization of a video is used during gait analysis. While some of those techniques are widely used for selection an appropriate insole intended to support natural pronation, and other to provide detailed analysis of the foot motion/force relation during a stride, none can provide long term observation in outside environment or provide real time corrective feedback.

A similar situation exists in monitoring of foot disorders used for purposes of early detection of ulcers in people having diabetes. While numerous studies indicate that regular monitoring of foot temperature may limit the incidence of disabling conditions such as foot ulcers and lower limb amputation in people with diabetes, there is only a handful of tools—such as simple visual observation and periodic measurements of foot temperature, to performing a scan of the foot temperature using thermometry and crystal thermography. While the first two techniques are not convenient and not accurate, the second two while providing timely information—if performed twice a day every day, they are still inconvenient and require bulky and expensive scanners and a deep understanding of correlation between color maps and actual temperatures.

The comfort, safety and pleasure of skiing or running or the recovery period of motion skills, or early detection of foot abnormality are highly dependent on the amount of available accurate data; the quality of said data analysis; and if corrective feedback is employed, on it's the efficiency. While most athletes depend on advice from a coach, most recreational athletes relay solely of self-observation. Similarly, to analyze gait of an athlete, or individuals recovering from serious injuries, trained therapists must obtain data in a controlled laboratory environment employing video or infrared cameras placed around a walkway and/or a pressure plate or walkway comprising of force sensors. Data is collected, analyzed by professionals who provide feedback to the subject and/or therapist. To measure kinetics—ground reaction forces, laboratories may have floor-mounted load transducers, or pressure walkway with embedded pressure sensors, or stationary thermography equipment. Due to the complexity of such measurement systems, collected data rarely correlates with normal activity of the subject and the feedback to the subject and/or therapist is delayed.

In the past, innovation in recording of GRF t applied to the foot point of contacts were introduced in an attempt to analyze bio-mechanics of training and gait. However, those devices can only record distribution of forces—to correlate such distribution of forces with foot motion, the recorded forces require synchronization with real-time video of a subject. Because real-time video synchronization is rarely available outside of a laboratory environment, the benefit of such devices is very limited in real world use. An even more difficult challenge is to detect and prevent ulcers in persons with diabetes as most of the currently available methods rely on visits to a doctor's office, or at best, measuring foot temperature once or twice a day using a simple thermometer or a stationary thermography equipment. While foot disease is prevalent in persons with diabetics and frequently results in amputation of the person's foot, no simple non-invasive tools exist that permit real-time monitoring of the conditions leading to foot ulcers.

In recent years, the use of mobile devices and, in particular, smartphones proliferated, all provided by the progress in electronics circuit integration. Today's smartphones are equipped with various input/output capabilities, such as wireless PAN (Personal Area Network), and provide significant computing resources in addition to their capabilities of providing communication over cellular network. As the present disclosure teaches, such computing and communication resources may be integrated with a motion, force and temperature sensor embedded into replaceable sole of a ski boot, or a walking/running shoe, or a skate boot, etc. In such systems, data from sensors are analyzed by the smartphone based application. Results of said analysis may be presented in visual form on the smartphone user interface (UI), sent to a remote location, such as a doctor's office or coach for further analysis or to provide real-time corrective feedback. Such systems are suitable for an athlete trying to improve the athlete's performance. As described in greater detail below, such systems are also suitable for a patient trying to recover form an injury, or for persons with diabetes. In some embodiments of such a system and in accordance with the present disclosure, motion and force temperature sensors are embedded in the insole and are sampled at a specific interval. In these embodiments, the motion and force vectors and temperature measurements are transferred to the user smartphone or a dedicated cellular interface modem using Bluetooth or other suitable PAN radio interface. In these embodiments, as set forth in the detailed description below, the smartphone based application processes and analyzes the received samples, provides visualization of motion in relation to the ground reaction forces transferred to the user foot and provides corrective feedback to the user and appropriate alarms. In some embodiments as detailed below, the data from various sensors, or the results of analysis may be transmitted to a remote location using smartphone cellular radio interface for storage or post-processing in the "Internet cloud". Such system embodiments can be used as an aid in instruction or in recovery, or in prevention of injuries, or as a tool in objective determination of athlete performance—i. e. to determine a quality of performance by the free-style skier for example. Such systems may operate using any of wireless technologies available in a smartphone, such as: cdma2000, UMTS, WiMax, LTE. LTE-A, Bluetooth, ZigBee, etc.

Therefore, a need exists for methods and apparatus which allows visualization and analysis of a user's foot motion in relation to the magnitude and distribution of GRF and a temperature at the foot points-of-contact and providing real-time corrective haptic feedback to the user's foot. The presently disclosed inventions provide such methods and apparatus.

SUMMARY

The present disclosure describes a system which allows visualization and analysis of a user's foot motion in relation to the magnitude and distribution of GRF and a temperature at the foot points of contacts and to provide real-time corrective haptic feedback to the user's foot. In some embodiments, the system comprises several miniature micro-mechanical systems (MEMS) sensors and components embedded into the inner sole of the shoe such as: a 3-axis accelerometer sensor, a 3-axis gyroscope sensor, a 3-axis magnetometer sensor, and a multiplicity of thin-film force/pressure and temperature sensors. The accelerometer, gyroscope and magnetometer sensors provide motion vectors in 9-degree of freedom, allowing 3-D motion of the user's foot to be obtained. A plurality of force sensors provide measurement of vertical GRF, and a plurality of temperature sensors record the temperature of a user's foot. In addition, in some embodiments, an atmospheric pressure sensor may be provided that measures changes of atmospheric pressure. This allows recording of elevation. In some embodiments, the system provides measurement of linear acceleration, rotational vectors and orientation (attitude) in three-dimensional space to provide representation of the foot motion in relation to ground reaction forces. The recordings of motion and force vectors, synchronized with GPS time and coordinates, are transmitted to a smartphone based application for analysis, storage and to compute a corrective response which is send back to the haptic actuator(s) embedded in the insoles. Such corrective feedback response is based on the past and current motion and force vectors, and difference between biomechanical model of activity and kinematics of current user motion and intended to provide information on time and the location the center of pressure (COP) must be located during a next turn or phase of the gait. The results of this analysis may also be communicated to a remote location for post-processing and presentation in visual and numerical form. Such presentation may be used to understand the precise cause of errors—in the time/position of the COP, to aid in training, or to provide explanation of the nature of the errors and to suggest a remedy or remedies. The corrective stimulus may take the form of a haptic feedback provided by an actuator located under the user's toe(s) instructing regarding the time and location of the COP. In addition, topological information in the form of map generated from recorded GPS coordinates is added to visual presentation of motion providing an objective assessment of the performance or rehabilitation.

According to a first embodiment of the present invention, the motion and force processing system is embedded in a replaceable insole of the ski boot inner-lining or directly embedded in the ski boot to analyze the motion of skis in relation to the location and value of force transferred by the skier feet to the insoles of the ski boot and the timing such force is applied.

It is well understood how ski or snowboard turns when moments are applied to the ski edge by skier's body through the forces applied to the skier's foot points of balance (POB)—$1^{st}$ Metatarsal, $5^{th}$ Metatarsal and the foot heel, and how the turning performance is determined by said forces and the reactions introduced by ski-snow contact. Understanding of skiing bio-mechanics allows determination of proper pressure distribution on the skier's foot in order to make the foot pronate to control the external forces that disturb equilibrium of balance. To establish balance platform, skier must place the center of pressure on the outside (of the turn) foot, and only in specific conditions during the turn. In the foot/ski-boot system, the center of pressure (COP), lays at the point where the resulting force ($F_R$) of interaction between the ski and snow acting on a skier at ski between the turns (flat phase of turn), pulls his center of mass (COM) downward towards the snow and is opposed by muscles preventing a fall. Said knowledge may be augmented with real-time tracking of ski boot motion and the distribution of pressure points inside the ski boot during difference phases of turn.

Analyzing motion, one may determine the current phase of the turn and knowing the skier and equipment physical parameters may predict (extrapolate) the desired rate of ski rotation, then provide haptic stimulus indicating time the COP must be transferred form one part of the foot to another part. Such a system, comprising motion and pressure sensors embedded in the ski boots and a smartphone based application may provide real-time feedback to the skier and visual post-run analysis does provide tool in training.

According to a second embodiment of the present invention, the motion and force processing system is embedded in a replaceable insole of a walking or running shoe to analyze the gait and balance of user by estimating vertical ground reaction force vectors applied trough the shoe insoles to the user's feet and limbs in relation to feet motion, then after the analysis, provide haptic corrective feedback to the user.

As the gait analysis is a function of modification of many movement factors, the gait patterns can be transient or permanent. As such the gait analysis system of the second embodiment can aid in both providing information of natural abnormalities and in helping selection of suitable prosthetics, as well as in rehabilitation of temporary gait abnormalities during the recovery from physical injuries, such as cerebral palsy or recovery of stroke patient, or add in training in order to optimize athlete performance of the user.

In accordance with this second embodiment of the present invention, the assessment of gait disorders and effects of corrective orthopedic surgery are facilitated. In addition, the system aids in the selection of options for treatment and for correction of distorted bony anatomy such as a misaligned pelvis or sacrum.

The details of one or more embodiments of the invention are set forth in the accompanying drawings and the description below. Other features, objects, and advantages of the invention will be apparent from the description and drawings, and from the claims.

DESCRIPTION OF THE DRAWINGS

A better understanding of the present invention can be obtained when the following detailed description of the preferred embodiment is considered in conjunction with the following drawings, in which.

Like reference numbers and designations in the various drawings indicate like elements.

DETAILED DESCRIPTION

Figure 1A:
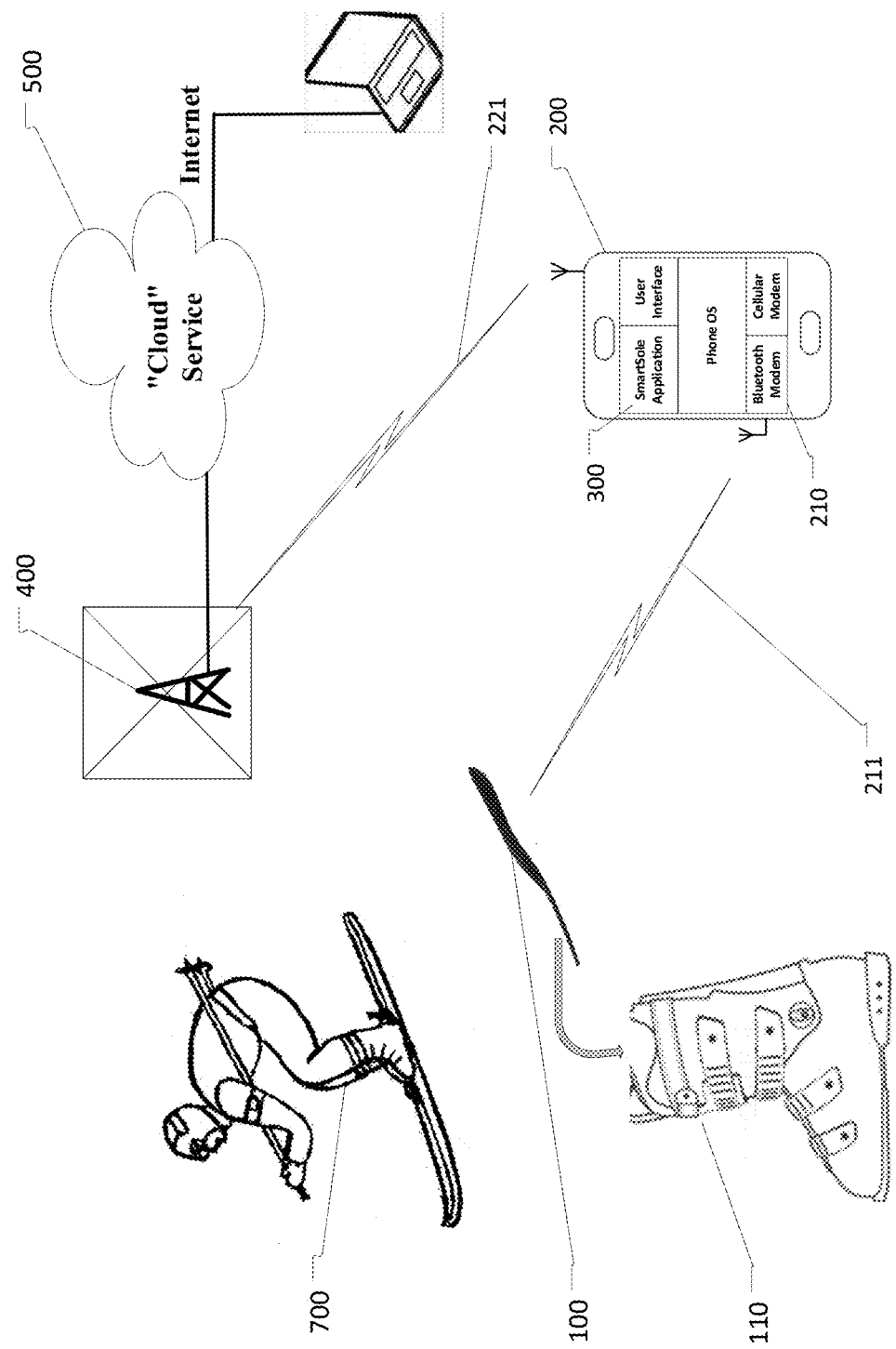
FIG. 1A shows an exemplary ski-boot haptic feedback system.

Aspects of the present disclosure relates to methods and apparatus for establishing relationships between musicians, sharing information, and coordinating rehearsals and performances. Details of some disclosed embodiments are described below with reference to the accompanying figures.

The following is a glossary of terms used in the present application:

Haptic Feedback System—in the context of this invention is a system able to collect and analyze motion and forces applied by the user foot to the insole of the shoe, then after determination of the phase of motion, apply a haptic feedback to the user's foot indicating optimal distribution of the pressure points.

Application—the term "application" is intended to have the full breadth of its ordinary meaning. The term "application" includes 1) a software program, which may be stored in a memory and is executable by a processor or 2) a hardware configuration program useable for configuring a programmable hardware element.

Computer System/Server—any of various types of computing or processing systems, including mobile terminal, personal computer system (PC), mainframe computer system, workstation, network appliance, Internet appliance, personal digital assistant (PDA), television system, grid computing system, or other device or combinations of devices, capable of storing/processing data base comprising of user's information. In general, the term "computer system" can be broadly defined to encompass any device (or combination of devices) having at least one processor that executes instructions from a memory medium.

Mobile Terminal—in the scope of this invention any wireless terminal such as cell-phone, smartphone, etc. comprising a local wireless communication port including, such as a Wi-Fi communication port, a personal wireless communication port including, without limitation, Bluetooth, ZigBee, etc., and further wherein the mobile terminal may be provisioned to operate in a cellular network.

Smart Phone—in the scope of this disclosure, a smart phone may comprise a computing device comprising a wireless cellular communication port, a memory, a processor, wherein the processor is configured to execute software program instructions, and wherein the smart phone may include local and personal area wireless communication ports, a GPS receiver and user interface.

Memory Medium—Any of various types of memory devices or storage devices. The term "memory medium" is intended to include an installation medium, e.g., a CD-ROM, floppy disks, or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed or may be located in a second different processor which connects to the first processor over a network, such as wireless PAN or WMAN network or the Internet. In the latter instance, the second processor may provide program instructions to the first processor for execution. The term "memory medium" may include two or more memory mediums which may reside in different locations, e.g., in different processors that are connected over a network.

Near Field Communication (NFC)—in the scope of this invention is a type of radio interface for near communication.

Personal Area Network (PAN)—in the scope of this invention, is a personal are network radio interface such as: Bluetooth, ZigBee, Body Area Network, etc.

Body Area Network (BAN)—in the scope of this invention is a network of sensors attached to the user body communicating over wireless interface.

Motion Monitoring System—in the scope of this invention is a system able to collect various instantaneous vectors such as: acceleration, angular orientation, geo-location and orientation, then using various mathematical operations to provide visual representation of the user's motion.

Ski Equipment—in the context of this invention, is any part of equipment used by the skier, such as: skis, ski boots, ski poles, ski clothing, ski glows, etc.

Equipment Parameters—in the context of this invention, is ski or snowboard design and manufacturing parameters, such as: length, weight, toe/center/tail, stiffness, etc. are extracted after manufacturing and entered into application.

Turn Symmetry—in the context of this invention the level of correlation between pressure levels and locations of the COF applied during the left and right turn.

User Parameters—in the context of this invention, is user's physical parameters, such as: weight, height, body-type, distance from hip to knee, and knee to ankle, trauma/ injuries, muscular abnormalities, peripheral arterial disease, neuropathy normal/abnormal or pathological gait, skiing competence level, etc. are entered by the user into the application using mobile terminal user (UI) interface or obtained during calibration procedures.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Topological Information—in the context of this invention, information about the topology of the ski slope obtained through any combination of techniques such as: topography maps, GPS, Radio-Telemetry, barometric pressure monitoring, etc.

User—in the context of this invention, person actively using the analysis system.

Point of Balance (POB)—in the context of this invention a three primary points of contact between the foot and the ground located under $1^{st}$ Metatarsal, $5^{th}$ Metatarsal and the foot heel, also known as the foot triangle.

Center of Pressure (COP)—in the context of this invention is a point location of the vertical ground reaction force vector. It presents a weighted average of all pressures over the surface of the foot that is in contact with the ground.

Center of Mass (COM)—in the context of this invention is a point equivalent of the total body mass in the global reference system and weighted average of the COM of each body segment in 3Dimensional space.

Center of Force (COF)—in the context of this invention a point location of a force applied by skier's foot to the insole surface when the whole ski lies flat and in contact with the snow surface reaction force. Said force location is calculated from pressure data obtained from sensors located inside the ski-boot insole and reflect neutral control of ankle muscle.

Ground Reaction Force—in the context of this invention, a force defined by Newton's third law of physics excreted by the ground on a body in contact with it. When person is standing the GRF corresponds with the person's weight and increases proportionally to acceleration when the person is moving. When the person is in motion, the GRF have two components—vertical and horizontal. This horizontal (or frictional) force is sometime referred as a shear force, and the ratio of magnitude of the horizontal force to the vertical GRF yields the coefficient of static friction/shear.

Natural Standing Position—in the context of this invention, it is a position when subject hip and knee joints are extended and in their most stable position and the line of gravity passes posterior to the hop and interior to the knee joints—position used to determine the subject's pronation.

Pronation—in the context of this invention, natural side-to-side movement of the foot during walk or run which starts in the first part of the gait stance phase.

Neutral Pronation—in the context of this invention, a position where the COM is acting inwards and being on the inside of the midline of the foot and the weight is distributed evenly over foot POB and all toes, with slight emphasis of big toe.

Supination (Under pronation)—in the context of this invention, a position where the COM moves outwards and being outside of the midline of the foot and the weight is mostly distributed on the outside the foot and on the outer toes.

Net Force—in the context of this invention, is the vector sum of forces acting on a particle or body. The net force is a single force that replaces the effect of the original forces on the particle's motion. It gives the particle the same acceleration as all those actual forces together as described by the Newton's second law of motion.

Motion Processor—in the context of this invention a processing device configured to execute complex motion fusion algorithms by combining data from an accelerometer, gyroscope and magnetometer in order to provide an accurate representation of orientation in 3D space and to compensate for drift in the sensors.

Azimuth—in the context of this invention, an angular measurement in a spherical coordinate system. The vector from an observer (origin) to a point of interest is projected perpendicularly onto a reference plane; the angle between the projected vector and a reference vector on the reference plane.

Orientation—in the context of this invention, the relationship between the directions of the local coordinate system and the corresponding directions of global coordinate system (compass).

Cloud Server—in the context of this invention is a computing equipment allowing a client application software to be operated using Internet enable devices.

Accelerometer—in the context of this invention is an inertia-based device measuring acceleration component based on device motion and gravity.

Gyroscope—in the context of this invention is a sensor to measure an angular rate of change in device orientation irrespective to gravity.

Magnetometer—in the context of this invention is a sensor to measure magnetic field by computing the angle of the Earth magnetic field and comparing that measurement to the gravity measured by an accelerometer.

Pressure Sensor—Atmospheric—in the context of this invention is a sensor measuring the differential or absolute atmospheric pressure and used to track vertical motion.

Force Sensor—in the context of this invention is a thin-film sensor (resistive, capacitive, etc.), designed to measure pressure (in Newton) applied by the user foot on the insole.

Temperature Sensor—in the context of this invention a thin-film platinum or Nickle, Titanium Silicocarbide, etc. sensor designed to measure temperature by changes of the sensor resistance.

Rotation Vector—Angular Velocity—in the context of this invention is a vector quantity whose magnitude is proportional to the amount or speed of a rotation, and whose direction is perpendicular to the plane of that rotation.

Rotation Matrix—in the context of this invention is a matrix that is used to represent rotation in Euclidean space and to describe device orientation.

Gravity—in the context of this invention is Earth's gravity measured in $m/s^2$ and excluding acceleration caused by the user and consisting of a relative angle between device and gravity vector.

Orientation (attitude)—in the context of this invention is an orientation of the device expressed in Euler angles, rotation matrix or quaternion.

Motion Sensor Fusion—in the context of this invention is a method to derive a single estimate of device orientation and position by combining data from multiplicity of sensors.

Global Coordinate System—in the context of this invention is a x/y/z coordination system referenced to the earth magnetic field and in angle of inclination dependent on geographical location.

Local Coordinate System—in the context of this invention is a x/y/z coordinate of the motion sensor located in the insoles, where the x-axis is a horizontal and points to the toe, the y-axis is a horizontal and points to the left and the z-axis is vertical and points up.

Euler Angles—in the context of this invention is a three angles introduced by Leonard Euler to describe orientation of a rigid object using sequence of three consecutive rotations.

Quaternion—in the context of this invention is a mathematical expression used to calculate rotation state of the device using the axis and angle of rotation.

Intranet—in the context of this invention, a computer network, such as: Ethernet or wireless LAN, for sharing information, and other computing services within an organization with access secured from unauthorized outsiders.

VPT (Vibrating Perception Threshold)—in the context of this invention, a level of specific vibrating stimulus applied to the user's big toe to measure a subject's response thereto and to determine a level of sensation loss (neuropathy).

HIPAA Protocol (Health Insurance Portability and Accountability Act)—in the context of this invention a computer protocol implementing requirements of the US Department of Health and Human Services privacy rules.

Detailed Description of a First Embodiment

A first embodiment comprises a ski-boot (or ice-skate boot) insole configured to measure distribution of forces transmitted to the ski-boot insole during downhill run, a 3D motion processing element, a linear resonant actuator to provide feedback to the skier's foot and a wireless personal are network (PAN) transceiver—such as: Bluetooth, ANT, etc., communicating force and motion data to the smartphone based application. Based on the knowledge of skiing bio-mechanics, and the information received from the ski-boot insole, the smartphone based application predicts the intended ski trajectory, then provides haptic feedback to the foot of the skier, suggesting proper distribution of pressure points on the insole. Furthermore, the smartphone application transmits the pressure and motion data obtained from the ski-boot insole together with the GPS timing and coordinates to the remote location for post-processing using wireless cellular network. During post-processing, a 3D map based on GPS coordinates is retrieved and superimposed on the motion/pressure data, which may be provided in real-time on a remote computer or a smartphone. Alternatively, post-processed data may be stored on the remote server and retrieved later by the user.

The insole of the present invention comprises several Microelectromechanical (MEMS) sensors connected to a motion processor, designed to measure motion in 9-degree of freedom (3D). This capability is achieved by integrating a 3-axis accelerometer sensor, a 3-axis gyroscope sensor, and a 3-axis magnetometer sensor, coupled to the motion processor designed to execute various motion processing algorithms on vectors obtained from said sensors. In addition to the motion sensors, the motion processor, is coupled with multiplicity of force sensors and temperature sensors embedded in the insoles. The pressure sensors provide measurement of ground reaction force vectors recorded at the foot pressure point. By observing change in distribution of the location of GRF vectors in time we can determine migration of the center of force (COF), in relation to motion, we not only can estimate the phase of the turn the skis are in, but based on the previous data and past ski trajectory, estimate future ski trajectory based on said data and the user and equipment information (user weight, height, ski side-cut radius, etc.), Furthermore, based on such information we can provide feedback instructing the user on proper location and time the COP must be located to keep the ski desired trajectory.

Most skiers have an intuitive understanding of skiing, gained from practice and understanding some of the physics behind skiing. Such understanding is useful to skiers of all levels, as it identifies key principles, enabling to properly execute certain movements to improve performance. In general, skiing (downhill), involves high speed run down the sloped terrain using quick turns. The skier gains speed by converting gravitational potential energy into kinetic energy of motion, so the more a skier descends down a heel, the faster he goes. A skier maximizes his speed by minimizing resistance to motion, both from air resistance and snow resistance. While the skier minimizes his air resistance (drag) by reducing his projected frontal area, the reduction of snow resistance requires combination of balance and subtle technique of turn. While the turn is essential to go around objects of gates and arrive safely at the bottom of the slope, the turn itself introduces resistance and as such slows the skier. This is particularly pronounced by less experienced skiers, as they skid around their turns and the skis are tilted on their edge and skis plow into the snow. Also, in some cases, a degree of skidding is unavoidable, more advanced skier, will attempt to carve around the turn using skis natural shape (side-cut), and flexibility. To help in "carving the turn", skier will tilt the skis on the inner edge of the turn, and in general, the larger is the angle between the snow and the ski surface, the tighter the turn is. When the ski is flat on the snow, the radius of the carved turn $R_T$ equals the side-cut radius $R_{SC}$, and the ski turns without skid as it travels in the same direction as its velocity.

However, skid is an important technique used to suddenly change direction, slow the speed or even stop. And unlike carving where a skier eases into the turn, a skidded turn is initiated by simultaneously tilting the edge of skis into the snow and pivoting in the direction of the turn. This results in turning in that direction, due to the plowing effect, since the skis are pointed in a direction that is different from the initial velocity. The steering angle determines sharp is the turn, and the loss of velocity. A steering angle of zero results in the skier moving in a straight line with no turning and no slowing down. A steering angle of 90° results in the skier slowing down with no turning, since the force of the snow plowing into skis without sideway component necessary for turn.

By measuring GRF and motion of the foot with 9-degree or 10-degree of freedom, one can monitor motion in 3D, then using knowledge of skier and ski physical parameters predict the progress of motion by extrapolation.

In general, downhill skiing comprise straight skiing with a flat skis between two consecutive turns, and the intrinsic skill necessary for skiing is the maintenance of balance. Balance is maintained by the skier's foot, which through numerous joints, tendons, muscles provides receptive field for two main balance metrics—Center of Mass (COM) and Center of Pressure (COP). In this context, the process of skiing may be divided into three phases: $1^{st}$—initiate transition of balance (initiate turn); $2^{nd}$—ski flat (flat ski between turns); $3^{rd}$—rotate pelvic (start next turn). All these phases are initiated and maintained through changes in the distribution of foot COP and application of said pressure to the ski-boot through the ski-boot insole.

Without much generalization, it is possible to say that the COP during the turn is located on the outside foot of the turn, while during the flat ski phase (between turns), it is distributed evenly between both feet and the net COP lies somewhere between the two feet depending on the relative weight taken by each foot. Furthermore, we may say that the location of COP under each foot is a direct reflection of the neural control of the ankle muscles. The location of COP under each foot is a direct reflection of the neural control of the ankle muscles. Any movement that flexes the foot or toes downward toward the sole (plantar flexion), will move the COP toward back of the foot, while movement of the foot in upward direction (dorsiflaxion), will move COP toward the front of the foot, the movement of foot inward (invertor), moves COP towards the outside of the foot.

The position of COP can be obtained by placing two or more pressure sensors in the ski-boot sole, then synchronizing the changes in COP with the motion vectors obtained from the 3D motion monitor. The knowledge of place the COP is at the present time combined with the knowledge of past trajectory, present orientation in 3D space, motion vectors and the location of COP allows prediction of the future ski trajectory. Such trajectory may be changed or influenced by the change in pressure applied to the foot—thus influencing change of COP and in turn change of turn parameters. Such "advise" about the timing and need to change location of COP can be provided through feedback to the skier foot.

This invention describes a system capable of monitoring motion of the skier foot in relation to the snow, measuring the location and distribution of force—pressure point(s), inside the ski boot and provide haptic feedback to the skier's foot, instructing on the time and direction the center of force (COF) must be moved for the optimal execution of the current turn. Such system comprises a ski-boot insole for processing of motion and to provide haptic feedback, a smartphone based monitoring application communicating with the insole using Bluetooth (or other suitable), personal area network (PAN) wireless technology, and with the cloud-based server using cellular wireless technology.

The exemplary system is presented in FIG. 1A. Here an insole 100, of a ski boot 110, with an insole 100, communicates with a monitoring application 300, hosted in a smartphone 200. The monitoring application 300 pre-processes the motion and pressure data, retrieves a GPS time and coordinates from the smartphone and sends said data using smartphone cellular radio interface 221, to the cloud service 500, for further post-processing, while the pre-processed motion and pressure data are used to provide haptic feedback to the actuator located in the insole. Based on GPS coordinates extracted from data, the cloud server retrieves 3D map of the area, then superimposes the graphical and numerical parameters of the run on said 3D map. This map, together with the graphical and numerical parameters of the run may be displayed on the remote computer or viewed on the user smartphone.

Figure 2:
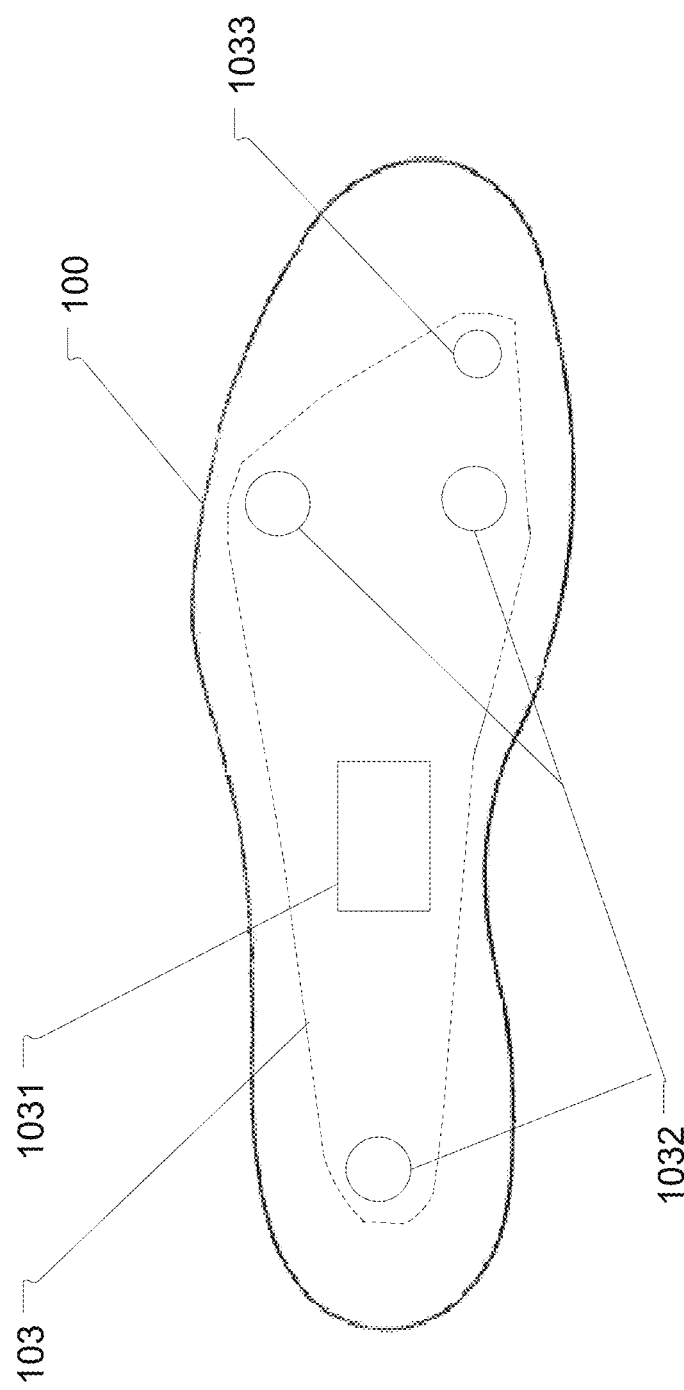
FIG. 2 shows an innersole and the components of the exemplary haptic feedback system.
Figure 3:
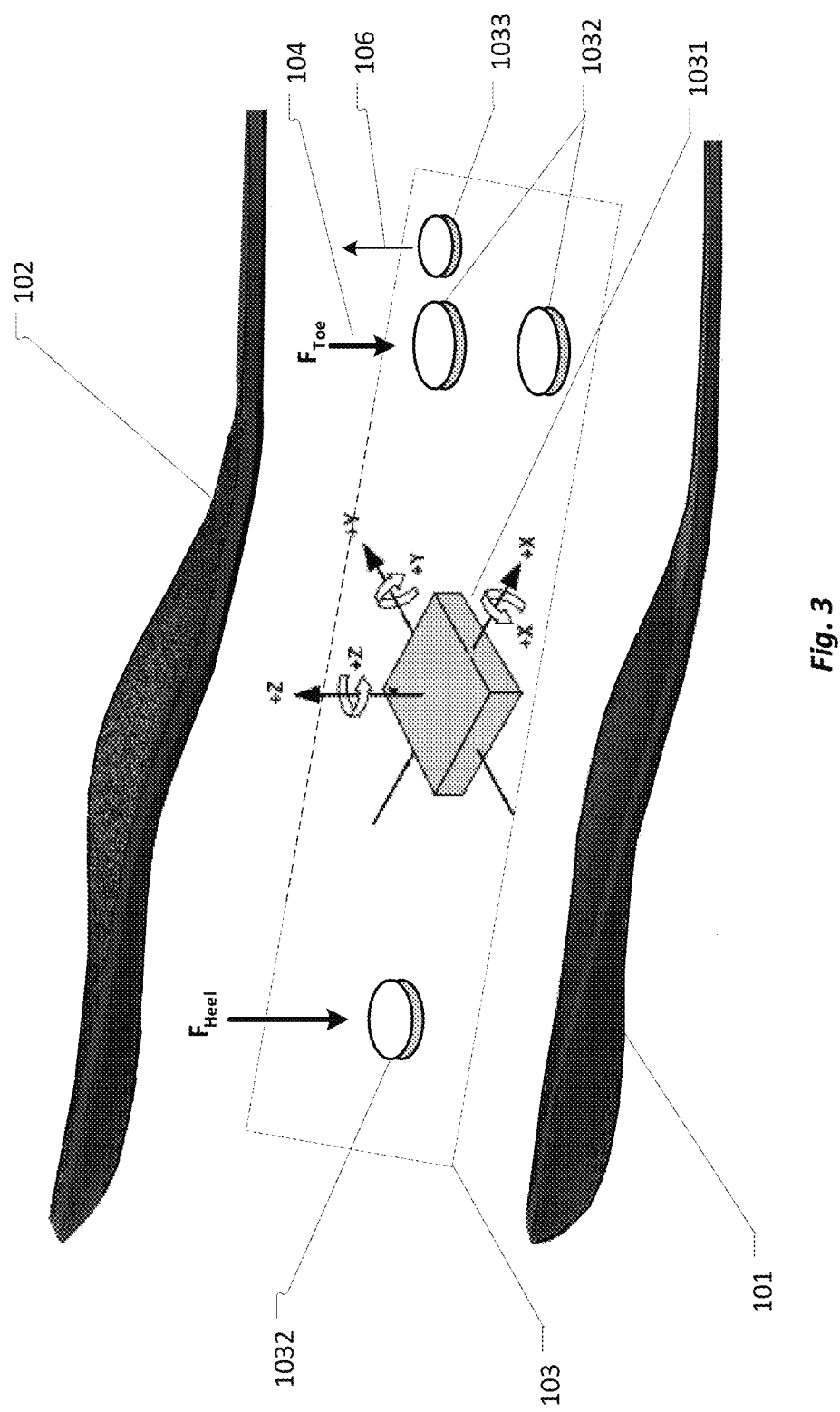
FIG. 3 shows a cross-section of the innersole.

Ski-boot insole 100, presented on FIGS. 2 and FIG. 3, comprises of a lower 101, and upper 102, insole surfaces and a motion processing and feedback sub-system 103, sandwiched in between insole surfaces. The motion and feedback sub-system consist of a motion processing element 1031, two or more pressure/force sensors 1032, and a haptic actuator 1033. The motion processing element 1031, is configured for analysis of motion with 10-degree of freedom comprising several inertial MEMS sensors: a 3D gyroscope; a 3D accelerometer; a 3D magnetometer (compass); and an atmospheric pressure sensor.

The 3D gyroscope is used to measure angular rate change by the insole in degrees per second, thus allowing measurement of angle, travel and as such, track changes in the insole orientation (pitch, roll and yaw angles). The accelerometer is used to measure acceleration of the insole caused by motion due to gravity in an X, Y, Z coordinate system by computing the measured angle of the device, compared to gravitational force and the results are expressed in m/s². By integrating acceleration vector, a(t) over period of time, we obtain velocity function v(t). The 3D magnetometer measures the earth magnetic field at specific location. By computing the angle of the magnetic field, and comparing that angle to gravity obtained from accelerometer, we are able to determine the orientation of the insole with respect to magnetic North. Besides, sensing the direction of earth magnetic field, magnetometer is used to eliminate drift of gyroscope. Furthermore, the insole motion processing element employs an atmospheric pressure sensor to obtain changes in the altitude and rate of descent by detecting ambient air pressure ($P_{amb}$) according to equation:

$$h_{alt} = (1 - (P_{amb}/10132)^{0.190284}) * 145366.45$$

to track vertical motion.

By observing three-dimensional vector of gravity measured by the accelerometer along with measurements provided by gyroscope, we can determine orientation of the ski (pitch, roll, yaw), while the skier is in motion. By subtracting gravity vector form acceleration, we obtain linear acceleration of the ski. The orientation angles describe motion and are used to provide graphical representation of motion. Furthermore, we derive a rotation vector from results provided by accelerometer, gyroscope and magnetometer. This vector represents a rotation around a specific axis and corresponds to the components of a unit quaternion, which represents yaw, pitch and roll and is used to graphically represent motion of the insole.

The quaternion of the insole (and ski-boot), is calculated by, first converting gyroscope angular rate to a quaternion representation:

$$dq(t)/dt = \frac{1}{2}\omega(t) * q(t),$$

where ω(t) is the angular rate of motion and q(t) represents normalized quaternion. Then, we convert the accelerometer results from local coordinate system, represented as $A_L$ to global coordinate system, represented as $A_G$, by using previously obtained quaternion as:

$$A_G(t) = q(t) * A_L(t) + q(t)'.$$

Then calculate acceleration quaternion as:

$$qf(t) = [0 A_{Gy}(t) - A_{Gz}(t) 0] * gain$$

which is added as a feedback term to quaternion from gyroscope, then add magnetometer data to the azimuth (yaw) component of the quaternion.

Figure 4:
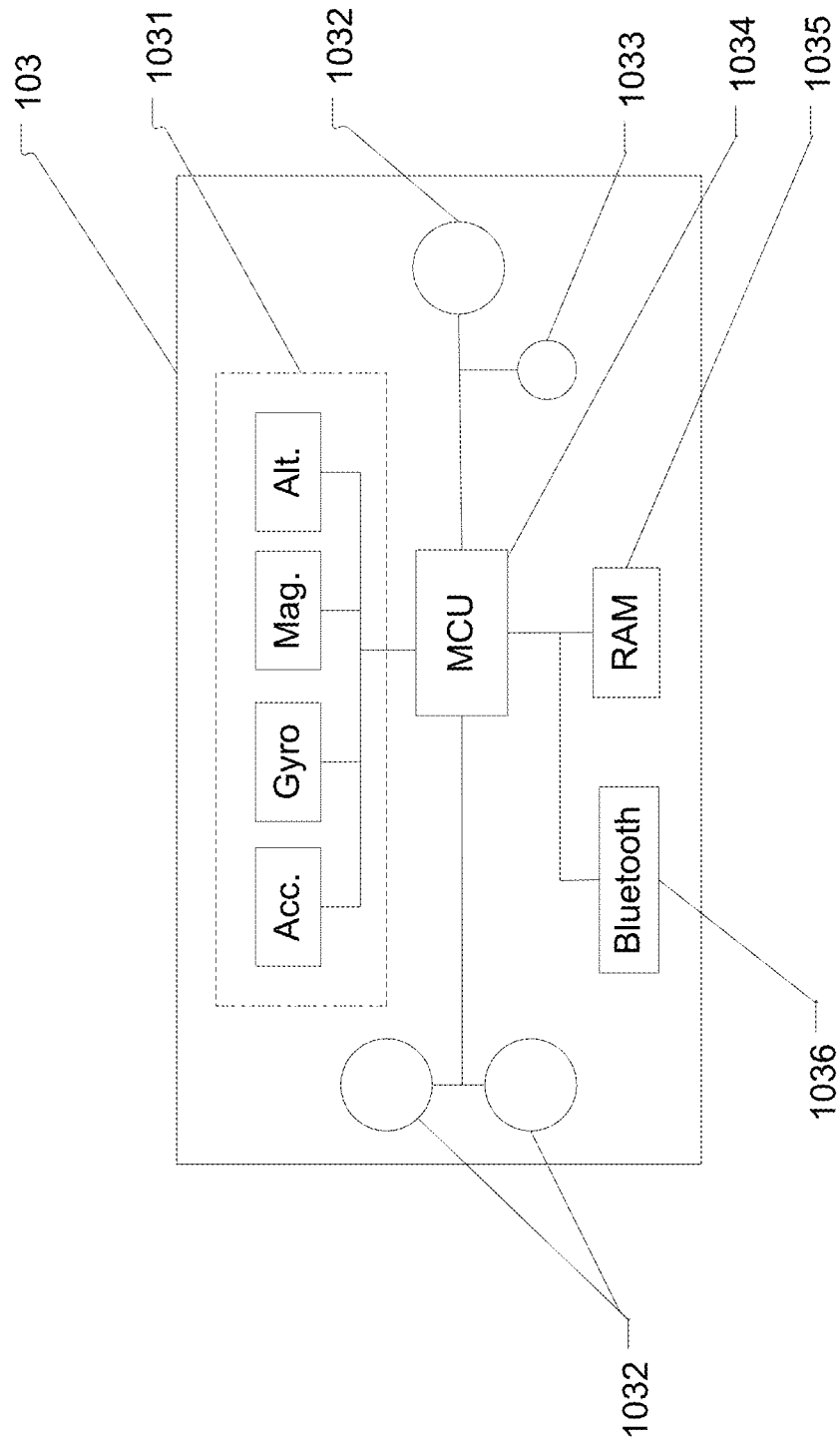
FIG. 4 shows a relation between the skier's foot and the components of the ski-boot innersole.

The exemplary ski-boot insole motion processing and feedback sub-system 103, is presented in FIG. 4, and comprises of: a motion processing element 1031, comprising a 3-axis accelerometer, a 3-axis gyroscope, a 3-axis magnetometer and a barometric pressure sensor. In addition, the motion processing and feedback sub-system consist of several force pressure sensors 1032, a haptic feedback actuator 1033, a Bluetooth RF interface 1036, and microprocessor 1034 with its program memory 1035. The sensors within the motion processing element 1031, are connected to the microprocessor 1034 using one of appropriate digital interfaces, such as I2C, or an appropriate analog interface. Similarly, the force pressure sensors may be connected to the microprocessor analog-to-digital (ADC) converter using appropriate analog interface or directly to the microprocessor digital interface, while the haptic feedback actuator may be connected to the microprocessor digital-to-analog (DAC) converter.

Figure 5:
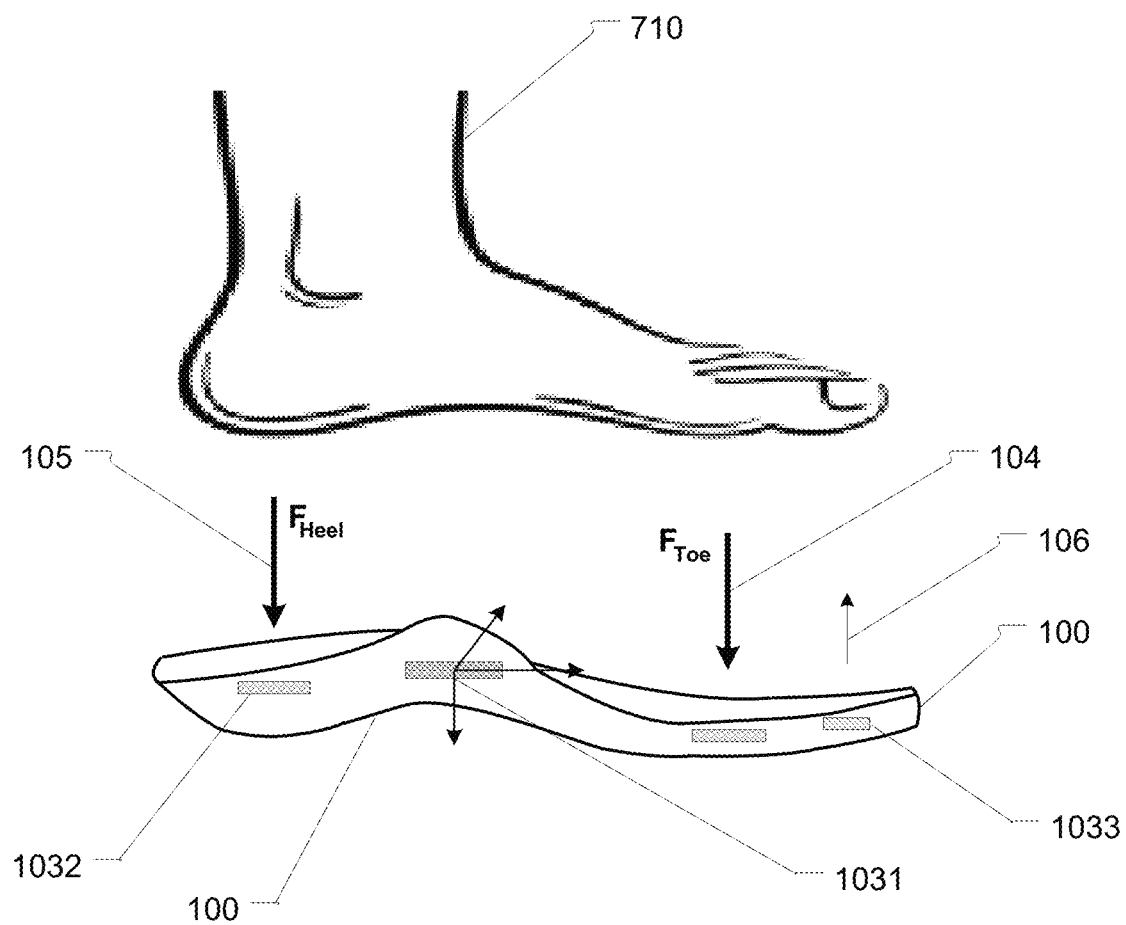
FIG. 5 shows an exemplary architecture of the haptic system controller.

The relation between skier's foot 710, and the ski-boot insole 100, is presented in FIG. 5. During the run, the location of the pressure points to the ski-boot/ski and the distribution of pressure (force) between both feet provides the kinetic mechanism necessary to initiate and end a turn. While between turn—frequently referred a 'flat ski', the force is distributed equally between both feet and equally between front and back of the foot, the location of the pressure points between the feet and inside the ski-boot changes during the turn. From FIG. 5, one may observe two main location of the force—at the front of the foot ($F_{Toe}$) 104, and the back of the foot ($F_{Heel}$) 105. The actual location of those pressure points and consequently the location of center-of-force (COF) may be measured by two or more force sensors 1032. The haptic feedback 106, to the skier foot is provided by actuator 1033.

Each turn in skiing may be separated into three phases: 1) ski flat phase; 2) start of transition phase; 3) pelvic leg rotation phase. During the ski flat phase, the skier COF is distributed evenly between both skis and located in a neutral point (evenly distributed between toe and heel of the insole). The skier selects inner ski—effectively selecting direction of the turn and start the transition phase. At this moment, the COF of the inner foot migrates toward the pinky toe and initiated forward movement on the "new" outer ski, this moves the COF of the outer foot toward the big toe. Then enters the third phase by rotating his leg pelvic moving the COF firmly on the outer ski which places the resulting force $F_R$ on the edge of the outer ski.

Figure 6A:
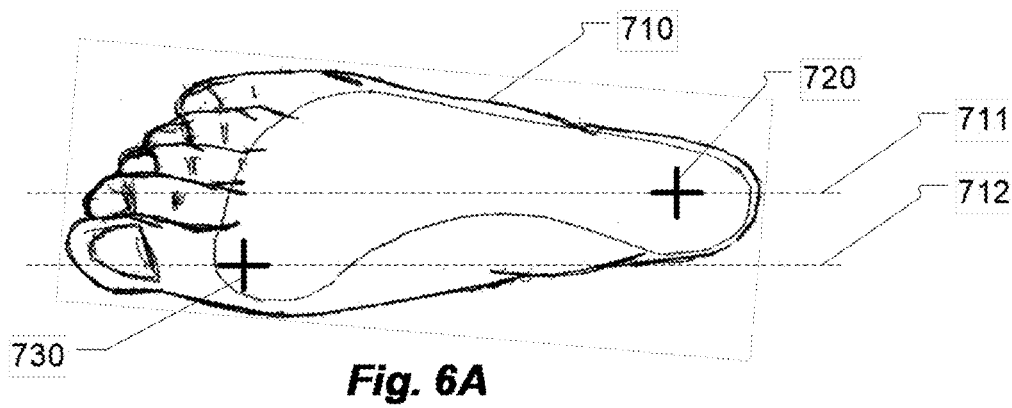
FIG. 6A shows a skier foot bio-mechanical pressure points.

For the outer ski, this process is presented in FIGS. 6A, 6B and 6C and described below. In FIG. 6A, the foot 710, during the flat ski phase between edge change, the pressure is distributed evenly between two main mechanical points 720 located at the heel on the centered axis 711, and on the center of head of the $1^{st}$ metatarsal (MT) bone 730, of a foot and centered along the inside edge 712.

Figure 6B:
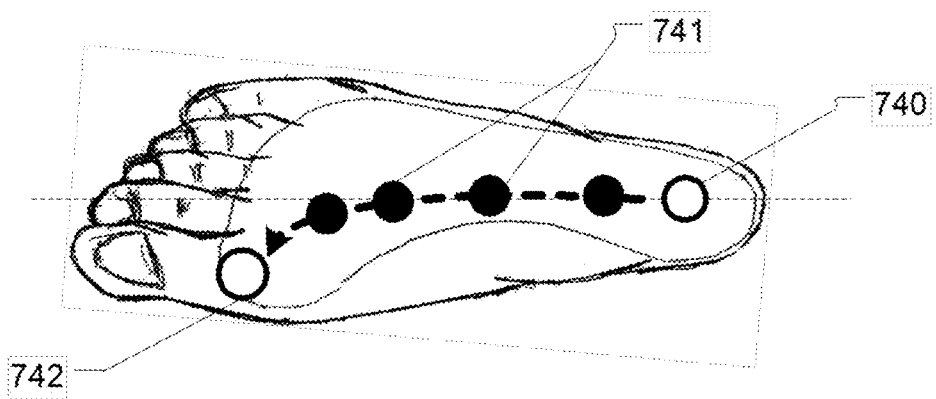
FIG. 6B shows the center of force (COF) point under the heel and its forward transition to become center of pressure (COP) in the phase between two consecutive turns.
Figure 6C:
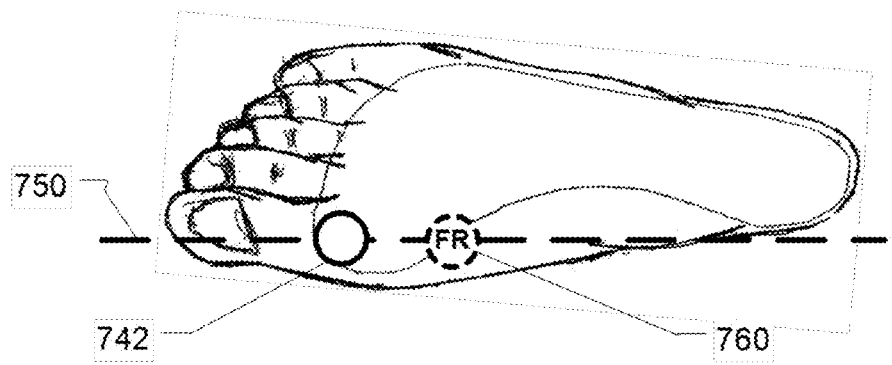
FIG. 6C shows the COP position at the end of the turn when it lays over the top of the inside ski edge and on the same axis as the center of mass (COM) resulting force ($F_R$).

The start of transition is presented in FIG. 6B, here, when the COF 740 is located under the skier heel and progresses forward to position 742, —the head of the $1^{st}$ MT. The COF essentially "rolls" inwards, the ankle is plantar flexed, and the foot is inverted, the leg rotates while COF moves forward along arc 741, towards the head of the first MT. When the head of the first MT is maximally loaded (FIG. 6C), the COF and the skier fully rest on the outer foot (monopodial stance), while the resulting force $F_R$ 760 align with the COF above the edge of the outer ski 750. At this moment, the rolling of the foot inwards generates torque, which is directed into turn.

Figure 7A:
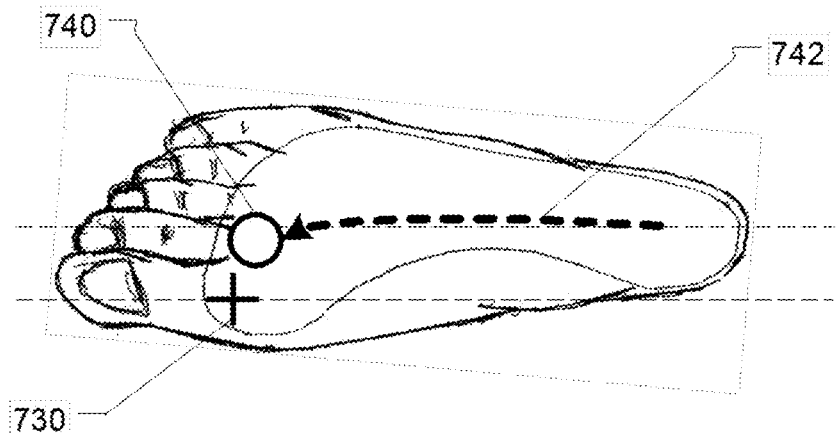
FIG. 7A shows the incorrect migration of the COF during turn from the foot heel to the head of the second toe.
Figure 7B:
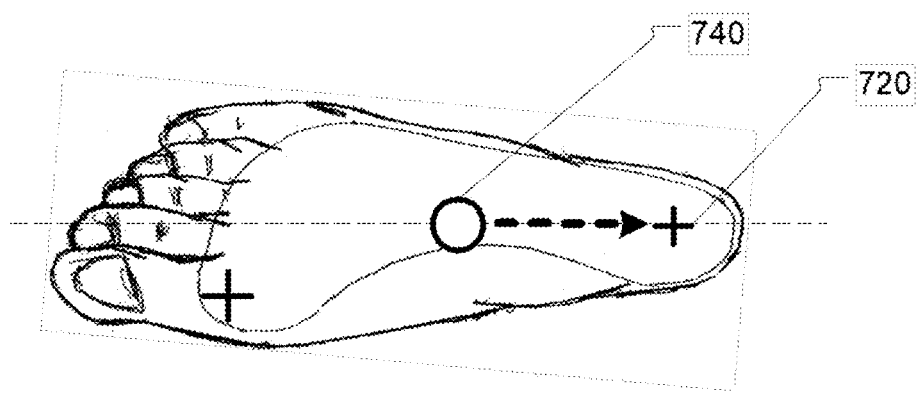
FIG. 7B shows the migration of the COF back from the incorrectly placed COF to the center of the foot and back to the heel.

When the distribution of pressure between skis or the transition of COF from the heel of the outer foot to the head of $1^{st}$ MT fails, the turn is unsuccessful, and skier loses his balance. The graphical representation of such turn is presented in FIGS. 7A and 7B. At some point between the edge change but before the new outside ski attains significant edge angle (without necessary plantar flex of an ankle), a moment develops between the inside edge of the ski and the COF resulting in inversion moment of force. Torque associated with vertical axial rotation of the leg, FIG. 7B, will reverse the movement of the COF 745, to the point of origin 720 as it is aligned with the heel and lower limb. Such reverse cannot be stopped, and skier loses his balance.

Figure 8:
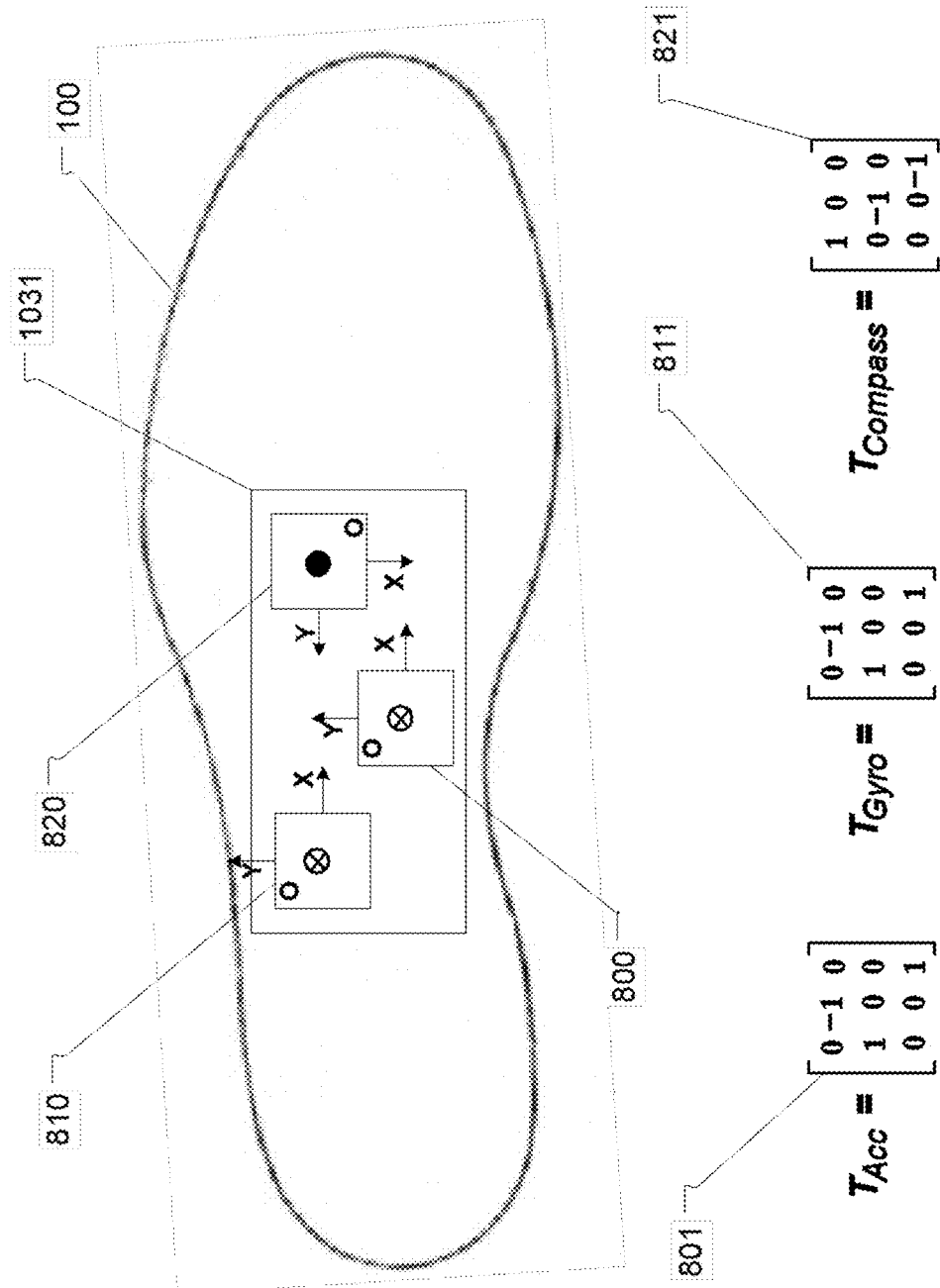
FIG. 8 shows the orientation of the motion sensors (accelerometer, gyroscope, magnetometer), and their transformation matrixes.

An exemplary orientation of motion sensors within the insole and its relation to their respective matrix is presented in FIG. 8. This relation is important to establish local coordinate system, as the matrix obtained from different sensors will rotate depending on insole orientation in reference to the global coordinate system. The motion processing element 1031, embedded in the ski-boot insole 100, and comprises of: 1) an accelerometer 800, which Y axis points to the left side of the insole, the X axis points to the front of the insole and the Z axis points up; 2) a gyroscope 810, which Y axis points to the left side of the insole, the X axis points to the front of the insole and the Z axis points up; and a magnetometer 820, which Y axis points to the back of the insole, the X axis points to the right of the insole and the Z axis points down. Related to this orientation of sensors are respective matrixes: 801, 811 and 812.

Figure 9:
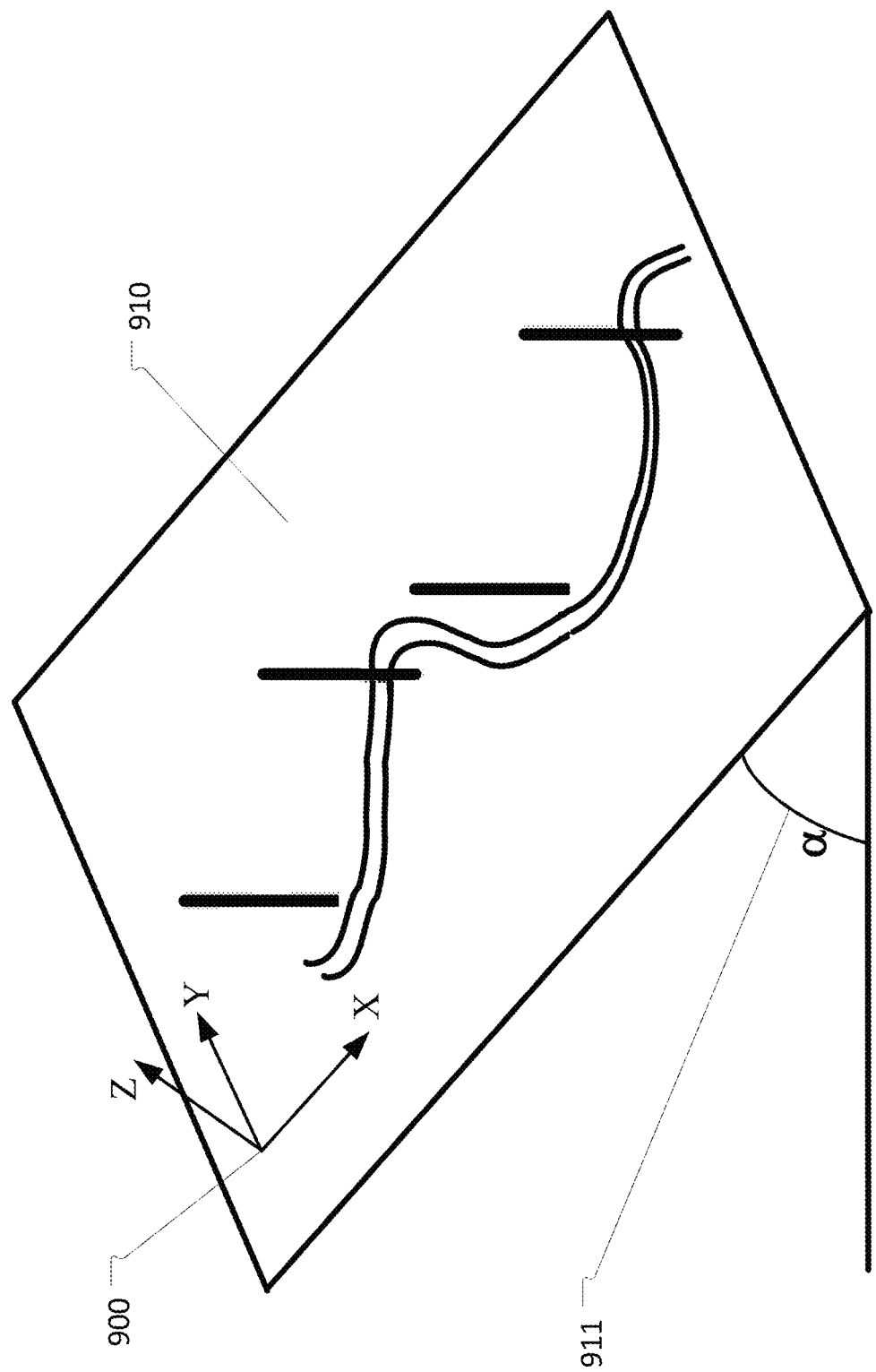
FIG. 9 shows the view of global coordinate system in relation to ski slope.
Figure 10:
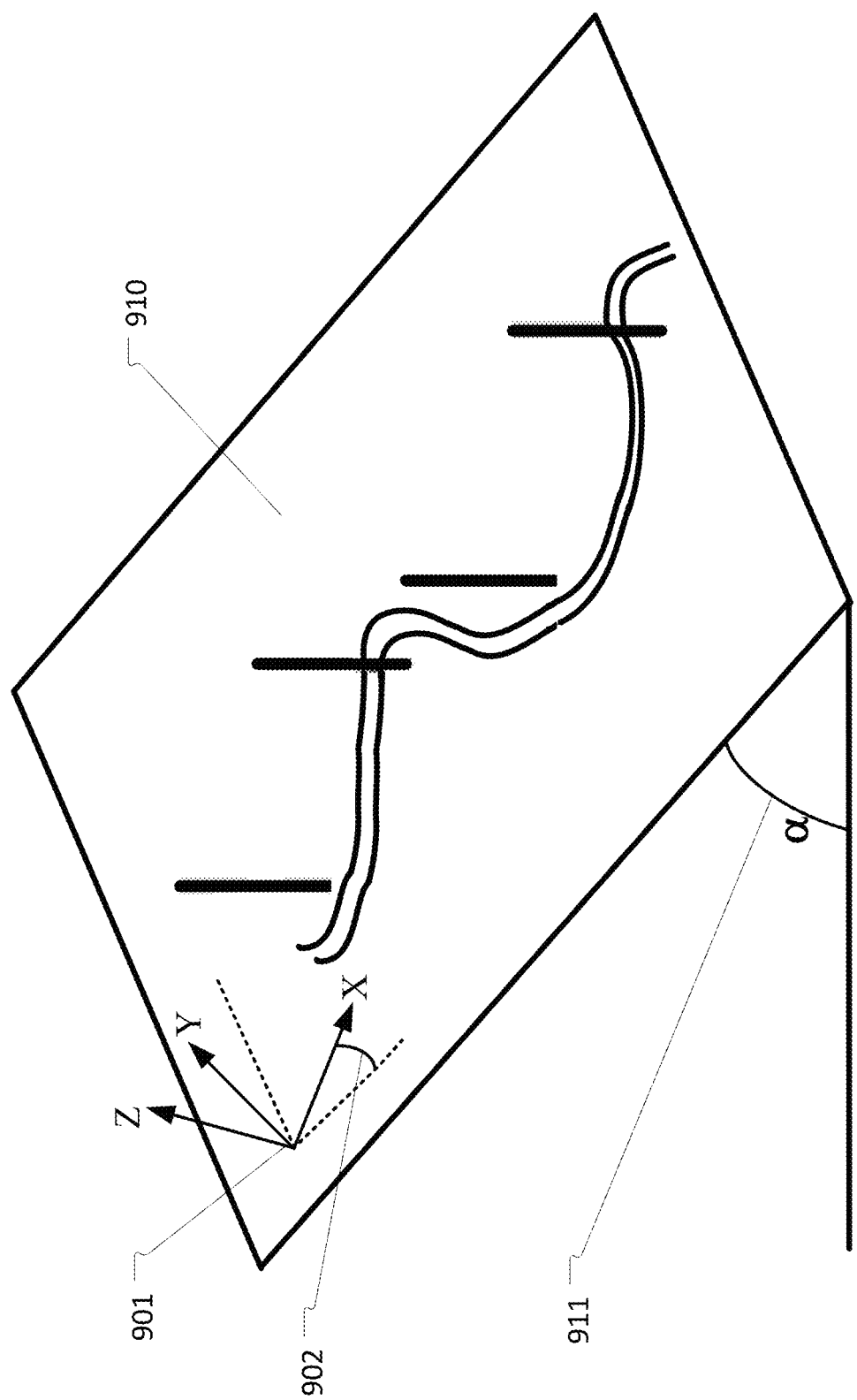
FIG. 10 shows the view of local (ski-boot) coordinate system in relation to the ski slope.

The insole global coordinate system is established in reference to the earth magnetic field at the specific geographical location obtained from the magnetometer 820, by comparing its angle to gravity measured by accelerometer. The orientation of the global coordinate system 900, to the slope 910, with an incline a 911, is presented in the FIG. 9. Here, the Z axis is perpendicular to the ground and the negative Z points in direction of earth gravity. The X axis points to East and the Y axis points to magnetic North. After the global coordinate system is established, the local coordinate system 901 in FIG. 10, a coordinate system of the insole in relation to the global coordinate system may be calculated by reading measurement form accelerometer and gyroscope.

Figure 11:
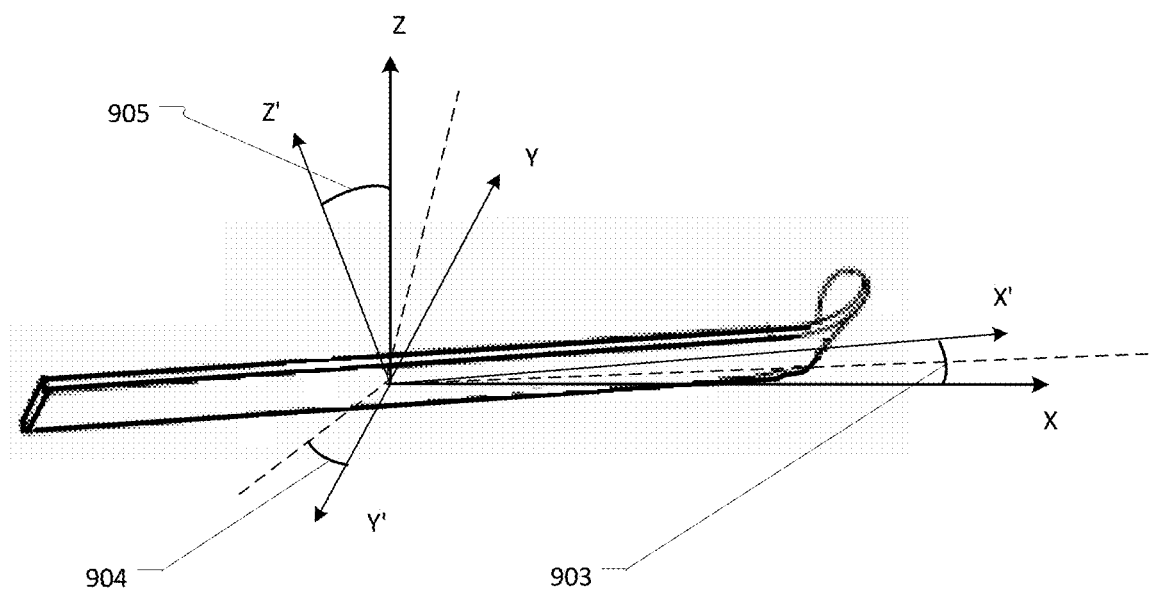
FIG. 11 shows the transformation of local coordinate system during turn.

The method of presenting motion and orientation of the insole and by extension ski in the 3D space can be explained based on FIG. 11 and the processing allowing visualization of said motion described in the following sections. Here at time t0, the ski is flat and with the X axis pointing horizontally in the direction of slope line. The Y axis points to the left, while the Z axis point upward. After start of transition, at time $t_1$, ski rotates along the Z axis by angle $\Psi$(yaw), 905, and along the X axis by angle $\theta$ (pitch), 903, and along the Y axis by angle $\Phi$ (roll), 904, into left turn. This motion may be described in terms of Euler Angles using Euler motion theorem as three consecutive rotations of coordinate system xyz⇒x'''y'''z'''⇒x''y''z''⇒x'y'z', where the $1^{st}$ rotation is along the z-axis, $2^{nd}$ rotation is along the former x-axis and $3^{rd}$ rotation is along the former y-axis.

The insole orientation may also be described in terms of matrix rotation. For a 3D matrix the rotation $\theta$ (pitch), may be described as:

$$R_\theta = \begin{bmatrix} \cos\theta & -\sin\theta & 0 \\ \sin\theta & \cos\theta & 0 \\ 0 & 0 & 1 \end{bmatrix}$$

so the vector $V_0=[1,2,0]^T$ will become $v'=[\cos\theta, \sin\theta, 0]^T$. As the rotation matrix are orthogonal with detriment 1 and with own transpose and an inverse, the rotation matrix will reverse its rotation when multiplied with the rotation inverse. We can also use the matrix rotation to obtain direction of earth gravity in relation to orientation of the insole. When the insole change orientation, its Z axis moves from z to z' by rotation matrix A, according to z'=A*z. As for the local (insole) coordinate system the z' vector is $[0,0,1]^T$, the vector z is obtained by the inverse of rotation matrix.

Rather than use computationally intensive matrix rotation to obtain insole orientation, we may use mathematical expression of quaternion to calculate insole rotation state according to Euler's rotation theorem stating that device orientation may be expressed as rotation about one or more axis. This axis representing unit vector magnitude and angle remains unchanged—except for the sign, which is determined by
the sign of the rotation axis represented as three-dimensional unit vector $\hat{e}=[e_x e_y e_z]^T$, and the angle by a scalar a.

Calculation of quaternion requires only four terms when the axis and angle of rotation is provided. Quaternion extends complex numbers from two-dimensions to four-dimensions by introducing two more roots of −1 as:

$$i^2 = j^2 = k^2 = ijk = -1$$

which are then multiplied with real components as:

$$r + ix + jy + kz$$

then conjugate and normalize to arrive with unity $|u|=1$, or quaternion.

Figure 12:
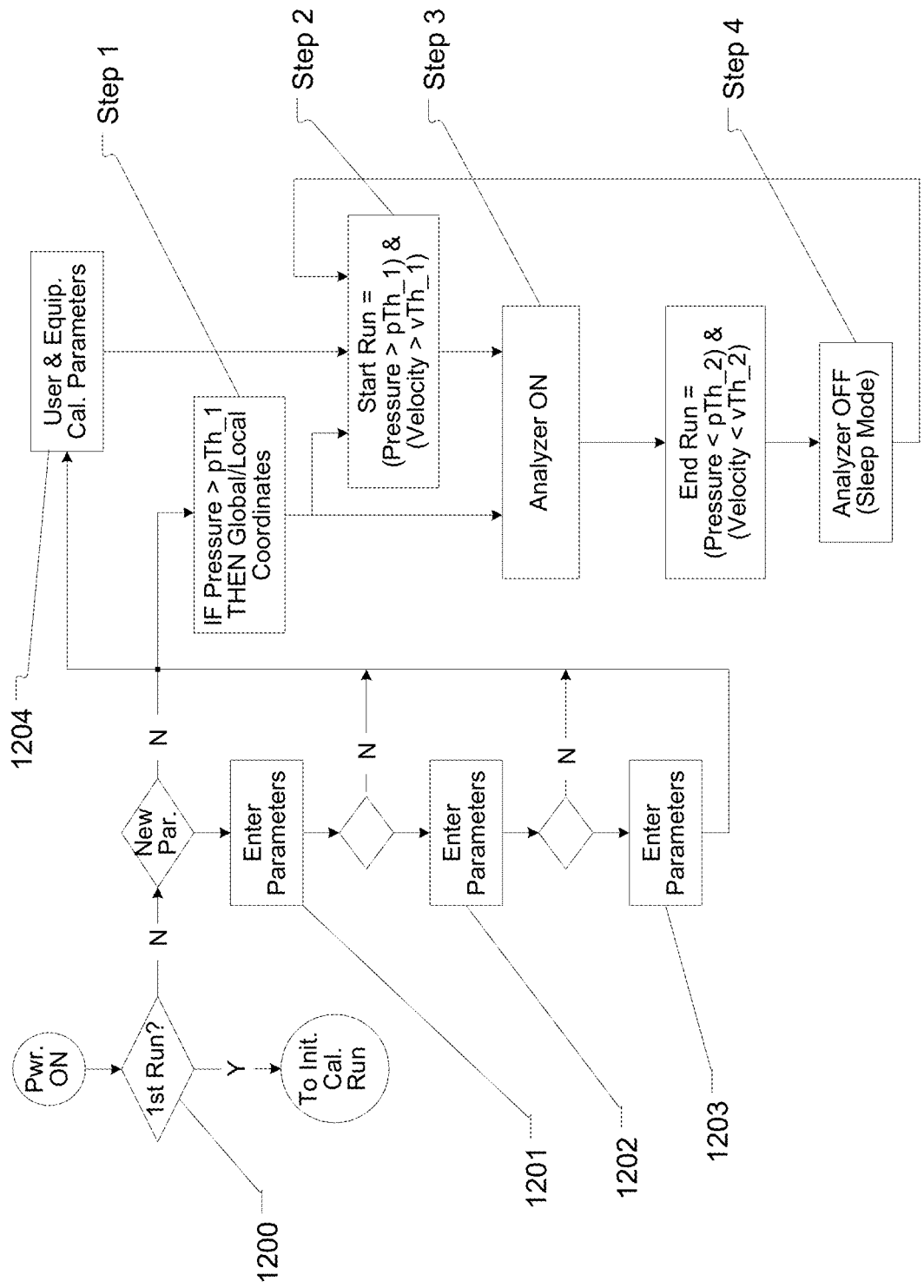
FIG. 12 shows a control process of the haptic feedback system.
Figure 13:
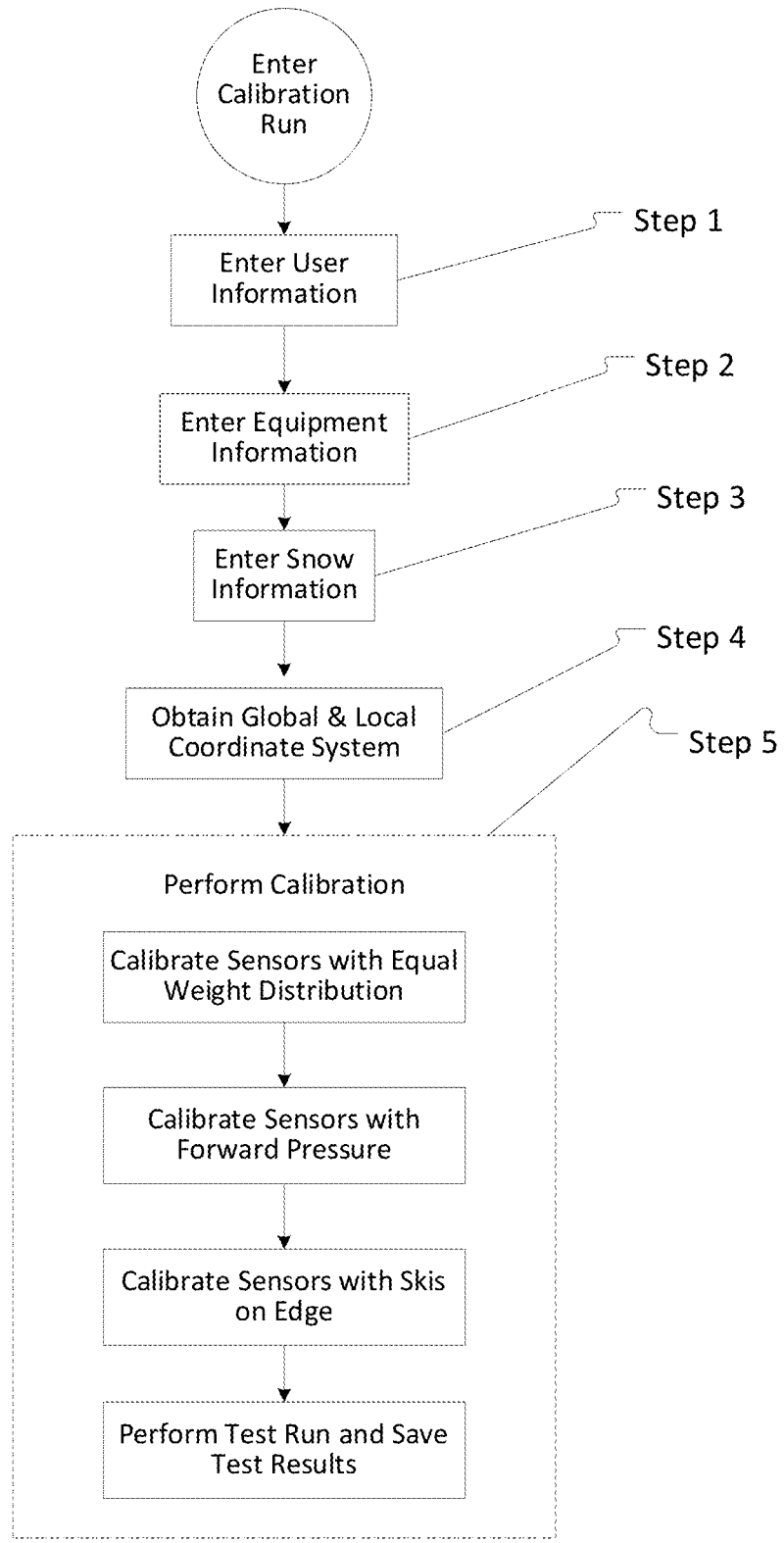
FIG. 13 shows the flow of the haptic system initial calibration.

Operations and procedures of said system is presented in FIGS. 12 and 13 and described in detail in the following sections. In FIG. 12, upon initial power-up and association of the insole Bluetooth transceivers with the application, the system control program checks if this is $1^{st}$ run 1200, indicating the initial calibration procedure was executed. Depending on user parameters, such calibration may be performed during the first run of the day, or at the request by the user, to allow for adjustments to the changing snow conditions, etc. If this is the $1^{st}$ run, application enters the initial calibration routine of FIG. 13, otherwise, user is given an option to update through the smartphone user interface (UI), to update one or all system parameters. If said option is rejected, application enters the main control loop, otherwise, the user is prompted to select which information—first (user parameters), second (equipment parameters), or third (snow condition parameters).

The First information 1201, comprises of user parameters consisting among the others: body weight; height; and skiing proficiency level—"beginner", "intermediate", "advanced", "professional".

The Second information 1202, comprises technical parameters of the user equipment, consisting among the others: length of the ski; ski natural turn radius (side-cut); etc.

The Third information 1203, comprises the snow conditions present during the calibration run, such as: "groomed slope", "icy", "powder". This information is used to derive two coefficients—first, to scale the time between the start of transition and when the COF reaches position 742 (FIG. 6B); second, to scale the distribution of COF between inner and outer ski.

The second and third information may be entered by the user manually or scanned to the application from the QR-code or NFC parameter tag attached to the equipment.

The initial calibration procedure comprises of 5 steps which are described in FIG. 13, and in the following paragraphs.

In Step 1, user is instructed to enter his physical parameters, such as weight, which is used to calculate the distribution of force between both skis using Newton's Second Law as well as calculating distribution of force inside the ski-boot.

In Step 2, user enters equipment parameters by either scanning a QR-code or an NFC tag attached to the equipment or manually using smartphone UI. Among the others, some of parameters like the length and the turning radius or, side-cat of the ski are important factors used in conjunction with motion vectors to calculate the ski effective turning and derive an optimal turning radius during turns.

In Step 3, user enters the current snow condition of the slope. This is used to appropriate scale the pressure point (weight) distribution and timing of COF change in different condition of the slope, for example change of technique between powder skiing and skiing on icy snow.

In Step 4, application instructs the user to step into the skis and reads data from motion sensors for the purpose of establishing global and local coordinate system, then in Step 5 instructs the user to perform several exercises:

1) Stand in normal, relaxed bi-pedal position with body weight equally distributed between both skis, then record the force [N], measured by each pressure force sensor;
2) Stand in a crouching position, leaning forward and elbows resting on the knees, then record the force [N], measured by each pressure force sensor;
3) With both skis parallel and without support of the ski poll, bend knees and push inward (as during sharp turn with both skis on the edge), then record the force [N], measured by each pressure force sensor;
4) Instruct user to make a run consisting at least four carved turns. Allow for the ski to accelerate by ignoring first two turn, then record motion parameters during two consecutive turns;
5) End calibration procedure.

After power ON, the MCU 1034, enters standby mode and remains in said mode until an interrupt from the insole pressure sensor is above threshold pTh_1, indicating both of user feet are in the ski-boot and on the ground. If new calibration is not required, system enters normal operation, FIG. 12, Step 1, obtains global and local coordinate system, then enters user's information. In Step 2, system starts monitoring motion, and if the velocity exceeds threshold vTh_1, indicating start of the run, enters into Step 3, then start sending motion and forces data to the smartphone application over radio interface 211. System remains in State 3, until velocity of the system is above threshold vTh_2 and the pressure force measurement is above threshold pTh_2. When the velocity is below threshold vTh_2 and pressure forces is below threshold pTh_2, indicating end of day (ski-boot off), or time-brake in skiing (lift, rest, etc.), system enters Step 4, stops processing of motion and forces, forces radio interface transceiver 1036, into power OFF mode and MCU 1034, into a standby mode—thus conserving power consumption of the system. After exiting Step 4, system remains in the sleep mode until condition of Step 2—pressure force above pTh_1 and velocity above vTh_1 conditions are not satisfied.

The motion and pressure force data received from the insole 100, by the smartphone 200, is processed by application 300 to provide user with the haptic feedback. Based on signal from sensors, using inertia navigation algorithms, application calculates kinematics of the ski trajectory. Then using user parameters, creates biomechanical model of foot/ski interface, and the sensor kinematics is translated to segments kinematics by measuring the position (and timing) of COF. Such calculation provides two results: one, current ski trajectory; two, prediction of future trajectory in relation to the local coordinate system and location of COF. The first set of results are sent to the cloud-based server 500 for further processing using smartphone cellular radio interface 221, while the second sets of results is used to provide corrective feedback to the user foot.

This corrective feedback is in form of haptic pulses applied by the haptic actuator to the big toe of the foot. This feedback provides information of timing, direction and destination of the COF necessary to successfully start and finish turn. This feedback may be coded in various ways, for example, different frequency and/or force during different phases on turn, etc.

Figure 17:
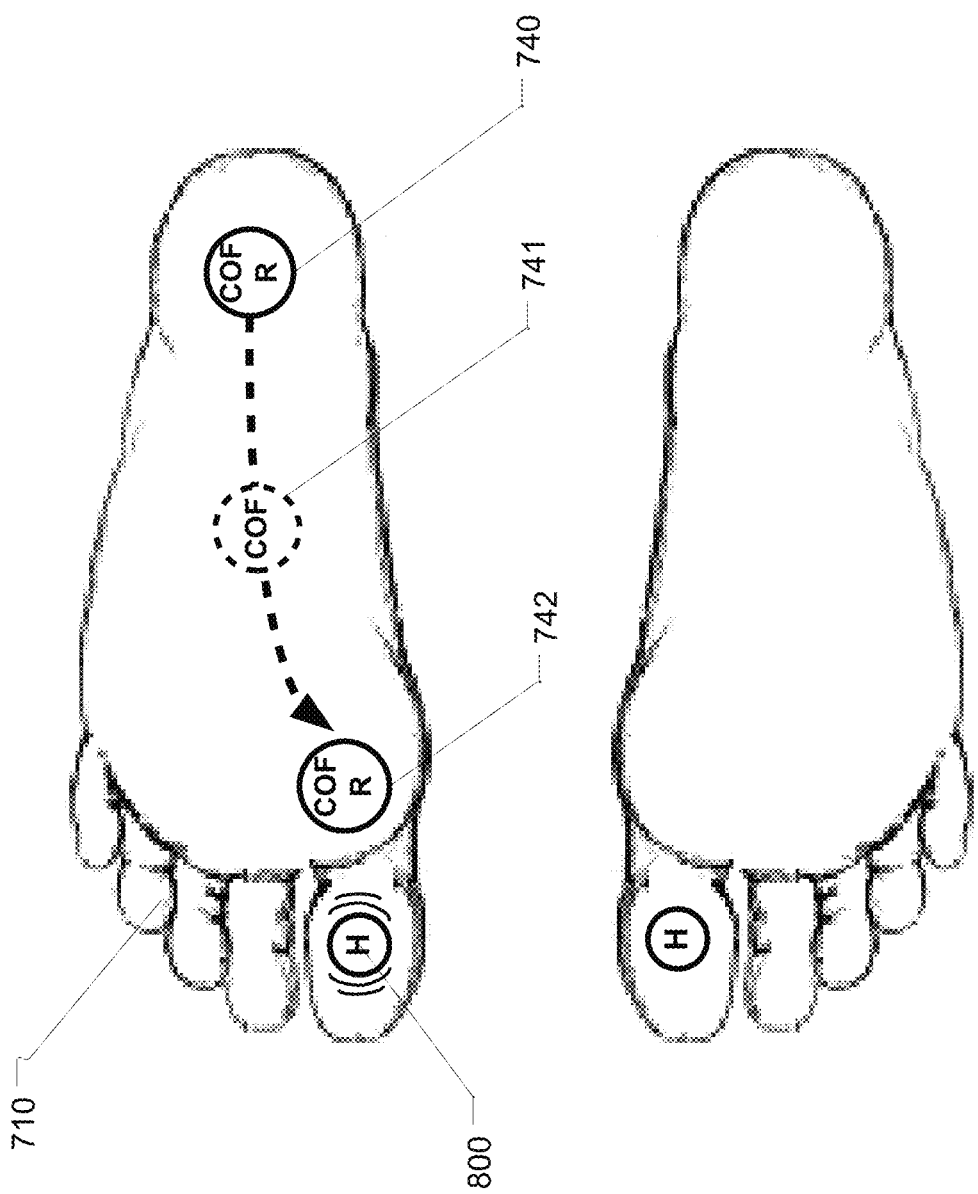
FIG. 17 shows an operation of haptic feedback actuator on the outside foot during the transition into left turn.

Operation of said haptic feedback is presented in FIG. 17. Here we see the outside (of the turn) foot 710, right after start of transition, which the haptic feedback actuator 800, vibrating at high frequency (or force), when the COF is still located under skier heel, indicating time to transition on the outside ski and move COF to the base of $1^{st}$ MT. The vibration frequency may decrease while COF moves forward to new position 741, and completely stop when the COF reaches the desired position 742, while never stop vibrating at high frequency when the COF fails to reach the base of $1^{st}$ MT.

Together with the first set of results, application sends to the cloud server GPS coordinates and timing. The first set of data is then used to generate a numerical and graphical presentation of the run. An exemplary representation of run data is presented in FIGS. 14, 15 and 16. Such run data may be retrieved form the cloud server later by the user and displayed on the user smartphone (for example during the travel on the lift), or in real-time on a remote computer. Furthermore, using the GPS coordinates, cloud server may superimpose said data on 3D map of the terrain, giving additional reference and meaning to the data.

Figure 14:
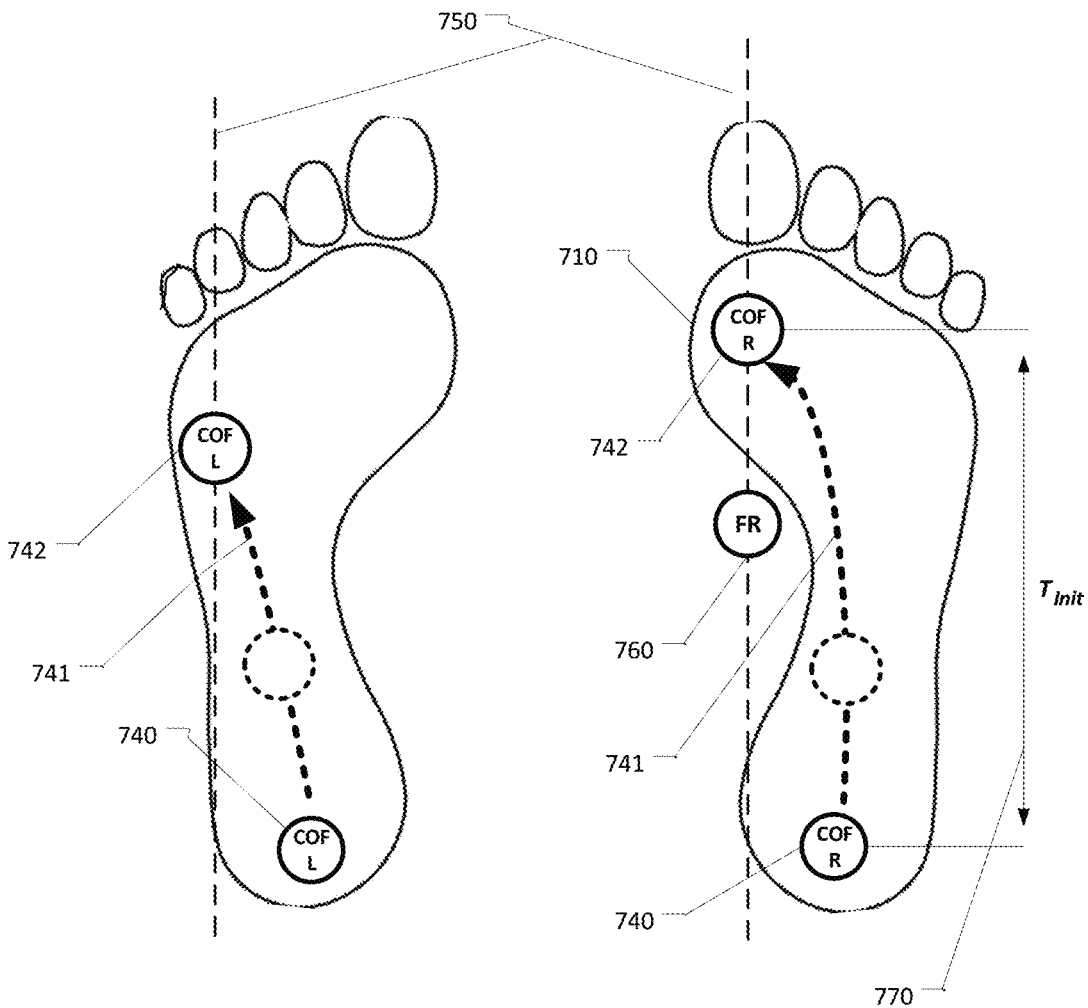
FIG. 14 shows a graphical and numerical representation of motion and pressure points transmitted to the ski-boot insole by the foot during a successful turn.

After the post-processing of first set of results by the remote cloud server, visual and numerical representation of the run can be displayed on a remote computer or on a smartphone. Among the others visual presentation possible, some of the visual options are presented in FIGS. 14, 15 a 16. FIG. 14, shows left and right foot with a graphical representation of the location of COF and 3D motion parameters in relation to the GPS time. Here we see the movement of the COF 740 from the start of transition into the left turn, the location of the COF 742 after the initial phase of the turn and the time (in milliseconds), of the transition 770. Furthermore, the calculated location of the resulting force $F_R$ 760, a point where the skier center of mass (COM) is acting on the ski and snow.

Figure 15:
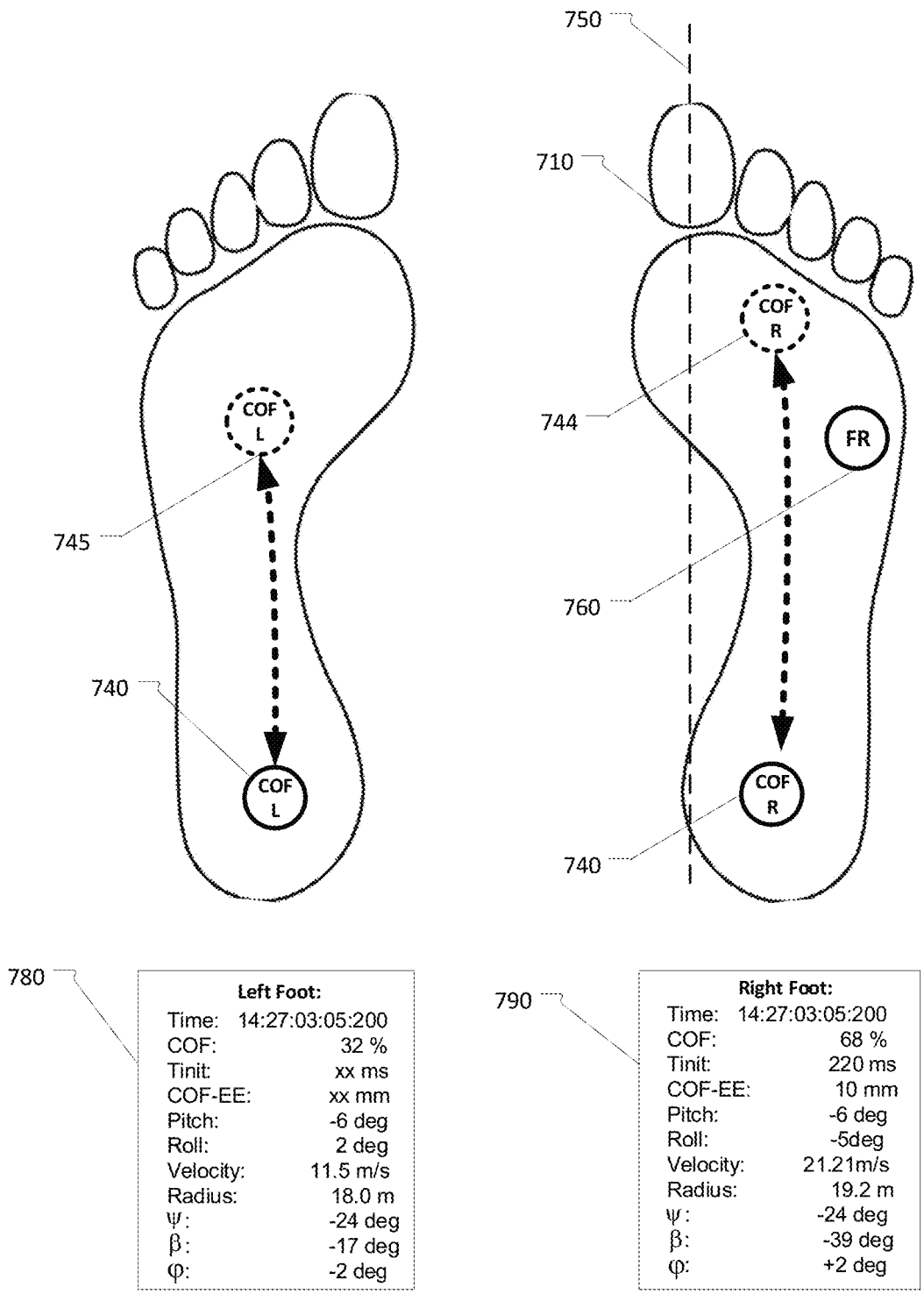
FIG. 15 shows a graphical and numerical representation of motion and pressure points transmitted to the ski-boot insole by the foot during an unsuccessful turn.

The graphical and numerical results, representing unsuccessful turn is presented in FIG. 15. Here we see the mistake user makes during the start of transition (flat ski⇒select new ski⇒COF of inner foot to head of $5^{th}$ MT), inner foot COF forward to the center of foot 744. In order to maintain balance, the COF of the outer foot was placed between $2^{nd}$ $3^{rd}$ MT 745, and the resulting force moved to the outer edge of the outer foot. In this position the body kinematics does not allow for pelvic rotation and in effect, the COF return to the heels of the feet—balance is lost, turn cannot be finished until balance is recovered during next flat ski.

Data are analyzed in relation to velocity, pitch and roll and effective radius of the turn and other numerical results 780 and 790 for left/right foot respectively, and may be used by both the amateurs to improve their skills, professionals during training, judges in analyzing performance of a free style or figure skating competition or even commentators during televised sports events. Furthermore, those results may be sorted and presented in various statistical formats selected by the viewer. An example of such statistical analysis may be use in training and evaluation of turn symmetry—one of most important parameter of measuring progress of a professional skier. Turn symmetry, is term used to describe a pressure applied during the left and right turn.

The closer is the distribution of pressures between inner/outer ski during the left and right turns, the better will the skier perform. Such analysis is currently limited to visual observation by the coach of the racer during a run over a specific part of the slope where the transversal angle of the slope maintains relatively constant angle to the line of the slope. Such observation is subjective, prone to errors and of limited value—as it's impossible to evaluate the symmetry of pressure visually and specifically on the slope with changing topographical parameters.

Turn symmetry statistics can be performed as follows:
Log all left turns into LEFT_SET, and all right turns into RIGHT SET;
FOR each turn with $\Phi_L=\Phi_R$ OR $-\Phi_L=+\Phi_R$ OR $+\Phi_L=-_R$ (roll);
Extract pressure points and force data;
Sort pressure points and force data in the descending order of difference.

Similar method may be used for numerous other parameters of the run.

Figure 16:
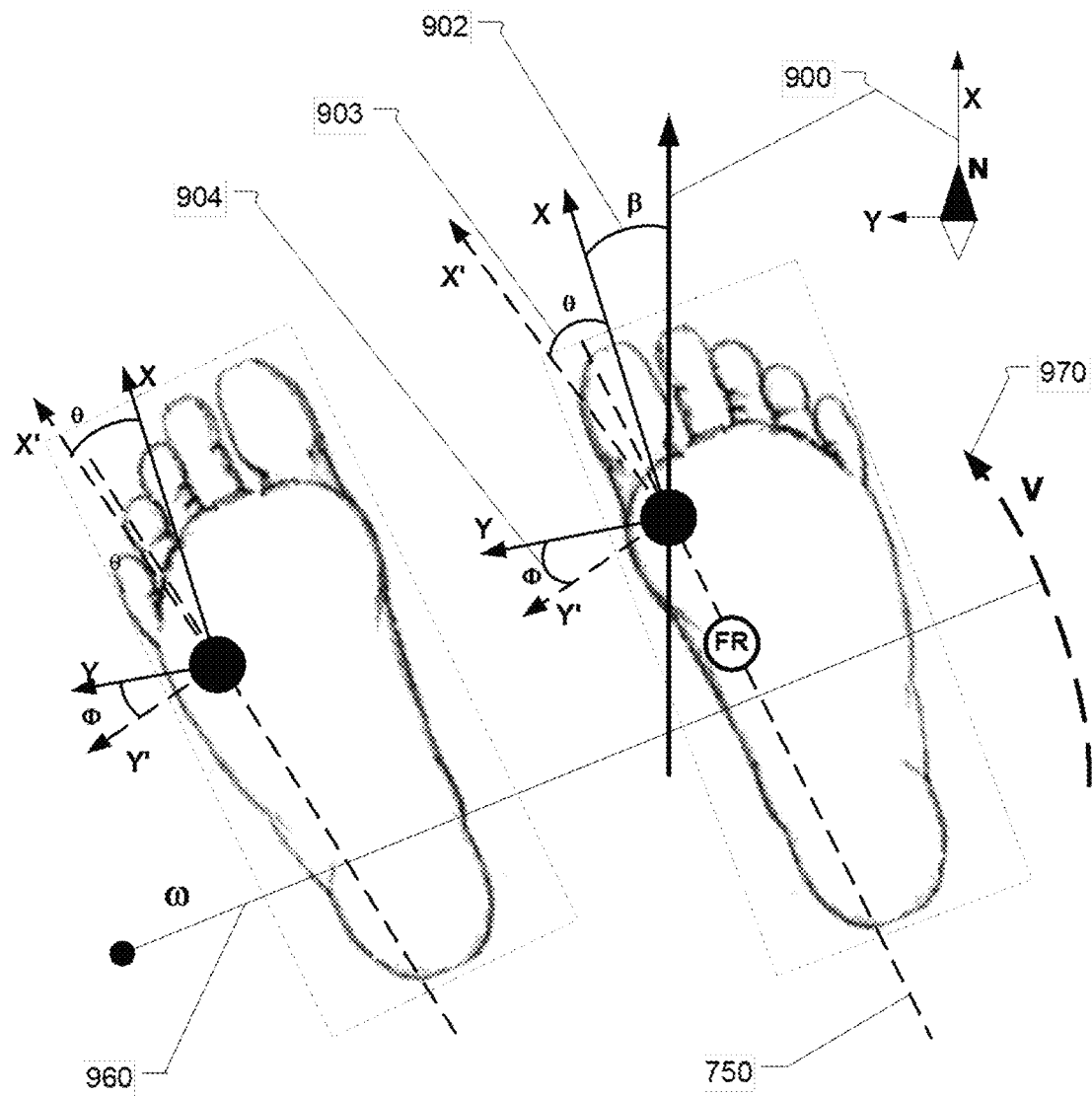
FIG. 16 shows another version of a graphical representation of motion in relation to the pressure points on the ski-boot insole.

Different view of the data presented in FIG. 16, where both feet are shown in relation to the global coordinate 900, the angle β, 902 to the local coordinate X, pitch Θ, 903, of the ski (angle between X and X)', the roll inside the turn Θ, 904, the effective turning radius w, 960, and velocity V 970. The location of resulting force $F_R$ in relation to the ski edge 750 is also presented.

Another application of skiing analyzer feedback system may employ direct control by an instructor of coach. Here, motion and force sensors data is relayed by the smartphone 200, to the remote device 700, operated by instructor or coach, who maintains visual contact with the user. On the device 700, data is processed by application 300, enhanced with a user interface (UI), allowing to manually control the haptic feedback actuator embedded in the user ski-boot insole. The input from the terminal 700, UI operated by instructor, is send back over wireless cellular interface 400 and 221, to the user smartphone 200 and then using the PAN wireless interface 210 to the haptic feedback actuator 1033, located in insole 100. Such embodiment allows the couch to directly influence the user actions and tailor his training/progress according to predefined plan or changing slope conditions.

Detailed Description of a Second Embodiment

Clinical gait analysis is extremely limited if it does not allow clinicians to choose between alternative possible interventions or to predict outcomes. While this can be achieved either by rigorously planned clinical trials or by using theoretical models, the results are generally poor due to the limited number of trials which can be completed in the clinical environment. One embodiment of the present invention has the potential of elevating deficiencies of the clinical trials (namely number of tested subjects). Current techniques for gait analysis rely on elaborate equipment in a laboratory setup—10 or more high speed cameras, recording subject motion using tens of markers attached to his feet and limbs. While the accuracy of such systems is determined by the accuracy of determining the marker positions due to the motion of soft tissue, a more important concern is the limited range of motion which can be recorded in a laboratory space and is difficult to reproduce. Gait analysis may be used for a wide range of applications—from selecting orthopedic inserts and analyzing athletic efficiency, to clinical rehabilitation. To aid in the rehabilitation process, in addition to analyzing the gait it is beneficial to provide real time feedback designed for gait correction.

The method provided by this embodiment measures a person's foot motion in relation to vertical and horizontal ground reaction forces (GRF). The method allows an analysis of the foot motion during activity performed by the foot, including, without limitation, walking motion, running motion (i.e., during a person's gait), etc. In one embodiment, this is accomplished by embedding a 3D motion processor configured to process motion and data received from a force sensor subsystem. The force sensor subsystem, in some embodiments, comprises: a 3-axis accelerometer sensor; a 3-axis gyroscope sensor; and a 3-axis magnetometer sensor; and a plurality of force sensors. In addition, in some embodiments, the system includes an embedded haptic actuator placed in a shoe insole which aids in providing feedback to correct the wearer's gait. The corrective, haptic stimulus is provided by post-processing of the results of analysis results. Motion prediction algorithms are used that are designed to minimize the difference between the current and desired gait pattern. In some embodiments, such corrective feedback may be designed as an aid in recovery from injury, to improve walking/running efficiency, or aid in the design of prophylactic and athletic footwear.

The system is configured to analyze gait and balance by estimating vertical ground reaction force vectors applied to the user feet and moments applied to the user's limbs in relation to foot motion. Furthermore, the system comprises motion prediction algorithms based on the user's kinematic model and the activity biomechanical model configured to provide haptic corrective feedback. In addition to motion, force and haptic elements, said embodiment comprises a wireless personal area network (PAN) transceiver—such as: Bluetooth, ANT, etc., used for transmission of force and motion data to the smartphone-based application and for reception of control signals intended for haptic feedback actuators. This haptic feedback is designed to instruct on the proper timing and the location the COP which needs to be applied during the next phase of the gait cycle. Furthermore, in some embodiments, the smartphone-based application is configured to transmit gait data and the user location coordinates to a remote location for remote analysis, post-processing and for storage using the cellular network connectivity of the smartphone.

For purposes of the present disclosure, in some embodiments and without limitation, a gait may be classified as the following activities performed by humans: walking, jogging, running, sprinting, etc., and other types of movement that carries a human body over a distance of ground. A gait cycle may defined as a time period or sequence of events or movements during locomotion (for example, walking, jogging or running) in which one of a user's foot contacts the ground to when that same foot once again contacts the ground, and involves propulsion of the COM in the direction of motion. A single gait cycle may also be referred to as a single "stride". During a walk (wherein a typically walking pace may be between 3.0 to 4.5 km·hr), a gait cycle comprises two phases: 1) Stance Phase; and 2) Swing Phase, with the respective duration of those two phases of 60% and 40% of the user gait cycle. Furthermore, each phase of the cycle can be further divided into portions consisting of double or single limb support. It is those portions of each phase of the gait cycle in most cases initiated when the heel strikes the ground and the toe is off the ground, followed by limb swings and terminates with single limb support when the supporting heel rises from the ground and continues until the opposite heel touches the ground. During a jog (typical jogging speed is between approximately 6.0 and 11.0 km/hr.), a run (typical running speed is between approximately 12-18 km/hr.) or a sprint (>20 km/hr.), as movement speed increases, a third phase develops. The third phase comprises a non-supporting of the body by the feet (as referred to as a "floating" phase). This third phase, or floating phase, develops during the movement wherein the stance phase portion decreases and the swing/float phase increases.

In some embodiments, the stance phase occurs when the heel bone is perpendicular to the ground, the ankle joint dorsiflexes (toes move toward shin) by approximately 10°, and the force is present at the heel of the foot. As such, start of the gait cycle is determined by simple observation of force vector measured by the force sensor located under the user heel and the y-axis of the Euler angle computed by the motion processor. If the F_heel is larger than a predefined threshold of normalized body weight obtained during calibration scaled by type of activity (approximately 80% for walk, 60% for jog, 40% for run and 30% for sprint), and the y-axis of the Euler angle is less than 5°—the cycle start time is recorded. From walking to sprinting, the third—nonsuppurative, float phase develops, during which the stance phase decreases significantly, does aiding in determination of user's activity. In some embodiments, this simple detection algorithm may be enhanced by adding thresholds on magnitude vectors of accelerometer x and y axis and comparing the peak g-force value (shock), calculated from measurements provided by the accelerometer as: $|x^2|+|y^2|+|z^2|-1$. Similarly, all other phases of the cycle can be determined by observation of Euler Angles provided by the motion processor and vectors obtained from a plurality of force sensors located under the user's POB and the time and location of GRF. Furthermore, the location of the COM may be approximated from the user's physical characteristics (weight, height), the location of the user's foot COP is obtained by weighting force vectors recorded at the foot POB in 2D Euclidean space. Then the distribution of force between the user's left and right foot is easily calculated which now then can be used to calculate the COM in 3D Euclidean space. A more advanced and accurate location of COM may be obtained using the user's body kinematic model, obtained from the user's physical and physiological information and natural pronation obtained during calibration. All of these techniques are described in greater detail below and in the paragraphs below.

Past and current locations of the COP and the user foot motion in 3-dimensional space obtained by calculating Quaternion of the motion vectors allows for prediction of foot movement during the next gait phase or even next gait cycle. While the phase of the gait is established from timing and the location of GRF, the future motion may be predicted from the past motion vectors recorded in the previous gait phase (i.e., the past foot trajectory), and an estimation of subsequent motion vectors based on the current motion vectors and the location of the COP. When the corrective feedback is employed such information, together with the user's kinematic model and calibration data, is applied to a recursive filter designed to minimize a difference between received motion vectors and a desired motion vector to provide feedback advice in the form of haptic stimulus. The haptic stimulus instructs on the proper time and location of the COP during the subsequent gait phase.

Figure 1B:
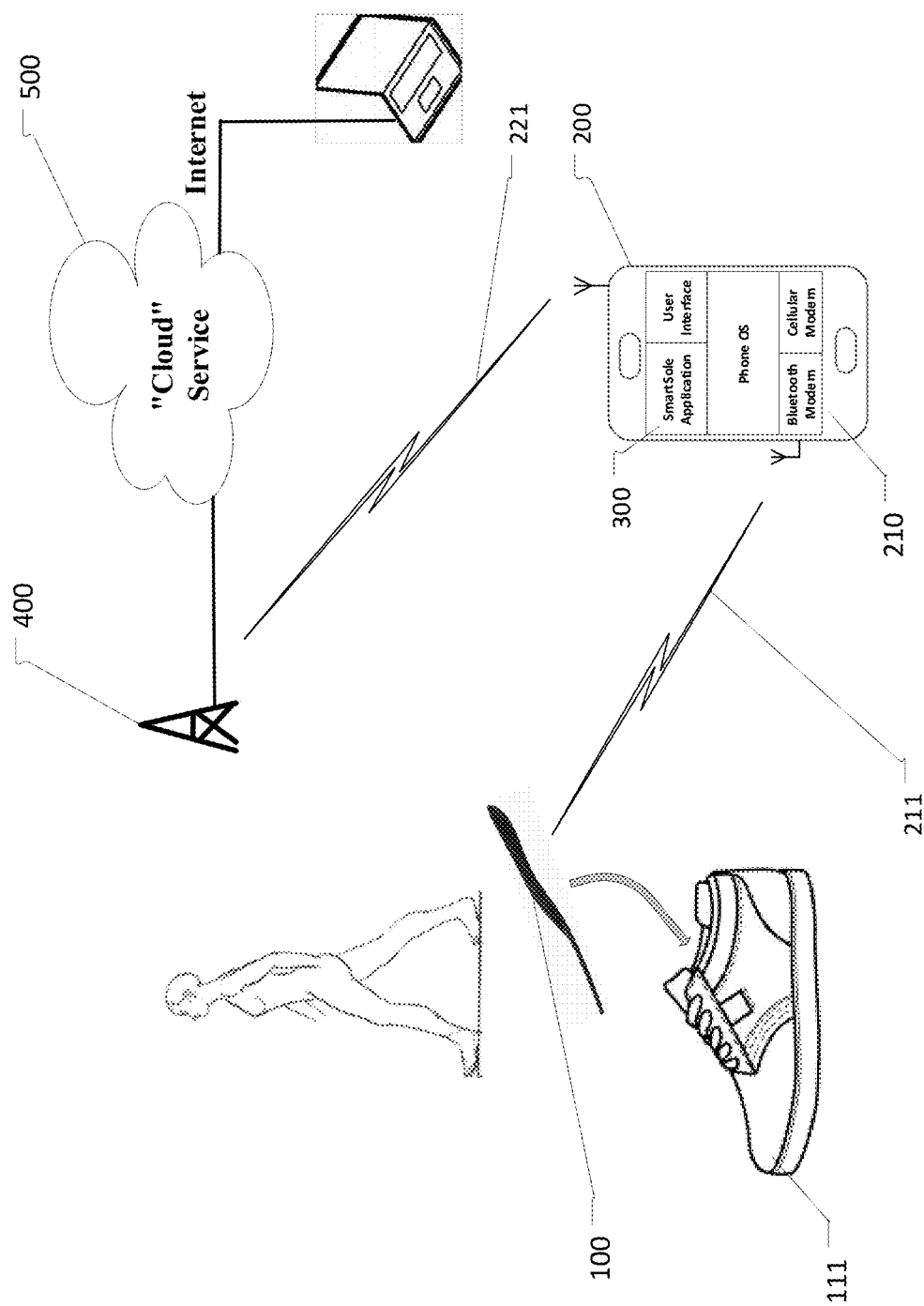
FIG. 1B shows an exemplary gait analysis haptic feedback system.

The exemplary system is presented in FIG. 1B. Here an insole 100, of a shoe 111, communicates with a monitoring application 300, hosted in a smartphone 200. The monitoring application 300 pre-processes motion and pressure data, retrieves a GPS time and coordinates from the smartphone, and transmits this data using a smartphone cellular radio interface 221 in some embodiments, to the cloud service 500, for further post-processing. The pre-processed motion and pressure data are used to provide haptic feedback to the actuator positioned in the insole. Based on the GPS coordinates extracted from the data, a 3D map of the area may be superimposed on resultant graphical and numerical parameters displayed on a remote computer or on the user's smartphone.

The gait analysis insole 100, shown in FIGS. 2 and FIG. 3, comprises a lower insole surface 101, and an upper insole surface 102. As shown in detail in FIG. 3, a motion and force processing sub-system and a feedback sub-system 103 is sandwiched between the insole surfaces 101, 102. In the embodiments shown in FIGS. 3 and 4, the motion and force processing sub-system, as shown in FIG. 4, comprises a motion processing element 1031, configured to perform specific motion fusion algorithms, at least three force sensors 1032, positioned under the user's foot $1^{st}$ Metatarsal, $5^{th}$ Metatarsal and the heel (foo POB), and at least one haptic actuator 1033, positioned under the user's big toe. In addition, a Bluetooth RF transceiver 1036 is included to provide bi-directional communication with a smartphone based analysis application and a microprocessor 1034, and its program memory 1035 providing control of the system. The motion processing element 1031, is configured to sample data at the rate specified by the microprocessor, wherein the data is sampled from: a 3-axis gyroscope sensor; a 3-axis accelerometer sensor; and a 3-axis magnetometer sensor (compass); and after appropriate filtering calculates: g-force, linear and angular acceleration, Euler Angles and the motion Quaternion. The results are transmitted to the microprocessor 1034 using one of appropriate digital interfaces, such as I2C, for example. At the specific sample rate, the microprocessor successively samples all force sensors connected to analog-to-digital (ADC) converter inputs. At the end of the sampling period, the microprocessor assembles motion information (for example, g-force, acceleration, Euler Angles and Quaternion information) and force vectors from all of the force sensors into a data packet. After appropriate encapsulation with packet control information the microprocessor communicates the packet to the Bluetooth interface for transmission to the smartphone based analysis application. Additionally, when the microprocessor receives a control packet from the smartphone based analysis application which contains control information intended to provide corrective feedback, it translates such control information to an appropriate code word and transmits this code word to the digital-to-analog (DAC) converter to stimulate the haptic actuator with a signal the amplitude and frequency of the signal correlating with the specific haptic instruction.

The motion processor obtains the user feet motion by observation of the three-dimensional vectors of gravity, orientation and azimuth. The sample of gravity and orientation vectors determine current orientation of user feet motion in a specific time period. To obtain foot motion, the Euler Angles are first calculated from gyroscope x/y/x vectors. This angular rate is converted to a quaternion representation as:

$$dq(t)/dt = \tfrac{1}{2}\omega(t)*q(t),$$

where ω(t) is the angular rate of motion and q(t) represents normalized quaternion. Then, we convert the accelerometer x/y/z vectors from local coordinate system, represented as $A_L$ to global coordinate system, represented as $A_G$, using previously obtained quaternion as:

$$A_G(t) = q(t)*A_L(t) + q(t)'.$$

Then we calculate acceleration quaternion as:

$$qf(t) = [A_{Gy}(t) - A_{Gz}(t) 0]*\text{gain}$$

and add the acceleration quaternion as a feedback term to the gyroscope quaternion, followed with addition of magnetometer data to the azimuth component.

Figure 20A:
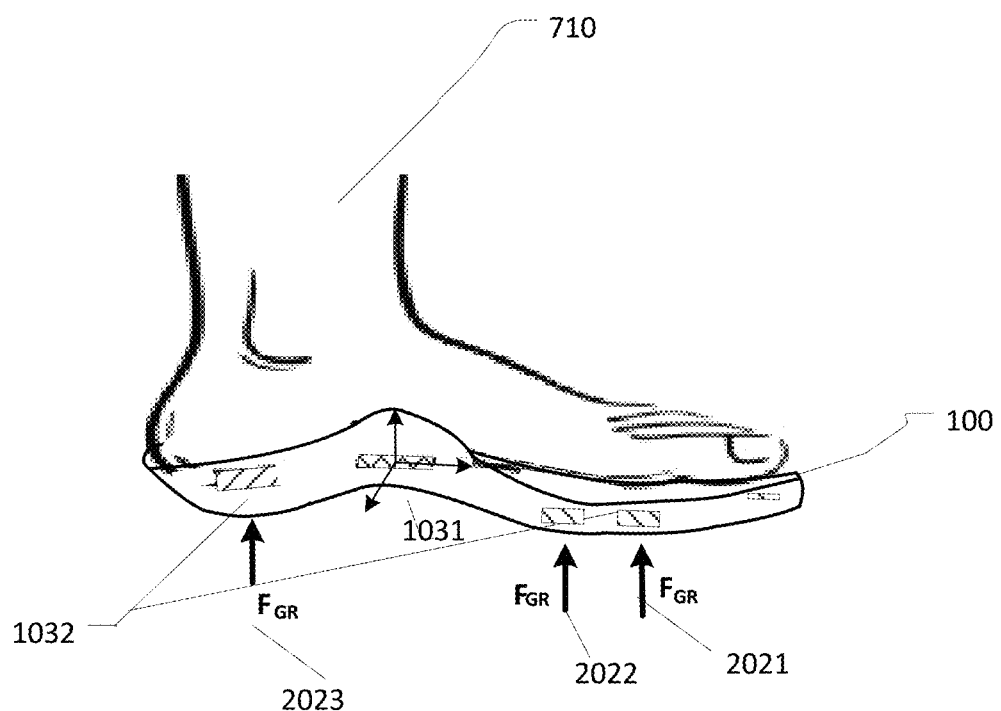
FIG. 20A shows an insole configured for gait analysis comprising motion and force elements configured to record and process motion and GRF vectors.

The relationship between ground force and a user foot 710, is presented in FIG. 20A. Here, the insole 100, comprising motion processing element 1031, and force sensing elements 1032 records the force vectors present at $1^{st}$ Metatarsal ($1^{st}$MT) 2021, $5^{th}$ Metatarsal ($5^{th}$MT) 2022, and the $F_{HEEL}$ 2023, in relation to the time and orientation of the 3-dimensional space (quaternion) of the foot.

Figure 18:
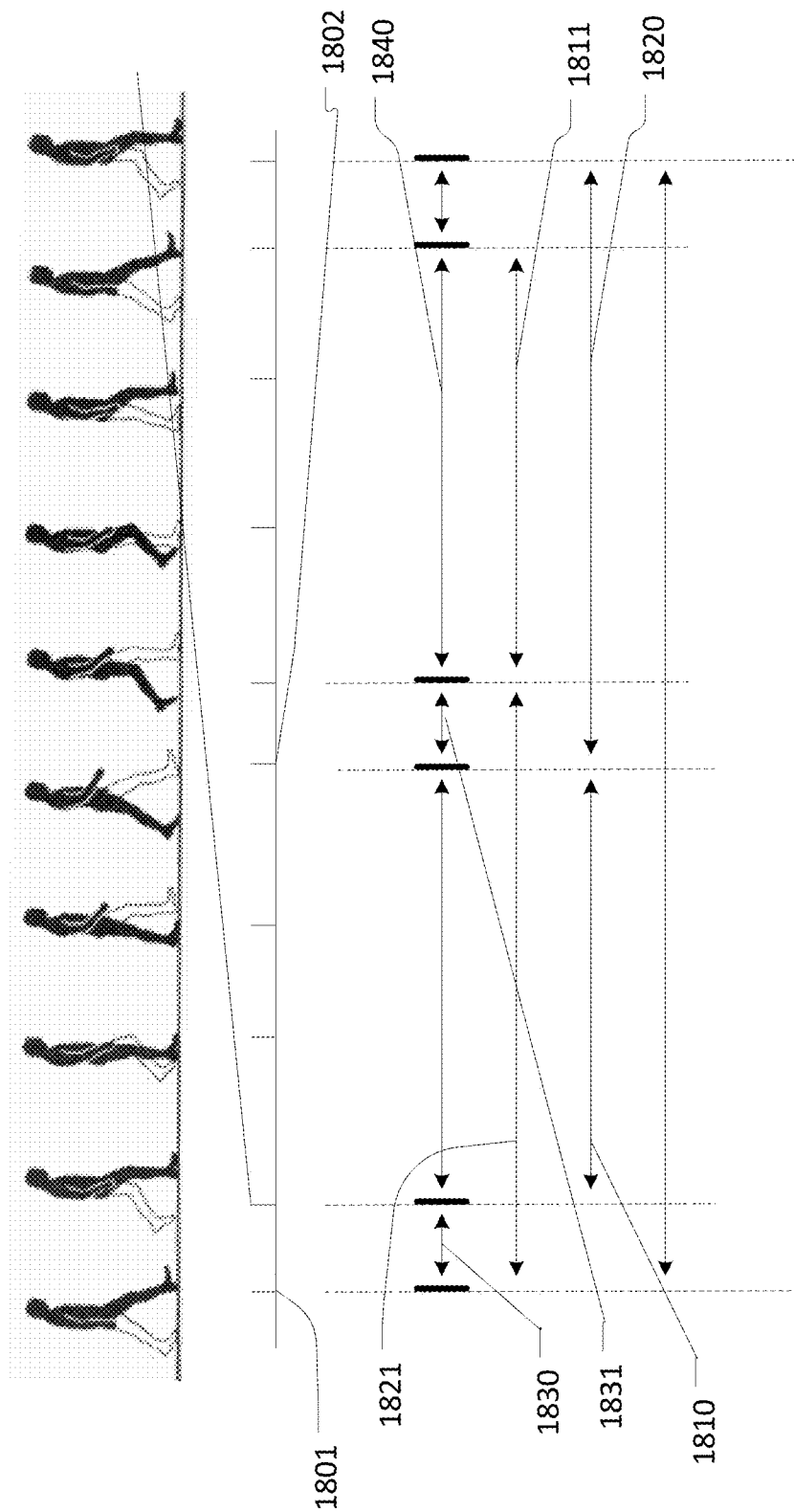
FIG. 18 shows a typical cycle of the gait in relation to timing of cycle phases.

A process of walking or running is presented in FIG. 18. As the body moves forward, one limb typically provides support while the other limb is advanced in preparation for its role as the support limb. The gait cycle 1800, is comprised of stance phase 1821, and swing phase 1811. The stance phase further is subdivided into 3 segments: 1) initial double stance 1830; 2) single limb stance; and 3) terminal double limb stance 1831. Each of double stance phases accounts for approximately 10% of the gait cycle, while the single stance typically represents about 60% of the total gait cycle, and the swing phase the remainder of the gait cycle. During the double stance period the two limbs do not typically share the load of the user and slight variations occur in the percentage of stance and swing in relation to velocity with each aspect of stance decreasing as walking velocity increases. The transition from walking to running is marked by an elimination of double support periods. In a normal gait cycle the two steps comprising the cycle are roughly symmetric.

During walk or run, each stride contains eight relevant phases, a single cycle of such stride or gait cycle 1800, is shown in FIG. 18. Of those eight phases, five are allocated to a stance (i.e. initial contact, loading response, mid stance, terminal stance, pre-swing), 1820 and 1821 for the left and the right foot respectively, with the remaining 3 phases are allocated to a swing 1810 and 1811 for the left and the right foot, respectively. The first two gait phases occur during initial double support 1830 and include the initial contact with the ground and the ground loading response. In the normal gait, the initial contact is referred as a heel strike 1801, and 1802, for the right and the left foot, respectively. Also, many patients recovering from injuries, or with a gait pathology, achieve heel contact later in the cycle, or not at all. Two phases located between the double support phases are referred as a single support phase 1840, 1841, for the left 1840 and right foot 1841, respectively. The joint motion during the double support phase allows transfer of weight from one to anther leg while attenuating shock, preserving gait velocity, and maintaining balance.

The swing phase corresponds to a single support of the limb currently supporting body weight consisting of a first half with a single support (and termed "mid-stance"). This is responsible for progression of the center of mass over the support foot and includes heel rise of the support foot and terminates with ground contact of the other foot. The final stance element—pre-swing—is related functionally to the swing phase that follows and begins with terminal double support and ends with the toe-off of the limb.

The gait analysis is performed in reference to motion and force vectors graphically presented in FIG. 20A and obtained during calibration. Here the user stands in a natural position with the weight equally distributed between left foot 710 and right foot (not show for clarity) is placed on left insole 100. The motion processing element 1031 records orientation vectors, while force sensors 2021, 2022 and 2223 record approximately ½ of the force produced by the user's body weight. The analysis process is presented in FIGS. 20B, 21A and 21B. In the terminal phase of the gait cycle presented in FIG. 20B—the toes are on the ground, while the heel is during the lift time. Here, the force sensors located under the foot point of balance POB ($1^{st}$MT, $5^{th}$MT, and heel—carrying almost 100% of user's body weight), to record the magnitude of the vertical component of the GRF 2021, 2022 and 2023, present at those location at this specific sample of time in relation to z-axis of the local coordinate system provided by the Euler Angles obtained from the motion processing element 1031 and pointing to the location of user's COM. This is further described in relation to FIG. 21A, where x, and z vector of the current foot orientation obtained by the motion processing element 1031, are used to derive the actual direction of the force vectors present at the $1^{st}$MT 2021, $5^{th}$MT 2022 and the heel 2023, in relation to the insole local coordinates 2035. The location of foot COP 2040, in FIG. 21B, as an average in the 2D Euclidean space, obtained using principle of Cartesian geometry—and as such not necessary indicative of the location of maximum force, wherein the magnitude of the resultant GRF vector 2042. is calculated as:

$$F_{GRF} = (F_{1MT} + F_{5MT} + F_{HEEl})$$

The direction of the resultant GRF vector can be obtained by multiplying each of the individual force vector be the cos of an angle obtained from Euler Angle z-axis component. The direction (angle) of the resultant GRF vector indicates how the GRF influences the joints and how the vector magnitude is transmitted by the muscles through the tendons across the joints. The angle between the z-axis of a global coordinate system, and the GRF vector 2041, causes torque, which is caused by coupling effects of the forces present at the POB about the insole vertical axis and depends on the user natural pronation and body rotation. The torque is a product of three components of GRF-$F_x$, $F_y$ and $F_z$, acting along the x, y and z axis, with $F_x$, acting along direction of the motion, and both the horizontal component of GRR-$F_x$, and the lateral component of the GRF-$F_y$ are contributing to a friction (shear) force. During walk, the peak magnitude of the vertical component of GRF about 120% of the user's body weight, and about 180% during a jog, and as much as 275% during run. The shear forces during a walk and jog are similar with the magnitude about 30% to 35% of the user's body weight, and as high as 45% during a run. While the vertical component of GRG can be substantially absorbed by the cushion provided by the footwear sole and insoles, the lateral component (shear forces), substantial, difficult to absorb and at the same time a significant component of fatigue, injuries and detrimental to the foot health. Understanding of shear forces is very important for athletes: at some distance, the foot of a runner will exhibit larger inversion which increases the shear force; a basketball player who performs short lateral shuffling and 45° sidestep cutting may develop calluses due to the friction of foot against the footwear soles. As such, analyzing of complex GRF in 3D space provides potential to avoid many foot injuries by alerting the user when such forces exceeds predefined safety threshold or when a repetitive force may lead to a stress in the specific foot area.

Many user specific parameters, must be considered in gait analysis. Exemplary parameters include for example: the user's weight and gender, which may be entered through the application User Interface (UI). Another parameter includes the user's gait pathological conditions, which may be obtained during self-calibration procedures. Other parameters, for example, include but are not limited to the following: the configuration of the terrain, the speed of movement, the atmospheric conditions, etc. These parameters may be collected in real time from the smartphone GPS receiver and from the plurality of sensors.

User specific parameters comprise several different types of information, such as, for example: 1) physical and physiological information; 2) pathological information; and 3) natural gait information.

Figure 22A:
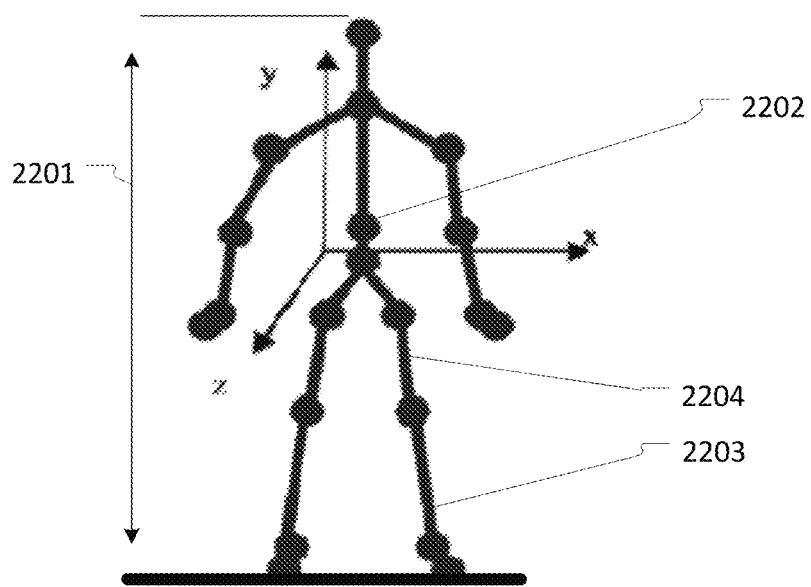
FIG. 22A shows a simple N-joint rigid kinematic skeleton model of the user limbs with each vertex representing a joint.
Figure 22B:
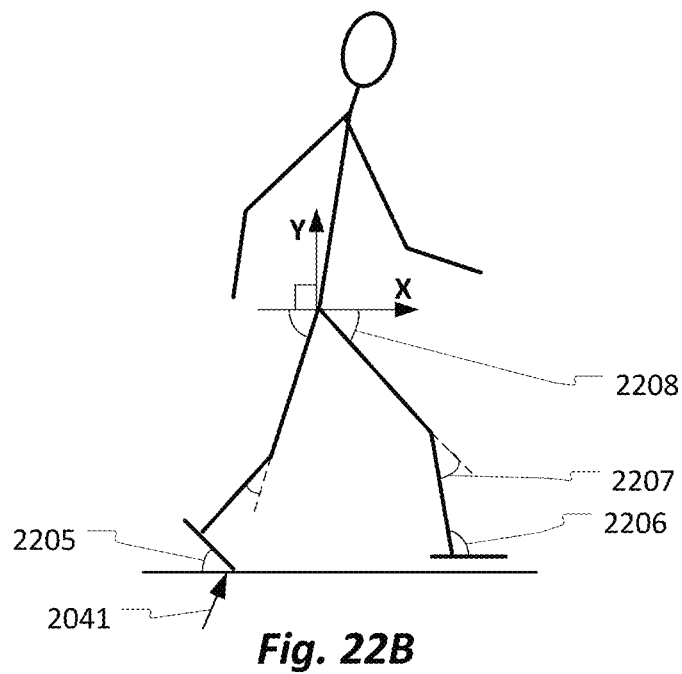
FIG. 22B shows a dynamic kinematic model of the subject walking.

The physical information comprises a description of user physical characteristics—sex (male/female); weight; height and a body-type, while the physiological information comprises information of the user's body characteristics—distance from hip to knee, and knee to ankle, etc. This information is used to build a kinematic model of the user's body and estimate the position of the user body's COM. The kinematic model may use a simple N-joint rigid kinematic skeleton model of the limbs and can be represented as a graph, where each vertex represents a joint. This model assumes joints with three degree of freedom for the hip and knee joints and a two degree of freedom joint at the ankle. The model is hierarchical requiring that all segments be defined. A static example of such a model is shown in FIG. 22A, and a dynamic model of the subject user walking is shown in FIG. 22B. Referring now to FIG. 22A, information about the user's height 2201, weight and body type comprised in a first information is used to estimate the position of the user's COM 2202. The distance between the knee and the ankle 2203, and between the knee and the hip 2204, etc. is used to build a model of the user's skeleton. The GRF acting on such static skeleton is assumed to be evenly distributed and ignoring short term weight-bearing inaccuracies between both feet is:

$$GRF_{Foot} = \text{Body\_Weight}/2[N].$$

The body kinematic model during a walk, as shown in FIG. 22B, is constructed from the same parameters augmented with the motion vectors obtained from the Euler Angles, quaternion, and the body velocity—is obtained either from GPS data or is calculated from acceleration vectors. The orientation of the user foot ankle joint is obtained from the rotation around the y-axis of Euler Angle 2205, and 2206 for the foot initiating and terminating cycle, respectively. Those angles together with x and y angles obtained from the motion processor, and with the plurality of force vectors recorded at the user's foot POB, completely describe the motion of the user's foot. When the angles and forces are superimposed on the kinematic model, they can be used to calculate the magnitude of moment applied different joints as:

$$M = d * F * \sin\theta$$

The action of GRF 2041 at the point of initial contact, is transmitted as the moment of torque to different joints and the moments caused by this force depend on the force magnitude which is proportional to the user's body weight, acceleration, the length of each of the body segments, and the orientation of the feet during contact with the ground. The distance of the projection of the ground reaction force vector from a joint center of pressure is taken as a measure of the moment or torque acting about a lower limb joint. The orientation of the left foot 2205, and the right foot 2206, foot is obtained from Euler Angles provided by the motion processing element while angles between the femur and the tibia 2207, and the femur and the hip 2208, for the left foot and the right foot, respectively, can be calculated using Pythagorean Theorem from the information 2203 and 2204.

Another information, comprising description user pathological characteristics—such as, for example, trauma/injuries, muscular abnormalities may be added, while the information of the user's normal, abnormal or pathological gait is obtained by the system during natural pronation calibration procedures.

For the purpose of gait analysis only, the calibration of the user natural pronation is performed in two separate phases, while if the corrective option is required, an additional third phase. In accordance with this embodiment, a first phase is performed. During this first phase, the insoles orientation within specific user shoes is calibrated to accommodate for a different type of footwear (walking, running shoes, different inclination, tilt, etc.). This procedure is performed by placing shoes with inserted insoles on a leveled surface parallel to each other, to obtain the relation between local coordinate system (vectors of accelerometer, gyroscope and magnetometer reported by the motion processing element embedded in the insoles), and the global coordinate system (absolute orientation in relation to the earth magnetic field). Results of this procedure are recorded, then used as an offset during analysis to provide the real orientation of feet in relation to the earth. One can visualize this by assuming that the heel of the shoe is much higher than the toes—let say $2°$ for left and $7°$ for right. If these local coordinates are used for analysis, a constant error is observed, and the analysis would be quite useless. In order to avoid such errors, this offset is subtracted from each received sample. The second phase of calibration intended to obtain the user natural pronation is performed by the user stepping inside the shoes and standing in the user's natural position. At this step, the analyzer obtains orientation of the user's feet and records the difference between orientation (Euler Angles) obtained during the first phase vs. orientation obtained during the second phase. This difference, is equivalent to the natural orientation of the user's feet—natural pronation. Furthermore, during this second phase, the user's weight, the distribution of weight between left and right foot, and the distribution of pressure inside the shoes, is recorded and compared with the weight provided in the user's physical information.

Figure 23A:
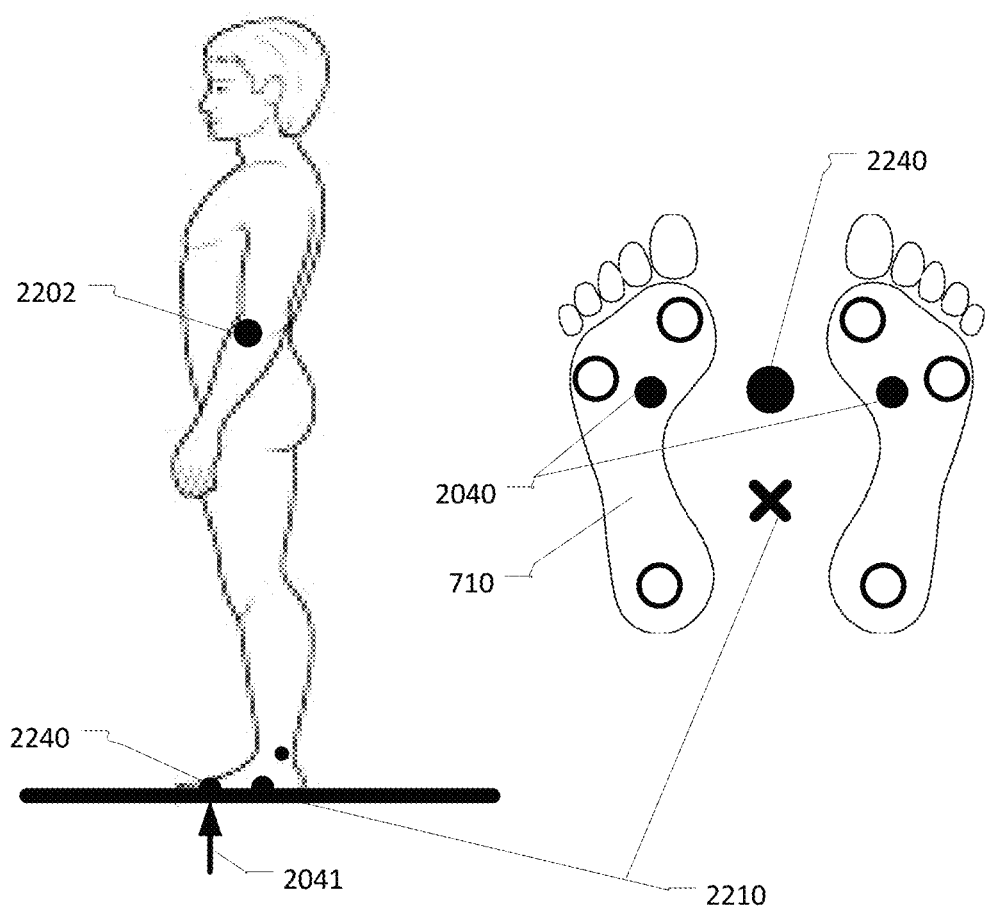
FIG. 23A shows users natural position and location of COP and COM during exemplary calibration process.
Figure 23B:
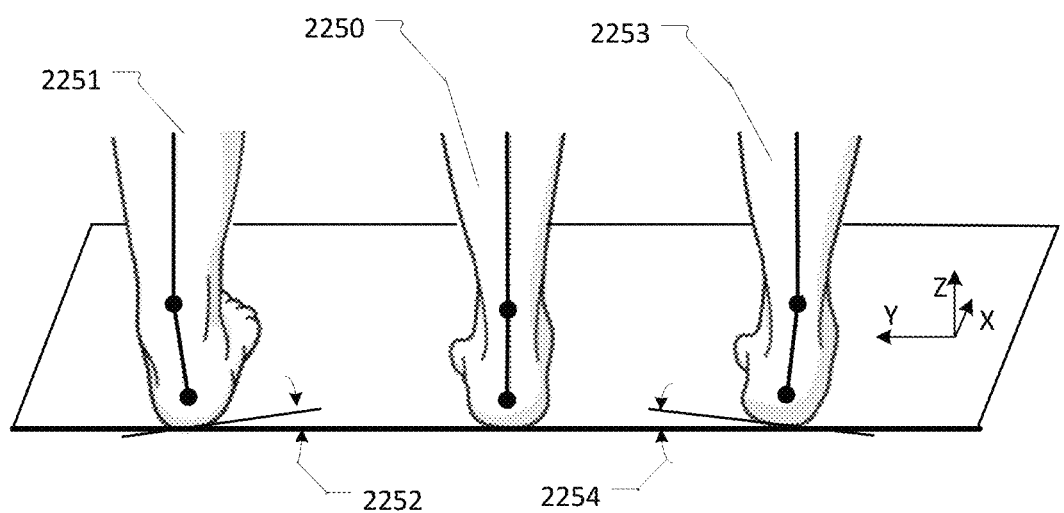
FIG. 23B shows an exemplary method to obtain natural pronation (overpronation, neutral, supination), through calibration process by recording Euler Angles and the magnitude and distribution of GRF.

The calibration procedure for a person with neutral pronation is shown in FIGS. 23A and 23B. As shown in FIG. 23A, the user stands in a natural position with weight equally distributed between both feet. The vertical GRF 2041 is also evenly distributed with feet COP 2040, positioned between the $2^{nd}$ and $3^{rd}$ Metatarsal of the user's feet and arch of each foot 710, while the body COP 2240, is positioned between the feet and the user's center of weight 2210, positioned below the COM 2202. The natural pronation is shown in FIG. 23B—neutral 2250, overpronation 2251 and supination 2253, is obtained by recording the direction of rotation along the x-axis either from the Euler Angles or directly from the gyroscope, where the rotation in a negative direction 2252 indicates overpronation and rotation in a positive direction 2254, indicates supination. The severity of the up-normal pronation is obtained by the magnitude of the angle and by the distribution of GRF recorded by the force sensors located under the foot POB.

The natural gait parameters obtained during the second phase of calibration process, provide verification of the user's actual weight versus the weight comprised in the user physical information. The difference between the user's gait natural pronation and the desired gait is used as a coefficient in a filter designed to correct the user's gait. In some embodiments, such a filter may comprise a Least Mean Squares (LMS), a Kalman filter, or a Gradient algorithm or another appropriate filter, which is designed to minimize the difference between the current gait and the optimal gait. In the case of rehabilitation after injury, it may be desired to control the process of correction. In such cases, the coefficient may be modified through a parameter entered using the analyzer UI allowing faster or slower adaptation/convergence. The output of such a filter is a control function applied at the specific phase of the gait cycle as a code-word to the digital-to-analog (DAC) converter which stimulates the haptic actuators located in the insoles. This stimulus may be in the form of haptic pulses of various amplitudes and frequencies specifically designed to provide information in which direction the COP should move and at which specific times. For example, a high frequency amplitude pulses start by the fraction of time before the COP should be moved to the $1^{st}$ MT, then with time progressing, the frequency is lower, and the pulses stop when the COP is detected in the desired position. The time of such advance instruction is derived from the user's velocity, current orientation of the foot provided by the quaternion function and information from prior gait cycles. Such a vibrating actuator may be located in a specific place inside the shoe insole. For example, the vibrating actuator may be located under the user's big toe, or a multiplicity of such actuators can be located in designated areas of the insoles as deemed necessary and appropriate.

During the third calibration phase, a dynamic data of the activity intended to be analyzed/corrected is performed. In this phase, the user is instructed to record the user's normal activity, such as walking, running, etc. The motion and force data is recorded together with the location coordinates and stored as a user reference model. Furthermore, if the recording spans a long period of time and over different terrain configurations, the recorded samples are classified according to the terrain coordinates and stored as a separately profile. This dynamic model contains such parameters as: velocity and activity type; stride time, value, location and timing of GRF; and the motion vectors. Based on the type of activity and timing obtained from the force sensors, the analyzer estimates the duration of each phase of the gait cycle, those establishing the gait cycle window. Then averages of each type of data (motion, force) are calculated, within such gait cycle window and over the entire set of data collected during this calibration phase. In case the associate location data indicates different terrain (i.e. uphill/down-hill), the model is further classified and stored separately.

Figure 24A:
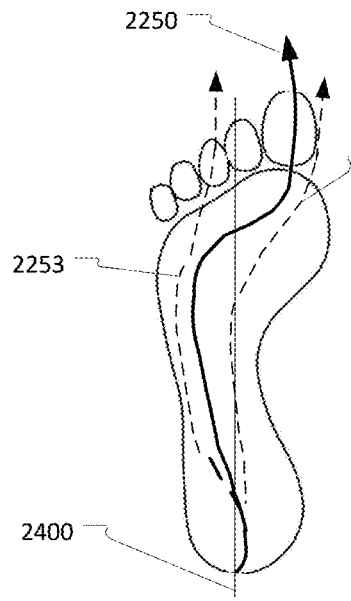
FIG. 24A shows the process of obtaining current phase of the gait and gait parameters by observation of location and trajectory of COP.
Figure 24B:
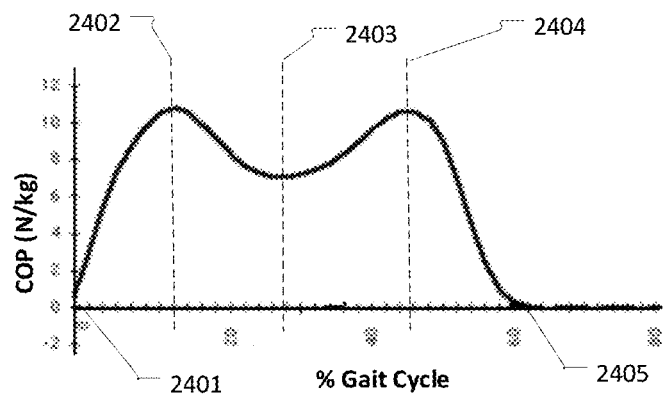
FIG. 24B shows a process of determining precise time each of the gait phase starts/ends by observation of location and magnitude of COP in relation to time.

The process of tracking the current position of the COP is shown in FIGS. 24A and 24B. In FIG. 24A, it can be observed how the COP progresses in time from the initial contact when COP is positioned at the heel, through terminal stance, when the COP is positioned under the toe as the foot of person with neutral pronation 2250, and will be positioned outside the toe toward the other foot for a person with overpronation 2251, as his foot will rotate away from the foot midline, and will be positioned between the $2^{nd}$ and $4^{th}$ MT for person with supination, as his foot rotates toward the midline. It can also be observed how the COP travels at the outside edge of the foot for a person exhibiting supination and on the inside of the foot for a person with overpronation. The exact timing of initial contact and terminal stance can be obtained by observation of the COP position. This process is visualized in the graph of FIG. 24B. Here, the gait cycles start after motion vectors indicate the end of a mid-swing. Referring now to the graph of FIG. 24B, when the heel force sensor registers touching of the ground 2401, the time of the sample indicates start of the gait cycle. At a time 2402, the GRF reaches a maximum, and the COP is firmly located over the heel indicating foot loading. As the GRF starts decaying, the COP moves to the center of the foot indicating timing of a mid-stance phase 2403. From now, the loading and the COP moves to the anterior part of the foot while the GRF begins to increase again indicating the terminal phase 2404. Now as the GRF decays, the toes lift off the ground 2405, indicating an end of terminal phase the end time of the gait cycle.

Figure 19A:
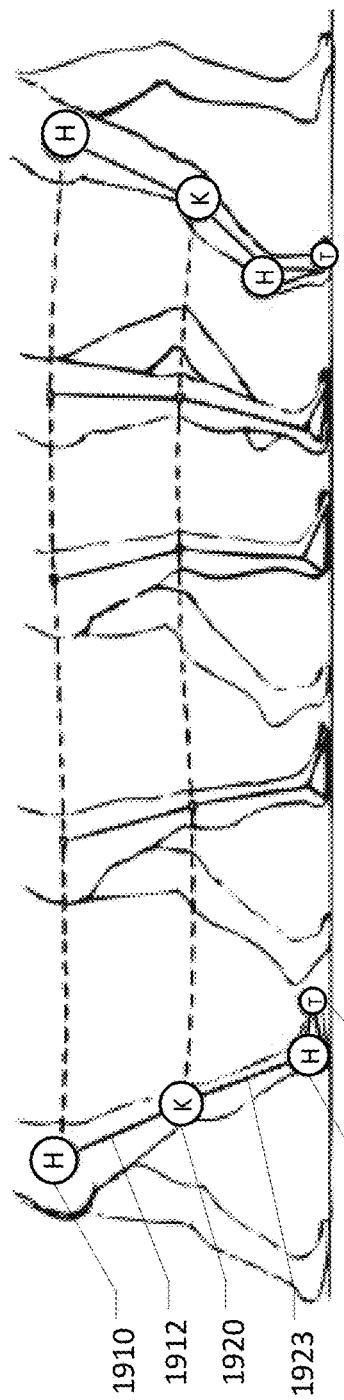
FIG. 19A shows a model used to analyze moments and forces applied to joints.
Figure 19B:
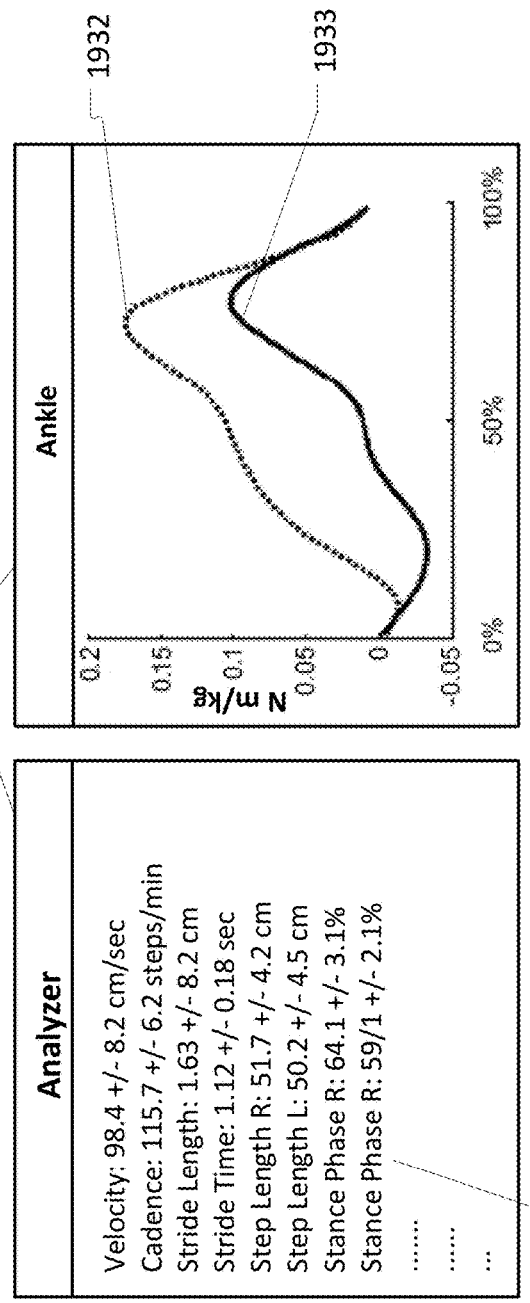
FIG. 19B shows an example of an analysis of ankle during the stride with numerical data and in graphical form during sampling time of the averaged gait cycle.
Figure 24C:
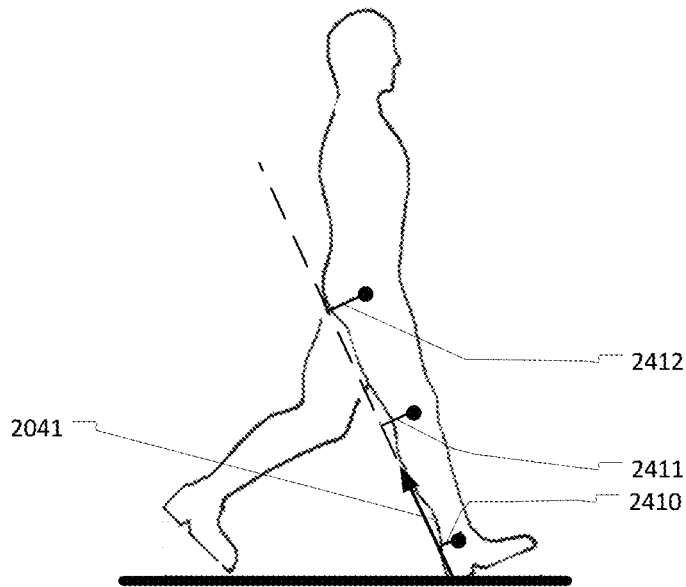
FIG. 24C shows a method used for prediction of moments applied to the user joints by observing the direction and magnitude of GRF.

The projection of GRF is used for prediction of internal joint moment. The distance of the projection from a relevant joint gives the magnitude of the joint moment. This allows for prediction of the net joint moment acting in dorsi-flexion of the ankle, extension at the knee and in flexion at the hip vector from a joint center. This is frequently taken as a measure of the moment or torque acting about the lower limb joint and is shown in FIG. 24C. Here the GRF 2041 vector passes through the COP of the foot to the knee and the hip joints and to the COM in form of external moment, and can be calculated using the distance from the joint center of the ankle 2410, knee 2411, and hip 2412 as:

$$|\vec{M}|=(GRF)*(\text{Perpendicular distance})$$

and each of the internal joint moments can be obtained from the magnitude of the GRF and the perpendicular distance from the projected vector to the respective joint center by computing the joint net moment from GRF and joint position in 3D Euclidian space as:

$$\vec{M}=\vec{r}_F*\vec{F}.$$

Where the GRF is obtained from the force sensor(s), the GRF vector direction is obtained from z-axis of Euler Angles, and the location of joints may be approximated using the user's kinematic model and the Euler Angles provided by the motion processor.
Results obtained during the dynamic gait analysis provides a full picture of the user gait in relation to GRF transferred to the user's feet. Those results provide an estimate of rotation moments in each individual joint and are used by the analyzer to calculate, and to communicate in the form of haptic feedback, the proper location of pressure the user must apply during the next gait cycle. An exemplary presentation of the position and the distribution of COF were described above in more detail and are shown in FIGS. 6A, 6B, 6C; 7A, 7B, 14 and 15. Also, the model of joints (hip 1910; knee 1920, heel 1930, and toe 1940) used to analyze moments and forces applied to joints is shown in FIG. 19A and described above with reference to this figure. Given the following information one may estimate the forces and rotation vectors present in each joint of the user: (1) knowledge of the user physical characteristics (gender, weight, height, body type contained in the first information); (2) the user's physiological characteristics (distance from hip to knee 1912, and knee to ankle 1923); (3) information regarding the location, value and distribution of ground reaction force on the user feet obtained from the force sensors; (4) the phase of the gait and timing obtained from the motion processing element; and (5) the location and terrain characteristics obtained from the smartphone GPS receiver.
The results obtained in such an analysis of gait may be presented in various formats, for example: numerical; graphical or statistical. An exemplary representation of these results is shown in FIGS. 19A and 19B. In this example, an analysis of the user's ankle 1930, during the stride with statistical numerical data 1931 is presented in graphical form, providing a presentation of load (force) to the right ankle 1932, and the right ankle 1933 at each sampling time of the averaged gait cycle. When the gait analyzer is present in the user's smartphone and is enabled, the phone Bluetooth establishes wireless communication with the left and right shoe insoles. At this time the analyzer associates the left and right insoles Bluetooth devices ID (such as the device UUID identification), and the user may enter (or download) all the user's information. The user may then perform calibration of the user's natural stance.

The motion and ground reaction force is applied to the user body model obtained from a second information (user physiological characteristics), using inertia navigation algorithms and geometrical triangulation, translating sensors kinematics to user body segments kinematics by measuring position (and timing) of center of force (COP), and a biomechanical model of foot/surface interface during gait cycle. The results may be uploaded to the remote computer server for further processing or display using the smartphone cellular radio interface.

The numerical results may be stored in CSV or XLS file formats, for example, and made available for visualization of the moments and forces superimposed over graphical representation of the human body and/or over terrain or 3-D maps generated from collected GPS, atmospheric pressure or other sensors data. Additionally, said stored data may be viewed in a wide range of statistical analysis tools in form of graphs, distribution functions, etc.

The gait analysis may be used in a wide range of applications, such as, for example, selecting orthopedic inserts and analyzing athlete efficiency, and for clinical rehabilitation. In this section we describe the process of analyzing and correcting gait as may be implemented in the rehabilitation process, while indicating, that such process may be easily extended to another activity by those of skill in the biomechanical and related arts.

It is well accepted that the typical reasons for performing gait analysis are: 1) to determine the severity of disease or injury; 2) to aid in selection of treatment; 3) to monitor a user's progress. To perform diagnostic functions, it is necessary for measurements to be able to distinguish between normal and abnormal patterns of movement and also between the characteristics of one disease entity and another. There are two aspects to this. The first aspect is having measurement systems capable of working to an adequate precision. The second aspect is a knowledge of what characterizes normal walking and what characterizes walking with a particular disorder.

Figure 29:
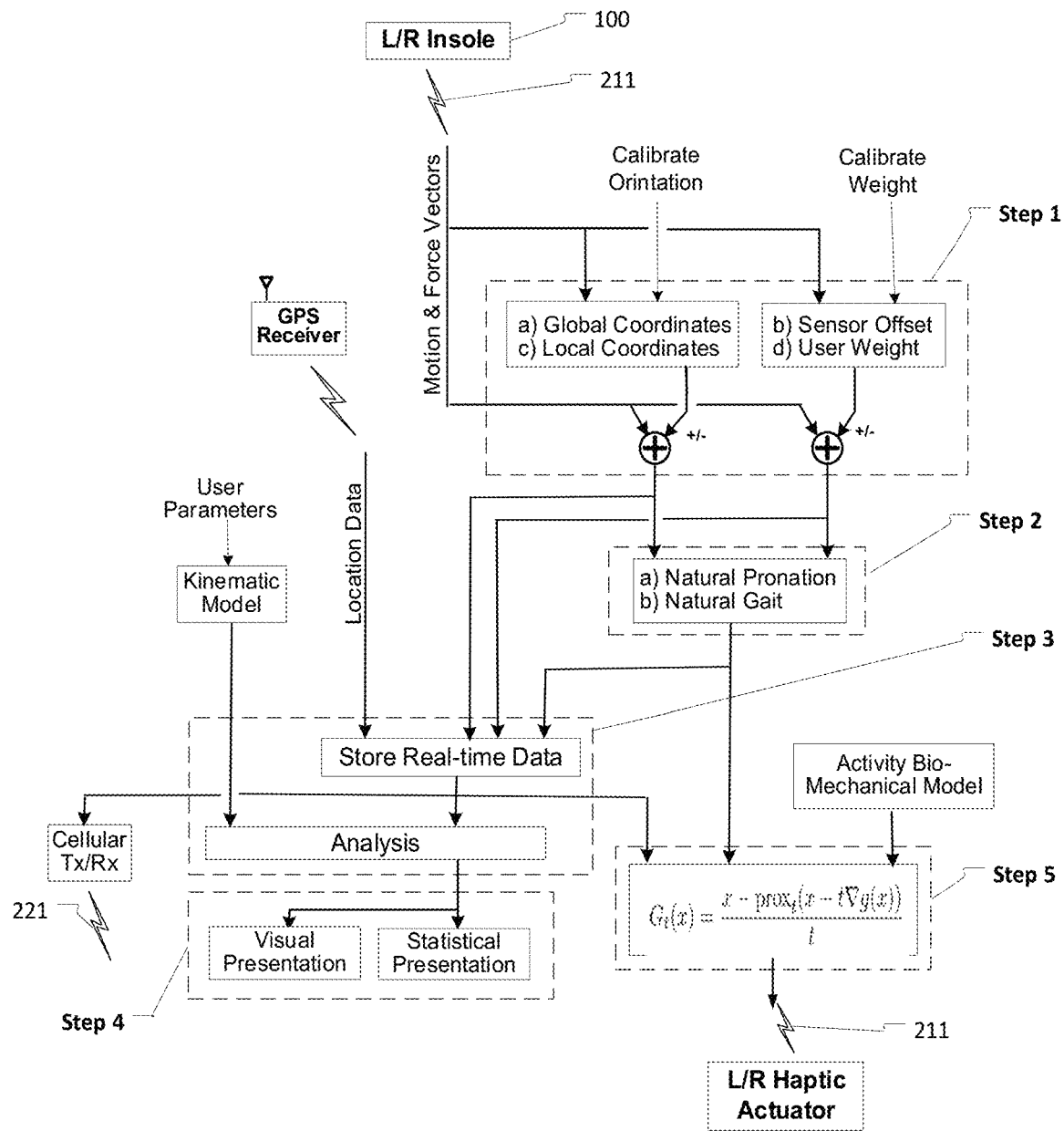
FIG. 29 shows a functional flowchart of a foot analysis system.

The functionality of this embodiment is shown in FIG. 29 in the form of a functional flowchart of the analyzer system. Step 1 is performed during a first phase of calibration, when left and right insole 100 are placed on a level surface and when motion and force processing elements are in communication with the analyzer using, in some embodiments, the Bluetooth wireless interface 211. In Step 1, samples of the x, y, and z axis of a magnetometer sensor embedded in the insoles re received by the analyzer which, after performing sufficient averaging of received vectors records, result as Global System Coordinates. The Global Coordinate System is used to determine relative orientation of the insoles and to correct for any gyroscope sensor drift. Samples of the plurality of force sensors, and x, y, and z axis of the accelerometer are received, averaged, and the results are stored as an offset between the expected value of respective axis and the actual value obtained from the respective axis of the respective sensor. For example, if the accelerometer is a perfect device, the value obtained from its x and y axis would be 0.00; 0.00. The value obtained from the accelerometer x-axis would, in most locations on Earth, approximate 0.98. Without any load, the force sensors should record a force of 0.0 Newtons. However, due to manufacturing tolerances, the actual values provided by each force will most likely be in range of ± several Newtons. The sensor calibration offsets are subtracted from each received sample of the respective sensor. The analyzer reads values of x, y, and z axis of the accelerometer and the gyroscope, calculates Euler angles of x, y, and z axis, and after sufficient averaging, stores the results as a Local Coordinate System of the insoles. Furthermore, the user weight is entered using an analyzer User Interface and the force sensors offset obtained during Step 1 is added/subtracted from the user calibrated weight.

In Step 2, the user's natural gait parameter, for example neutral; pronation; supination, etc., is obtained. The user is instructed to step into the user's footwear and the analyzer receives sample values from the x, y, and z axis 3 axis accelerometer, gyroscope sensors and from the plurality of force sensors. During static calibration of user natural gait pronation, Euler angles obtained in Step 1c are subtracted or added from or to each Euler angle calculated from the received gyroscope vectors. The received values/samples from each force sensor is subtracted from the respective calibrated weight of the respective sensor. The difference between the Euler angels provides information of the orientation of the user foot, while the difference between the force sensor readings provides information of the distribution of the associated forces. Together, these values provide information about the user's natural pronation.

In Step 3, in some embodiments, the real-time samples (corrected by the calibration values) and the GPS coordinates associated with the specific sample times is stored in the smartphone memory and analyzed according to criteria defined for a specific activity. If transmission to the remote location is enabled—data is transmitted using the smartphone cellular radio interface. In Step 4, the user may retrieve data, analyze data and present results in visual form, statistical form or in any form that is convenient to the user or anyone analyzing this information.

Corrective feedback is provided in Step 5. Here, the analyzer builds a model of the user's natural gait reference which, together with the activity biomechanical model (walk, run, etc.), is used to derive a corrective function if necessary. The corrective function is derived by minimizing the difference between the user's natural gait reference model and an activity optimal model. The user's natural gait model is obtained during natural gait dynamic calibration, which is performed by instructing the user to perform several gait cycles during which the analyzer records timing of each cycle and the portion of the cycle for the user's left and right foot. The results are sufficiently averaged to remove variations and stored as the natural gait model for use in the correction algorithm. This process is described below with reference to FIGS. 24A and 24B.

Referring now to FIG. 24A, the process of obtaining a natural gait model for a user with neutral pronation is depicted, however, after the user has suffered an injury of the user's right foot. Assume that the left foot COP progresses along path 2250. Also, assume that due to the injury to the user's foot, the user compensates the force on the right foot by placing most of the pressure to the foot on the inner part of the foot and in effect the right foot COP progresses along the 2253 path. While location of the COP is determined from the values of force recorded by force sensors located under the user POB using 2D Euclidean algebra, the phase and exact timing of each cycle is determined by observation of motion and data received from the plurality of force vectors.

FIG. 24B presents an exemplary method for the determination of gait cycle timing, where the curve represents normalized (to the user weight) value of vertical GRF sampled at 100/sec. rate, providing time resolution of 10 milliseconds. The gait cycle starts at the end of terminal swing phase—indicated by the motion vectors, and initiated with heel contact 2401, which is registered by the heel force sensor. The time of the heel strike is recorded as the start of the gait phase. At this time, the COP is located at the heel sensor, while $1^{st}$ MT and $5^{th}$ MT sensors record no force (except normal pressure in the footwear). When the GRF recorded by the heel sensor reaches a maximum, the beginning of the foot loading phase 2402 is recorded. With the gait progressing, the GRF is recorded by force sensors located under the $1^{st}$ MT and the $5^{th}$ MT, and the COP will migrate to the mid-foot 2403. This instance of time is recorded as the mid-stance phase. The heel is lifted, and the full of the GRF is located on $1^{st}$ MT and $5^{th}$ MT sensors and the time is recorded as the beginning of terminal stance 2404. Finally, when the $1^{st}$ MT and $5^{th}$ MT sensors indicate minimum GRF and the motion vector indicate that the toes are lifted, the end time of the gait cycle is recorded.

The dynamic calibration (obtaining of a natural gait model) process is performed as long as sufficient number of gait cycles is averaged. However, this does guarantee acceptable variance. In cases where the activity biomechanical model is intended for activities requiring optimization of dynamic forces, acceleration vectors from x, y, and z axis of the accelerometer are collected, and after subtracting the accelerometer offsets from each received sample, longitudinal and horizontal acceleration, and the g-force is calculated. This results in the natural gait model to be stored together with the activity specific (optimal) biomechanical model, and the results of real-time analysis may be used by a corrective feedback algorithm.

Figure 21A:
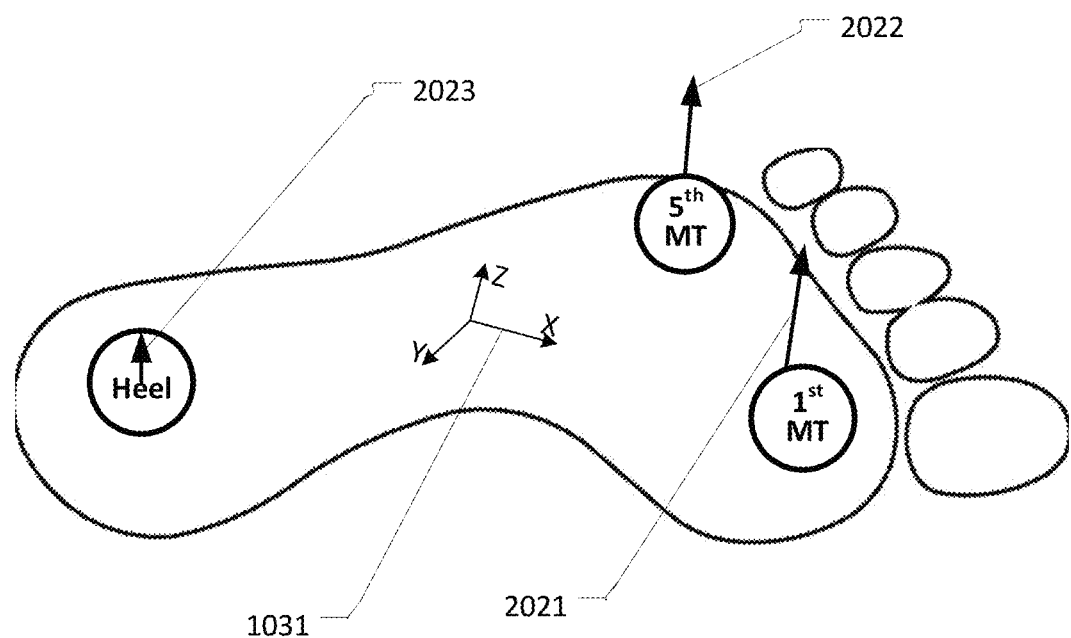
FIG. 21A shows GRF vectors present at the foot POB in relation to the orientation of the user foot.
Figure 21B:
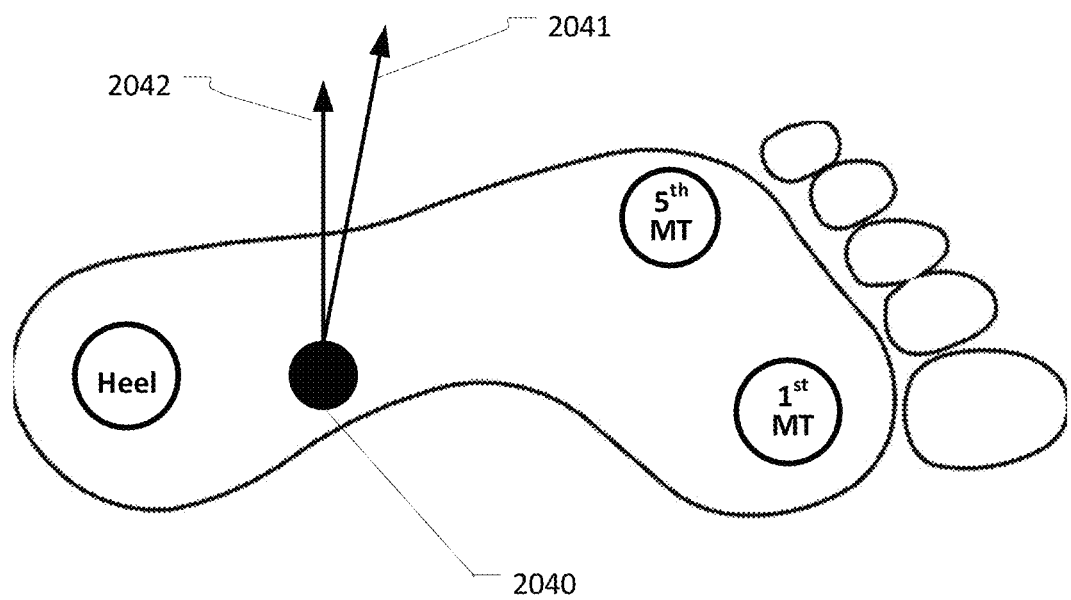
FIG. 21B shows location and direction COP vector obtained using principle of Cartesian geometry, and the magnitude of the resultant GRF vector.

After the system is calibrated, it may enter the real-time gait analysis state in Step 3. The processing is described in detail with reference to FIGS. 21A, 21B, 24A and 24B, and briefly again in this section. In some embodiments, motion and force vectors are continuously transmitted by the insoles 100 via the wireless radio interface 211 (FIGS. 1A and 2). The Local Coordinates obtained in Step 1 is subtracted from each received Euler angle resulting in a true orientation of the user's foot during this particular sample time. The Global Coordinates obtained in Step 1 are subtracted from the gyroscope data (after correction for drift), to provide a true azimuth of the user's foot during this particular sample time. Similarly, the received force sensor vectors are corrected by the sensor offset obtained during Step 1. Those vectors, and the user's location coordinates obtained from the smartphone GPS receiver, present a snap-shot of motion and GRF at this specific sample time as depicted in FIGS. 21A and 21B and at the specific geographical location. In some embodiments, the data is stored in the application memory for analysis and transmission to the remote server via the smartphone cellular radio interfaces 221 (FIG. 1A).

Figure 20B:
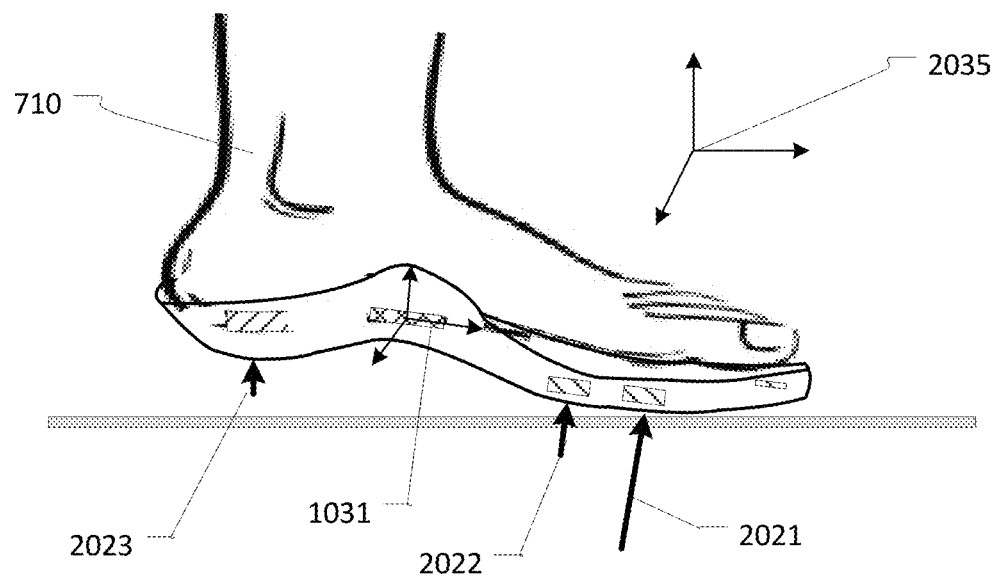
FIG. 20B shows orientation of the foot and insole in relation the GRF during the terminal phase of the gait cycle.

The analysis begins with a determination of timing of each phase of the gait cycle as described with reference to FIG. 24B. After the initial contact is detected by the force sensor located at the user's heel, the phase of the cycle is determined by relation between the foot orientation and GRF vectors. The trajectory of COP position is determined by calculating the position at the specific sample time in 2D Euclidean space, then integrating it over time while the foot is in contact with the ground, as shown in FIGS. 24A and 20B. The foot trajectory during the gait cycle is obtained by integrating the resultant motion vector of each sample of motion over the period of the gait cycle.

The user's kinematic model is constructed from the user information, as described in detail above with reference to FIG. 22A, is now applied to the activity model. This is derived either from observation of the user's velocity or the one selected, and the moments are calculated based on the GRF. Orientation vectors are projected on the biomechanical model of FIG. 22B, and the actual torque moments present at the user's joints are calculated as described in detail with reference to FIG. 24C. In some embodiments, the results can be presented in any convenient format, such as in visual or statistical forms 1930 as shown in FIG. 19B.

The corrective feedback is derived in Step 5 from a difference between the corrected real-time data of the user's natural gait parameters obtained in Step 3, modified by optimal biomechanical model of activity. Now, at each sample time, using the past and current orientation vectors and time, location and magnitude of GRF, the analyzer estimates current COP trajectory and derives the corrective feedback. The corrective feedback is proportional to the difference from the optimal trajectory (using a proper algorithm designed to minimize difference between observed and desired signal, such as, for example, an adaptive gradient algorithm, Kalman filter, etc.) This process may be visualized in FIG. 24A, where the desired COP trajectory should follow the path 2250. However, the observed trajectory progresses along the dashed line (vectors) of path 2251 or path 2253. Here, at each sample time (vector), the difference between the resultant calculated directions and the corrective stimulus is applied. In the examples shown in FIG. 24A, if the path diverges to the path 2251, the stimulus indicates shifting pressure to the $5^{th}$ MT. Alternatively, if the path diverges toward path 2253, the stimulus would be made to indicate to the user to shift pressure point toward the $1^{st}$ MT. Furthermore, the amplitude and frequency of said stimulus may indicate an amount of pressure and time to assert. Alternatively, several haptic actuators may be used to identify the exact location of the pressure required for path correction.

Detailed Description of a Third Embodiment—for Use in Early Detection of Foot Disorders Some embodiments of the presently disclosed invention are intended for the early detection of abnormal temperature conditions of feet to facilitate prevention of ulcers in people having diabetes. In these embodiments, the foot temperature and lateral (shear) ground reaction forces (GRF) of users are continuously monitored for abnormal conditions. In some embodiments, such functionality is achieved by embedding into one or more footwear insoles several thin-film temperature and force sensors, a 3D motion processor, and a haptic actuator. In these embodiments, motion vectors and the vertical component of GRF vectors are used to compute the lateral component of GRF (shear force), while also monitoring changes of temperature in selected areas of the user's feet. The changes in foot temperatures and shear forces are compared against calibrated safety thresholds and if any parameter exceeds such safety thresholds, the user and/or designated medical professionals are alerted. In some embodiments, when any of the safety thresholds are exceeded, a haptic stimulus is transmitted to the actuator embedded under the user's toe, and an audio and text message, is transmitted explaining the nature of the alert. When the analyzer is configured for remote alerts, a detailed message is transmitted to a medical professional or professions, or to a medical facility. The medical facility may retrieve an entire log of data from the analyzer and in return transmit professional recommendations to the user's smartphone UI. The analyzer may be configured in such a way as to monitor and facilitate corrective action that the user may take in response to the local or remote advice by providing haptic feedback which indicates the proper distribution of force inside the footwear. The proper distribution of force inside the footwear may include a proper location of pressure, or proper orientation of the footwear in 3 dimensional space. Furthermore, in these embodiments, the haptic actuator may be used to determine a level of neuropathy in the user's foot.

It has been recognized that the main causes of ulcerations are diabetic neuropathy and vascular disease. Uncontrolled diabetes leads to various complications affecting the diabetic's feet, in addition to other maladies. Foot complications are one of the most frequent problems caused by diabetes and key contributors to medical problems and most diabetic inpatient hospitalizations. The two main causes of diabetic complications are: (a) decreased blood supply and (b) loss of sensation in the diabetic's feet (neuropathy). During active walking, the foot temperature rises due to the GRF—vertical, horizontal and lateral forces, and due to the loss of sensation in the feet. Such temperature changes are unnoticeable to diabetics suffering from neuropathy and thus can frequently lead to ulcers and even to amputation of the affected feet. The changes in foot temperature leading to an ulcer condition may progress over a period of time. Consequently, monitoring feet temperature using a thermometer is impractical and difficult to quantify. The difference between a healthy temperature and one leading to ulceration may be as low 1 to 2 degrees Celsius, and when the feet temperatures rise to 42 degree Celsius (108 F) skin cells die. It is clear, that the range of foot temperature depends on the individual and also on the type of exercise being performed. Diabetics having neuropathy are usually advised to frequently monitor the temperatures of their feet. One of the most advanced monitoring methods is the use of thermography. Thermography is usually performed using an infrared scanner embedded in a scale used for measuring weight embedded in a similar device. While this method provides a good thermal color map of the temperature of a foot, the color map is difficult to interpret by an untrained person. Also, even when such a device produces data in the form of a graph, and even if a diabetic person is in possession of such a device, performing such measurements will most likely be limited to once-per-day if not less frequently.

It is well understood that the foot temperature is not constant. Foot temperature depends on the activity of the feet. It will also greatly depend on the walking pattern. A person's gait, the type of exercise performed such as a casually walking, running hiking, playing sports, etc., all will affect the temperature of a person's feet. In addition to the changes in body temperature experienced depending upon the different activities a person is performing, the range of GRF affecting the user's feet also changes drastically. For healthy people one major challenge is control (for example via the type and quality of footwear) of the vertical component of GRF. Diabetics must control other components of GRF. Specifically, the vertical and the lateral GRF component is critical for a diabetic because those components, sometimes referred to as shear force, causes friction between the user's foot and the footwear soles. For a diabetic, these forces are a significant contributor to local increases in the foot temperature which may result in foot ulcers.

Some embodiments of the present invention allow for constant monitoring of feet temperatures and lateral shear forces, which is simple and easy to use and provides real-time feedback and emergency notifications. These embodiments of the system comprises: a 3-axis accelerometer sensor; a 3-axis gyroscope sensor; and a 3-axis magnetometer sensor; a processor executing motion processing algorithms; a plurality of force sensors; a plurality of temperature sensors, and a control microprocessor embedded in the footwear insoles. This system is configured to analyze lateral (shear) component of GRF ground forces present at the foot/footwear interface. The system also monitors variations in temperature at specific areas of the user's foot and alerts the user and/or medical professional when the foot temperature exceeds one of a predefined criteria. In addition to motion, force and temperature elements, these embodiments also include a wireless personal area network (PAN) transceiver used to transmit of motion, force and temperature data to a smartphone based analysis application. Examples of the PAN transceiver include Bluetooth, ANT, etc. These embodiments also include a cellular radio interface to transmit calibration and analysis data, the user's GPS coordinates, and alert messages to a remote location.

Figure 25A:
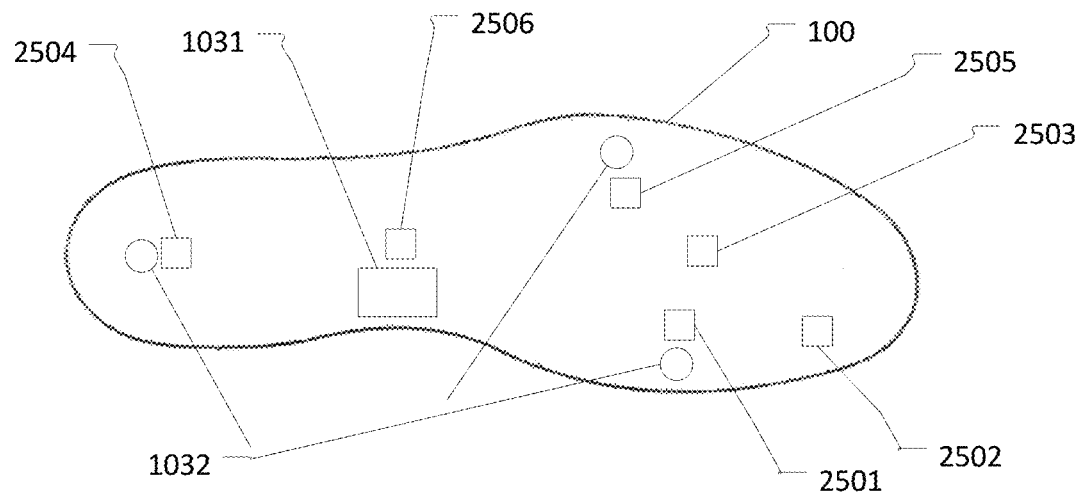
FIG. 25A shows an exemplary system embedded in the footwear insoles configured to for early detection of foot abnormalities of subjects with diabetics by measuring changes in foot temperature and horizontal components of GRF.
Figure 25B:
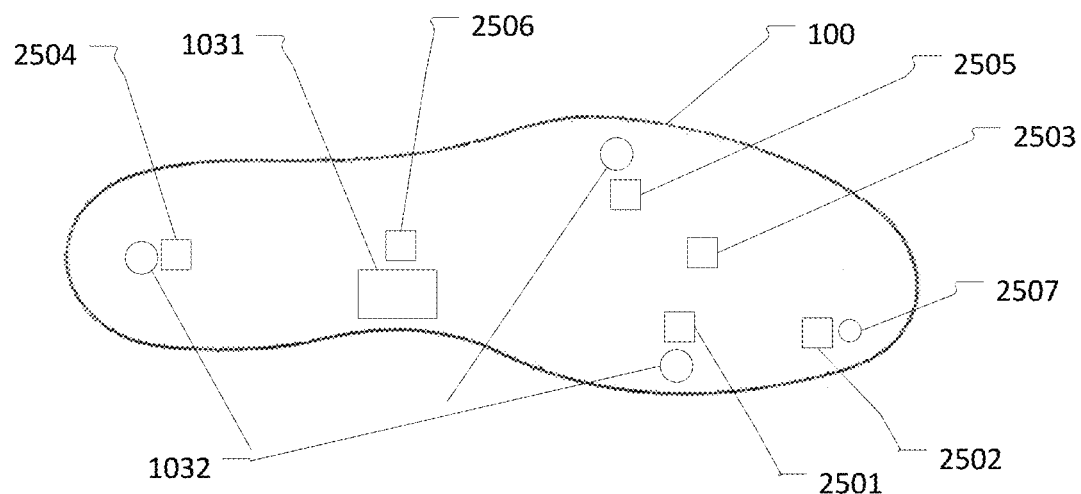
FIG. 25B shows an exemplary system embedded in the footwear insoles configured to for early detection of foot abnormalities of subjects with diabetics by and for detecting level of neuropathy and use such level as criteria during measuring changes in foot temperature and horizontal components of GRF.

Two versions of such systems are similar to the system for gait analysis described above. Two versions of such systems are now described with reference to FIGS. 25A and 25B. The system shown in FIG. 25A, comprises: a motion processing element, configured to obtain samples from an accelerometer, a gyroscope, a magnetometer; a plurality of force sensors 1032; and a plurality of temperature sensors located under: a $1^{st}$ MT 2501; a $3^{rd}$ MT 2503; a $5^{th}$ MT 2505; a big toe 2502, a heel 2504; and a foot arch 2506. The system shown in FIG. 25B includes a haptic actuator 2507, and a haptic actuator 2508 for the left and right foot, respectively. The haptic actuators 2507, 2508 are located under the user's big toe of the left and right foot, respectfully. The haptic actuators 2507, 2508 are used to determine the level of neuropathy by providing specific vibrating stimulus to the user's big toes and measuring the response thereto. This allows the system to determine a level of sensation loss and as a consequence, obtain a foot vibratory perception threshold (VPT), as well as to provide feedback when some of the safety parameters are exceeded.

The processing element obtains samples from an accelerometer, gyroscope, magnetometer, force and temperature sensors at a specified rate. The system then computes Euler angles and Quaternion, and assembles a data packet comprising x, y and z samples from accelerometer; x, y and samples of Euler Angle. The magnitude of GRF are recorded by the force sensors 1032, and the temperature of the feet are recorded by the temperature sensors 2501 through 2506, and 2501' through 2506'. The system transmits assembled packets containing this data to the smartphone-based analysis application using the Bluetooth radio interface or other convenient communications interface. Using well known Cartesian arithmetic the GRF ($F_z$) can be computed based upon the received horizontal and lateral component of the GRF.

It is well understood that the magnitude of GRF depends on the type of physical activity performed by the user. For example, a large vertical component at the front of the foot is experienced when the user runs on a flat surface and a large vertical component is present on the heel when running down a slope. Also, a large lateral component is present when playing sports requiring dynamic side-steps (for example, when the user plays tennis). The analyzer system of the present disclosure may determine activity type with a large degree of confidence by observing velocity and acceleration vectors. However, a significant improvement in the quality of analysis is provided by entering the activity type a user is engaged in using the application UI.

Medical infrared (IR) diagnostics are based on the principle that pathological processes in human organs manifest themselves as local changes in heat production and changes in blood flow pattern of affected organs or tissues. As the foot temperature varies depending on, for example, ambient temperature, user activity, etc., measurement of absolute foot temperature cannot be considered. However, as numerous studies have shown, foot temperature of subjects with neuropathy may be 3-5 degrees C. higher than the foot temperature of subjects not having neuropathy. This problem may be mitigated by the fact that there is a strong correlation between temperatures that are measured on the same location of a subject's left and right foot. During calibration of the temperature sensors this correlation is used to obtain safety thresholds for each area of the foot.

While a strong correlation between the temperature of a specific area of the foot is well documented, what is also known, is the fact that the level of neuropathy has a strong correlation with the severity of ulceration in patients with diabetes. Furthermore, while a person may have neuropathy in both feet, it is very unlikely the level of neuropathy will be similar in both feet. Considering the above, it is reasonable to assume that temperature and shear force safety thresholds are dependent on a subject's feet neuropathy levels. Currently available methods for determination of neuropathy is performed in a specialized laboratory using a biothesiometer. A biothesiometer is a mechanism that vibrates at 50-60 Hz at an amplitude proportional to the applied voltage. This stimulates the subject's foot, who in return confirms (or does not confirm) the level of sensation as the amplitude level is varied. Such measurements, while accurate, disadvantageously cannot be performed frequently. Also, the vibrations impacted on the subject's feet are often not accurately interpreted by the subject. In contrast, advantageously, in some embodiments, the presently disclosed system uses a haptic actuator positioned under the subject's big toe. The haptic actuator periodically varies the vibration amplitude and records the subject's response via the smartphone UI. Such VPT is used as a coefficient that is applied to the safe temperature threshold. This effectively narrows a safe temperature range. During analysis, if any area of the foot exceeds the safe temperature threshold, or if the shear force component of the GRF exceeds the safe force threshold, the application transmits an alarm message to the user and/or medical professional, informing the user or medical professional of the abnormal foot conditions.

When monitoring temperature of a foot, one must consider several important parameters, such as the following parameters: (a) a mean temperature recorded by the sensors; (b) the temperature difference between same area of both feet ($\Delta T$); and (c) a normalized temperature ($T_N$). Before analysis is performed, these and other parameters are calibrated. The motion and force sensors are calibrated as described in more detail above with reference to FIGS. 23A and 23B. The temperature sensors and safety thresholds as described in more detail above with reference to FIGS. 25A and 25B.

The calibration of temperature sensors is performed as follows:
  a. The user steps into the footwear and stands in a relaxed bi-pedal position with the user's weight equally distributed between both feet; then for each foot the analyzer performs the following:

a) for each temperature sensor embedded in the footwear insoles, obtain an average of multiplicity measurements temperature averaged over 16 consecutive measurements, then:
　i) for each foot:
　　1) calculate the mean sensor temperature (MSF) by taking a mean of all sensors;
　　2) if the temperature recorded by each individual sensor value is larger than the MSF, store the result as a negative offset $TS_{ofst}$ of the respective sensor, else, if the individual sensor value is smaller than the MSF, store the result as positive $TS_{ofst}$ of the respective sensor;
b. instruct the user to remove socks and lay-down in a prone (i.e., resting) position for 3-5 min, then, instruct the user to step (barefoot) onto the insoles while the user remains in the natural stance for 15-20 sec, then for each foot:
　a) perform 64 independent measurements of temperature averaged over 16 consecutive measurements (for a sampling rate of 60 Hz this will take approximately 15 sec.);
　b) for each foot:
　　i) Add the respective sensor $TS_{ofst}$ recoded in step a) i) 2) and store as normalized foot $TF_{Norm}$ for the respective sensor;
　　ii) calculate the mean foot temperature (MFT) by taking a mean of all $TF_{Norm}$;
　a) calculate a temperature difference between the same area/sensor of both feet by comparing respective area $TF_{Norm}$ and storing the difference as a $\Delta TF_{Threshold}$.

Figure 26A:
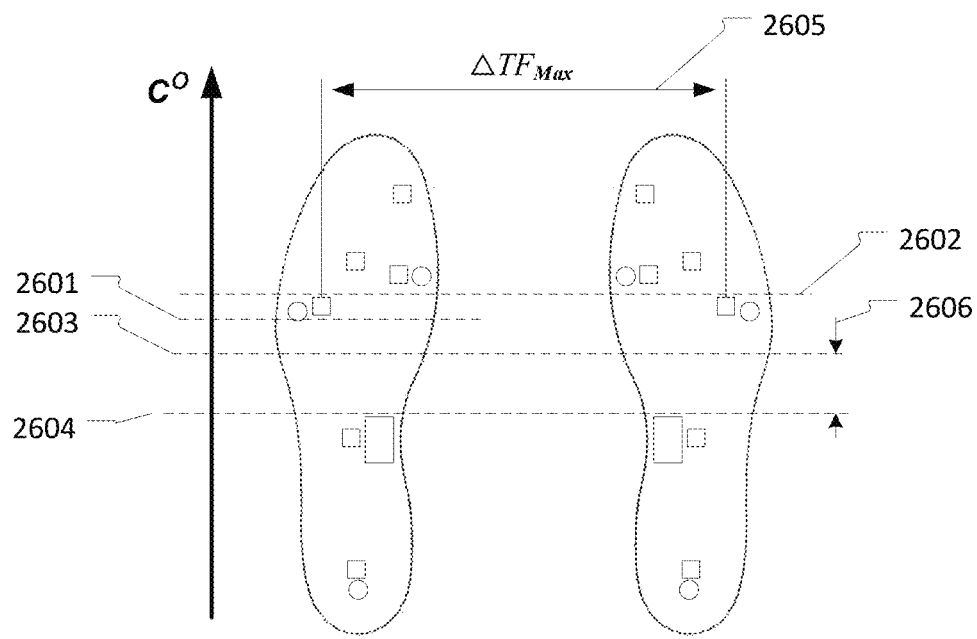
FIG. 26A shows an exemplary method of calibration of temperature sensors, obtaining the subject normal foot temperature and determining the safe temperature criteria.

The relationship between parameters obtained during the calibration and monitoring method set forth above is described with reference to FIG. 26A. Here the $TF_{Norm}$ for the subject's 5$^{th}$ MT of the left foot 2601, and the right foot 2602, the left foot MTF 2603 and right foot MTF 2604, and the $\Delta TF_{Max}$ threshold 2605 indicates the maximum difference in the temperature between 5$^{th}$ MTs of the left and right feet. The difference between the MTF of the left foot 2603 and the right foot 2604 defined as $\Delta MFT_{Max}$ 2606 determines the maximum range between ($TF_{Norm}$) of the left and right feet. If any of the thresholds is exceeded, the application sends an alarm message to the user UI and/or to the medical professional.

In addition to previously described calibration of temperature sensors, the vibration perception threshold level of sensitivity (VPT), indicating a level of sensitivity (neuropathy) of each foot, allows to modify the safety threshold, in case sensitivity of one foot differs from sensitivity of the other. The VPT is obtained by stimulating the haptic (vibrating) actuator embedded in the insole and located under the user's big toe. In some embodiments, a stimulus with a frequency of approximately 60 Hz is incrementally increased in amplitude. This is calibrated against standard biothesiometer equipment while the user provides a response to detection of the sensitivity level through the smartphone UI. During the VPT sensitivity test, a code word defining amplitude level is applied to a digital-to-analog converter (DAC) for a specific period of time. If and when the user acknowledges detection of the vibration, the vibration amplitude level is stored indicating the VPT threshold. It may be beneficial to repeat the VPT threshold detection several times in order to obtain an average VPT threshold.

More specifically, the calibration of the foot VPT is performed as follows:
a. Instruct the user to step onto the insoles and to enter the VPT test;
b. For each foot:
　i. apply the lowest amplitude to the haptic actuator, wait for the user's acknowledgement (ACK) and record the time;
　ii. repeat step i N times, where N is a preselected integer number, and obtain a mean of the level and a mean of the response time;
　iii. if no ACK is received, increase the vibration amplitude and repeat step b. until the user acknowledges (i.e., an ACK is received) the stimulus produced by the haptic actuator;
　iv. Store the VPT level as $F_{VTP}$.

Figure 26B:
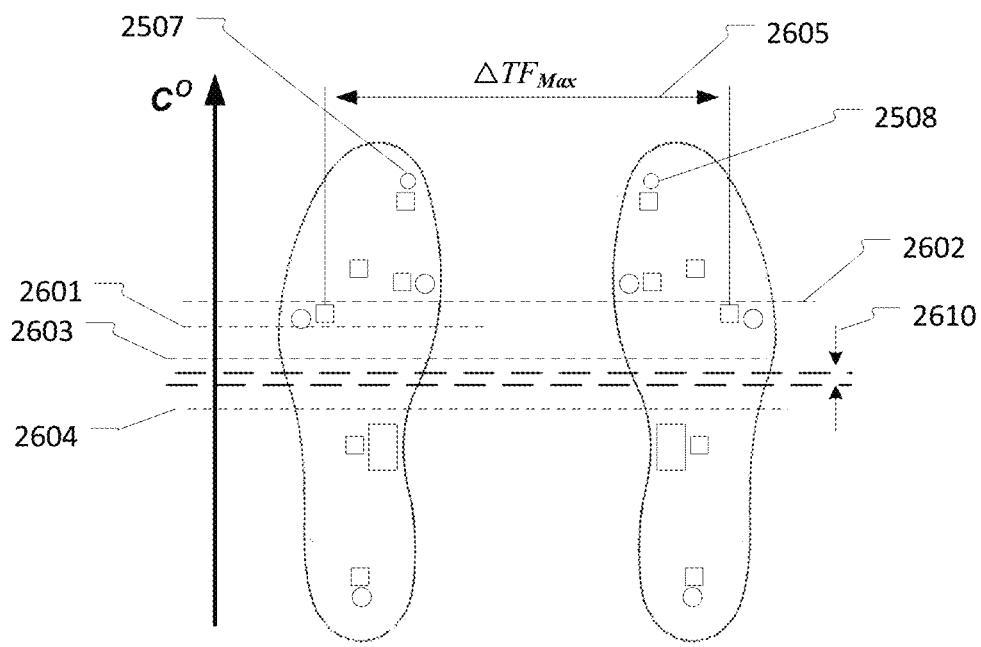
FIG. 26B shows a method for obtaining the level of neuropathy and its application to establishment of safe temperature criteria.

The VPT level allows for adaptation of the temperature alarm threshold according to the user's neuropathic condition, assuming the higher the VPT level the lower the level of sensitivity of the foot to changes in foot temperature. It has been observed that long term increases in foot temperatures result in increases of the probability of foot ulcerations. If an increase in VPT above the normal level is detected, the VPT associated with the affected foot is used to lower the safe temperature threshold level proportionally to $F_{VTP}$. This procedure is described with reference to FIG. 26B. Here the $TF_{Norm}$ for the 5$^{th}$ MT of the left foot 2601, is still slightly higher than temperature of the right foot 2602. The left foot MTF 2603, and the right foot MTF 2604, is practically identical as described with reference to FIG. 25A, however, but the VPT level obtained during the calibration of the left foot is 20, while the VPT level of the right foot is 25. As the VPT level above 20 and 25 indicates medium and severe neuropathy, respectively, the VPT level of the right foot is used as a coefficient to calculate MTF as follows: VPT/100 to obtain new $\Delta MFT_{Max}$ 2610, does effectively lower the difference between left/right 5$^{th}$ MT as:

$$\Delta FT_{Max} = (\text{Left}\_TF_{Norm} * \text{VPT}/100) - (\text{Right}\_TF_{Norm} * \text{VPT}/100).$$

While the increase in foot temperature is the main reason for ulceration in persons with diabetes, a significant cause of the increase in foot temperature is the shear force on the foot. The shear force is the horizontal and lateral component of GRF. Such forces induce friction between the user's foot and footwear insoles thereby causing increased foot temperatures and associated ulcerations. Furthermore, as changes in the foot temperature are gradual and the resultant ulceration may be delayed by a few days, and a reasonable measuring period may be in a range of 5-10 minutes, the excessive shear forces (measured at the rate of motion: 20-100/sec), information about friction associated with such forces over prolonged periods of time provide an early warning of increases in foot temperature. Based on motion/force vectors and the user's location coordinates, we can estimate the type of the activity, and accordingly provide warnings or advice via the smartphone UI or to the haptic actuator.

The GRF always consists of three components: vertical $F_z$; horizontal $F_y$; and lateral $F_y$, with the vertical component being the largest. The horizontal and the lateral components and their associated moments $M_x$ and $M_y$, referred to herein as shear force, are enhanced for a person with an abnormal gait (overpronation, supination), or a person exhibiting pain in a foot or feet. This might be indicative of an early stage of ulceration, wherein the subject attempts to compensate pressure by changing their foot stance pattern.

Relation between vertical component of GRF and motion is described in detail above in relation to the description of gait analysis. As processing of the vertical component of GRF is similar to the description provided above with regard to the gait analysis embodiments, here we describe the process of obtaining the $F_x$, and $F_y$ components and how the relationship between those components, the $F_z$ component, and the motion vectors is used as an early indicator of an increase in temperature of an affected foot area. The peak magnitude of the vertical component of GRF is approximately 120% during a walk, about 180% during a jog, and as much as 275% of the user's body weight during a run. The shear forces during a walk and jog are similar with the magnitude of about 30% to 35% during a walk, and as high as 45% of the user's body weight during a run. The lateral component (shear forces), specifically critical for a person with diabetes and even more if such a person suffers from neuropathy. The shear force is also very critical to any athlete as such activities involves a large number of repetitions—long distance runner, basketball player performing repeated lateral shuffling from one foot to another or quick sidestep cutting. In all those cases, shear force producing friction between the foot and the footwear soles leads to development of calluses and even ulceration. As such, analyzing of complex GRF in 3D space provides potential to avoid many foot injuries by alerting the user when such forces exceed predefined safety threshold or when a repetitive force may lead to a stress in the specific foot area.

Detection of the user's activity may be made by observation of the user's speed, for example: walking=3-5 km/hr.; jogging=5-11 km/hr.; and running⇒11 km/hr.; acceleration vectors integrated over period of time, magnitude of vertical, horizontal and lateral GRF, and the user's location coordinates. The horizontal and lateral GRF have significant effects on friction inside the user's footwear. Areas of friction produce a resultant increase to foot temperature in those areas. While such local increases in the foot temperature may be of no concern to a healthy person, it may be critical to a person with diabetes. They can even cause foot ulcerations to occur. Monitoring gradual changes in foot temperature while considering temporary increases due to specific activities provides long term safety, while providing comfort of normal life activities. Detection and analysis of shear forces is now described in detail with reference to FIGS. 27A and 27B. The results of this analysis are described in detail with reference to FIG. 27C. The safety thresholds of the shear force is obtained using the following parameters:

a) user's calibrated (normalized) body weight; and
b) user's natural pronation parameters.

The safety threshold on the vertical GRF is set to 120% of the user's normalized body weight for walking; 170% for jogging and 250% of the user's normalized body weight. Then a safety threshold of shear force determined by subtracting values of horizontal and lateral force obtained by multiplying the user's normalized body weight by the value obtained during the calibration of user's natural pronation from the values of the accelerometer x and y axis, from 25% for walking; 35% for jogging, and 45% of the user's normalized body weight for running. Those thresholds may be adaptively modified based on several criteria, such as: increase of foot temperature or user's neuropathy level. The process of monitoring is described below.

Figure 27A:
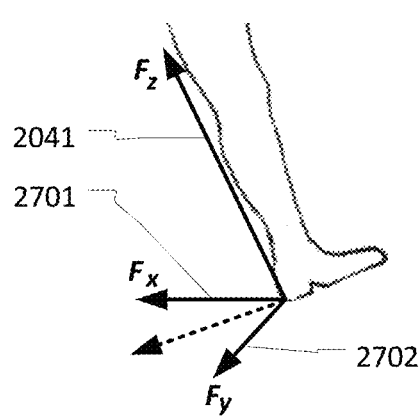
FIG. 27A shows an exemplary relation of vertical and horizontal components of GRF during initial heel contact indicating start of the stride.

FIG. 27A presents forces during the initial heel contact. Such contact may indicate the start of a stride during a walking motion, or a dynamic stop during a tennis or basketball game, etc. The start of the stride is easily determined by observing motion vectors vs. location coordinates. FIG. 27A shows the vertical GRF vector 2041, (obtained from the force sensor located in the heel and via the Euler Angles). The magnitude of the vertical vector 2041 is proportional to the user's weight and activity, and is transmitted through the user's joints in the direction of the user's COM. The direction and magnitude of the horizontal component $F_x$ 2701, and lateral component $F_y$ 2702, of GRF is obtained by observing the magnitude and sign of the accelerometer x and y axis, respectively, while the direction of those vectors is obtained from Euler Angles provided by the motion processing algorithm, produce a vector of shear force 2703. This may be further described with reference to FIG. 27B. Here, a user with supination 2254, or a user with neutral pronation but displaying a side-to-side motion during tennis, or sport, places most of the force and the moment on the outside portion of foot. Here, the orientation and rotation angles are provided by Euler Angles, the accelerometer x-axis and y-axis provides the magnitude of horizontal and lateral forces, and the magnitude of the friction/shear force 2703 force can be calculated using Pythagorean principles.

Figure 27B:
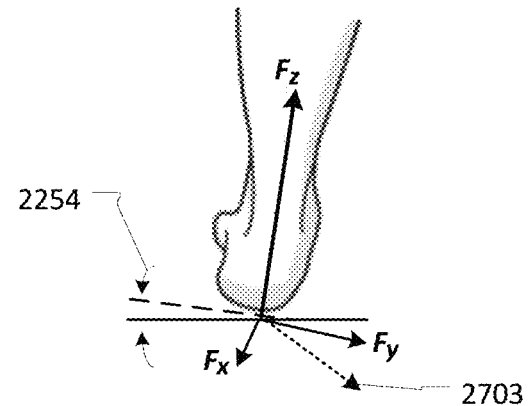
FIG. 27B shows a relation of GRF during side-to-side movement for subject with supination.
Figure 27C:
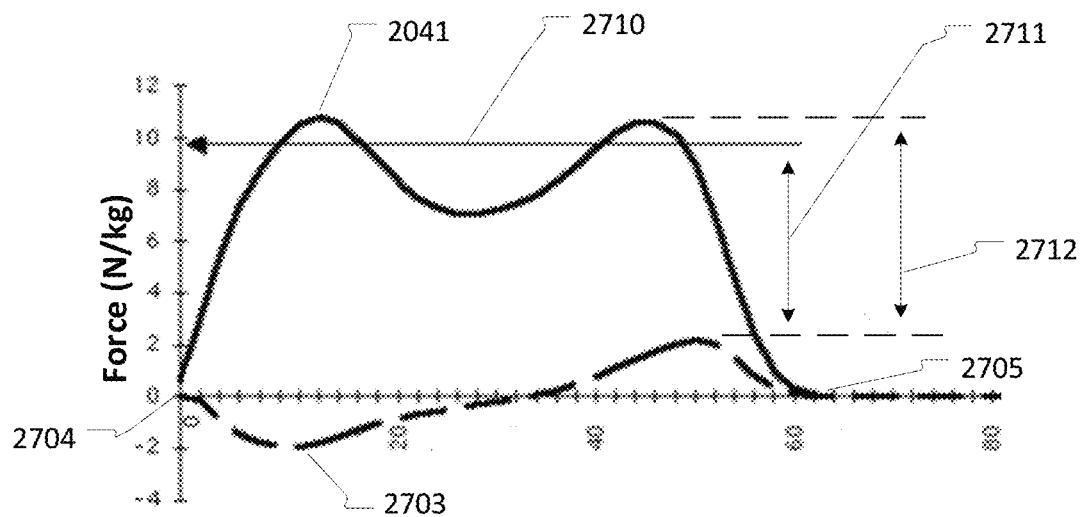
FIG. 27C shows a method to determine safety thresholds of shear force (horizontal and lateral components of GRF).

Thresholds obtained from these calculations are presented in relation to the vertical and shear components of the GRF in FIG. 27C. During analysis, the normalized body weight line 2710 (obtained during calibration of the force pressure sensors by subtracting ½ of the body weight provided in the user's physical parameters from the vertical GRF vector), is compared with the shear component of the GRF 2703. The ratio between the vertical component of GRF 2041 and the shear components of the GRF 2703 is monitored. This ratio is monitored over a full gait cycle and begins at a time of the initial heel contact 2704 and terminates at the time of the toe contact 2705. During this period, a ratio of the $F_z$ 2041, to $F_{shear}$ 2703, is compared to threshold 2712, and a ratio between normalize body weight 2710 and $F_{shear}$ 2703, is compared to threshold 2711. When the ratio between the max shear force 2703 (note depending on sign of acceleration along x and y axis, the shear graph in FIG. 27B is positive or negative), is below the threshold 2711 (the negative vector of the shear force is simply inverted for this calculation), or when the ratio between the max shear force and the $F_z$ component is below the threshold 2712, an activity timer is started. The periodicity of monitoring foot temperature is increased, and if such conditions persist over a time longer than a normalized time for this activity, or if the foot temperature rises monotonically, a warning message is sent to the user and/or the medical professional.

Figure 28:
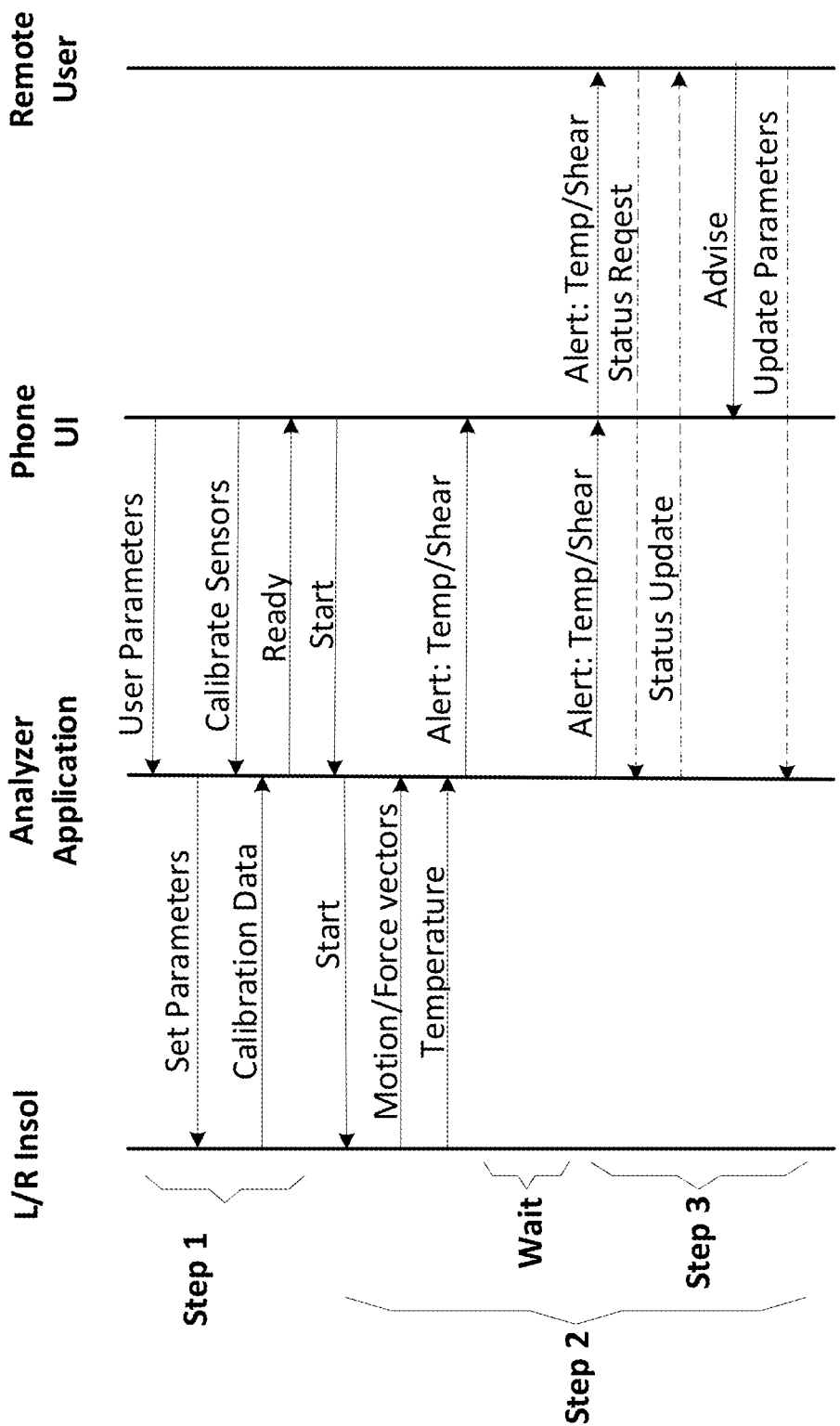
FIG. 28 shows a communication protocol between insoles, analysis application, the user and the remote medical supervisor.

While monitoring of the user foot temperature and the shear forces, the analyzer exchange messages intended to alert the user and/or the remote medical facility when any of safety parameters are reached. To provide such functionality, in some embodiments, the analyzer employs a messaging protocol described below with reference to FIG. 28. This protocol comprises three steps: 1) calibration procedures; 2) data collection and analysis; and 3) alert procedures. Step 1—this step is described in detail in the previous sections. This step starts with entering of the user's specific information, followed by calibration of motion, force and temperature sensors, and ends with the "Ready" status sent to the UI. Step 2—this step begins when the user sends a "Start" command—initiating analysis. At this time, the application starts receiving motion, force and temperature data at a rate defined in a "Set Parameters" message. Such data rate may, for example, be set to 100/sec for motion and force vectors, and 1/min for the temperature. While continuously processing the sensors' data, the analyzer application monitors to determine if any of the safe thresholds are exceeded. If so, an "Alert" message is transmitted to the smartphone UI. The method then enters a "Wait" state, waiting for the user's corrective action to correct the current alarm condition. Duration of the "Wait" state depends on the priority of the threshold type, or the rate of change in the measured parameter, such as, for example, a slope of temperature change.

After the "Wait" time is reached and the parameter causing the alarm trigger did not return to the nominal level, application enters Step 3 of the process. Otherwise, if the offending parameter returns to a "normal" value, for example, if the user changed the user's activity pattern, the application cancels the alarm condition and returns to the normal Step 2 processing. In Step 3—while continuously processing the sensors' data, the application transmits alert messages to all remote user(s)/medical professional(s) included in the application's "Contact List" as well as to the user UI, informing of the "Alert" condition. In response, the remote user/medical professional may request a detailed "Status Report" containing statistical information of a specific period. After reviewing such information, the remote user/medical professional may transmit an "Advise" message to the user and may remotely "Update" the application threshold parameters. If the threshold was updated and/or the parameters returned to nominal value, the application returns to normal Step 2 processing. Otherwise, the application will periodically send the Step 3 "Alert" messages to all recipients included in the application "Contact List".

Detailed Description of a Fourth Embodiment

In this embodiment, the systems described above (specifically, the embodiment of the system whereby motion is analyzed in relation to ground reaction forces; and the embodiment of the system whereby analysis of abnormal condition of temperature in persons with diabetes is performed) are integrated with more sophisticated services and systems. Such services and systems may provide high-resolution scanning of the foot features/temperature, fabrication of custom fitted insoles using 3D printing techniques, maintain secure data base of user information and perform analyses that are not possible using smartphone processing capabilities dedicated to the specific user or the specific medical personnel requirements.

Figure 30:
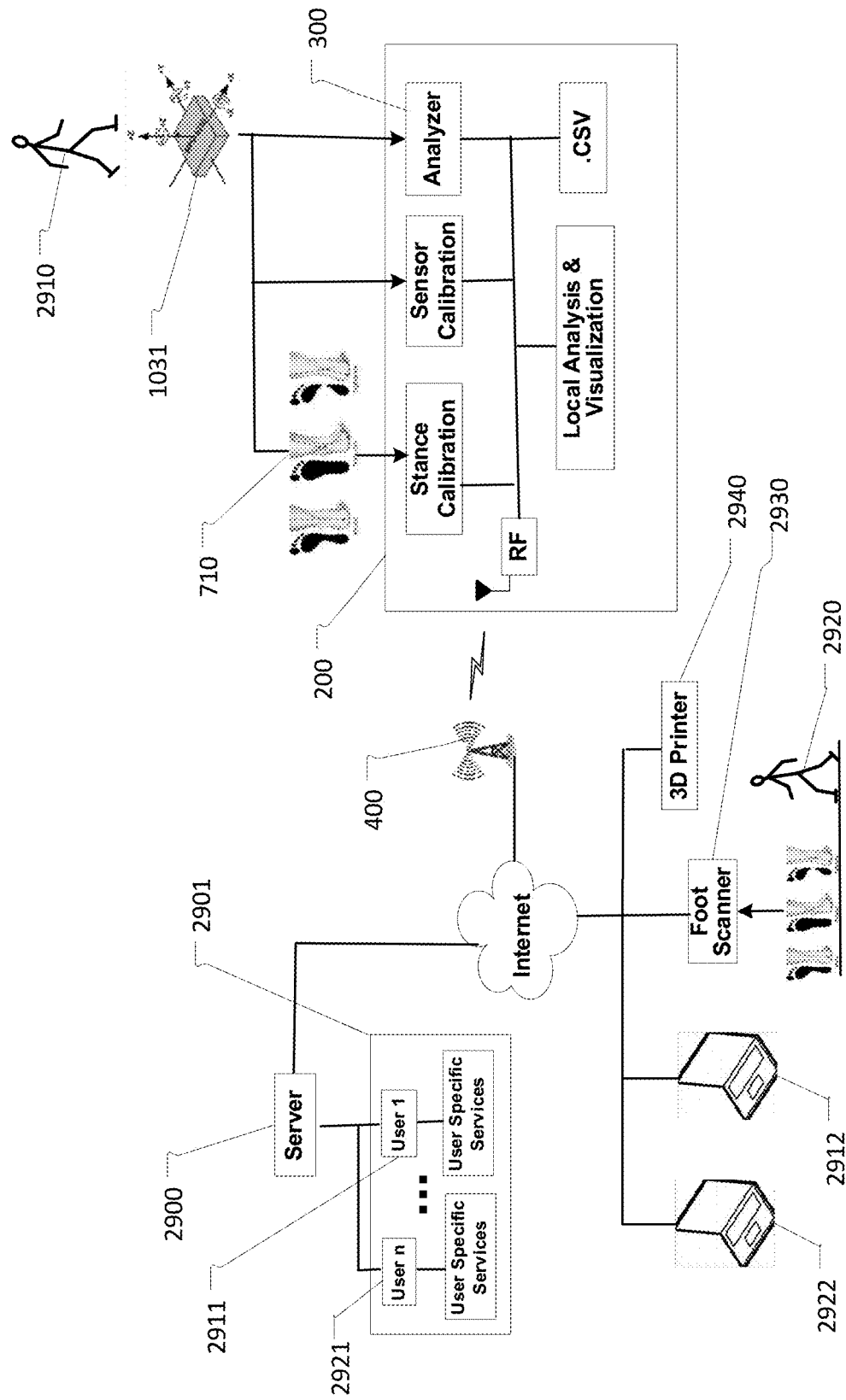
FIG. 30 shows an integrated foot analysis system.

One embodiment of such an integrated system is described with reference to FIG. 30. The analysis system 300, in the embodiment shown executed in software running on a smartphone 200, communicates with the motion and force processing element embedded in insoles worn by a user 2910. In some embodiments, this communication is performed using a wireless PAN protocol. The smartphone 200 communicates via a wireless cellular interface 400 with remote services embodied on a remote computing server 2900.

In one mode of operation, after obtaining global and local coordinates from a motion and force processing element 1031 embedded as described in the sections above in the insoles worn by the user 2910, the analyzer 300 obtains natural pronation of the user 2910, feet 710, as described above with reference to FIGS. 23A and 23B. The analyzer 300 then proceeds with its analysis according to a specific user activity type: (a) skiing—as described above with reference to FIGS. 14-17; (b) walk/run/gait—as described with reference to FIGS. 20B and FIGS. 21-24; or (c) foot temperature—as described above with reference to FIGS. 26-28. In this mode, results of said analysis is transmitted to the computer server 2900 which maintains results of the user calibration and analysis 2911, in a secure (HIPAA) data base 2901. The user's data may be retrieved and presented remotely on a secure terminal 2912 by the user or an authorized medical professional.

In another mode of operation, a scan of the feet of another user 2920 is obtained by a foot scanner 2930. In some embodiments, and without limiting the type of scanner that may be used to practice the above-described systems, the foot scanner 2930 may comprise one of the following: a FitStation®, a FootScan®, or a thermography scanner such as a SpectraSole® or TempStat® scanner. Some foot scanners provide a highly accurate scan of the physical characteristics of the user's feet. Some of these scanners use a combination of 3D laser scans, a pressure plate, etc. to obtain foot volume, pronation, pressure and gait patterns, dynamic knee variation and propulsion index, to name a few of the types of data that may be obtained. The thermography scanners may use IR cameras, liquid crystal imaging, etc. to provide an accurate reading of the foot temperature distribution and for a skilled professional, to aid in determining a subject's neuropathy or to detect neuropathic exhaustion wounds.

A subject's pronation, pressure and gait pattern, and/or foot temperature distribution may be stored in memory maintained by the computer server 2900. This information may be uploaded to the analyzer 300 via the cellular radio interface 400. In this mode, the uploaded data may replace the following data: pronation; natural gait parameters used to build the user's kinematic model; foot pressure pattern; foot temperature distribution, and calibration parameters. In some embodiments, and based upon the information provided by a scanner, the computer server 2900 may create insoles (or entire footwear) for the user 2910 or the user 2920. The computer server 2900 may create a design file, for example in STL format, and this design file may be transmitted to a 3D printer 2940 for use to create user insoles or footwear. The users receive insole/footwear, custom made for his/her specific feet, activities and determined by the type of analysis used to create the design files. The computer server may upload an application with customized calibration, or it may replace calibration parameters previously installed in the smartphone 200.

In case the insole/footwear are not fabricated by the same 3D printing process, the user 2920, may calibrate the footwear orientation, as described above with reference to FIGS. 23A and 23B. Also, unless a medical professional, after reviewing the user feet thermography data, determines different thresholds for: $\Delta TF_{Max}$ 2605, $\Delta MFT_{Max}$ 2606, and VPT level, such thresholds will be determined by the analyzer 300.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes", "has" or "having" are used in either the detailed description or the claims, such terms are intended to be inclusive in a manner similar to the term "comprising" as "comprising" is interpreted when employed as a transitional word in a claim.

It is understood that the specific order or hierarchy of steps in the processes disclosed is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented Those of skill in the art would understand that information and signals may be represented using any of a variety of different technologies and techniques. For example, data, instructions, commands, information, signals, symbols, etc. may be referenced throughout the above description by other means.

Those of skill would further appreciate that the various illustrative logical blocks, modules, and algorithmic steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

What is claimed is:

1. A system for detecting foot disorders in diabetic subjects, comprising:
   (a) first and a second footwear fitted for a selected subject's first and second foot, respectively, wherein both the first and the second footwear includes the following:
      (1) a 3-axis accelerometer;
      (2) a 3-axis gyroscope;
      (3) a 3-axis magnetometer;
      (4) a plurality of force sensors placed under the selected subject's feet generating associated and corresponding force vectors, and wherein a shear force is applied to both the first and the second foot, and wherein the force vectors and the shear forces are collectively referred to as force information;
      (5) a plurality of temperature sensors measuring skin temperature and generating foot temperature information for both of the selected subject's feet;
      (6) haptic actuators placed under the big toe of the selected subject's first and second foot, wherein the haptic actuators provide stimulus that assists the system in determining whether the selected subject has a foot neuropathy condition;
      (7) a control microprocessor; and
      (8) a motion processing element, wherein the motion processing element obtains samples of sensor data during selected sampling periods from the accelerometers, the gyroscopes, the magnetometers, the plurality of force sensors and the plurality of temperature sensors, and wherein, at the end of the selected sampling periods, the motion processing element generates motion information including g-force, acceleration information, Euler Angles, Quaternion information and the force vectors; and
   (b) an analysis device, wherein the analysis device performs the following:
      (1) using the motion information, obtains natural pronation of the selected subject's feet;
      (2) using the motion information, the force information, and the selected subject's physical characteristics, computes a distribution of ground reaction force (GRF) for each of the selected subject's feet, and determines a shear force safety threshold by computing vertical and horizontal components of the GRF for each of the selected subject's feet;
      (3) using the temperature information:
         a. determines a normalized temperature for each of the selected subject's feet; and
         b. determines normalized temperature safety thresholds based upon a correlation of temperature information between similar locations of the selected subject's feet;
      (4) determines a vibratory perception threshold (VPT) indicating the selected subject's feet neuropathy level, and adjusts the temperature safety thresholds depending on the VPT of the selected subject's feet; and
      (5) determines the shear force applied to each of the selected subject's feet based upon the force information and the GRF for each of the selected subject's feet, and modifies the temperature safety thresholds and the shear force safety thresholds depending on the selected subject's activity;
   and wherein the analysis device continuously monitors the motion information generated by the motion processing element, the GRF, and the foot temperature information to determine variations in the foot temperature information and the shear forces; and
   wherein variations in the foot temperature information and the shear forces are compared to the foot temperature and the shear force safety thresholds, and wherein if any of the safety thresholds are exceeded, an alert is generated.

2. The system of claim 1, wherein the alert comprises a haptic warning that is transmitted to the selected subject.

3. The system of claim 1, wherein the alert is transmitted to an appropriate medical professional for further action.

4. The system of claim 1, wherein each of the haptic actuators are positioned under the selected subject's big toes, and wherein the haptic actuators are used to determine a level of neuropathy in each of the selected subject's feet by providing specific vibrating stimulus to each of the selected subject's big toes and measuring the selected subject's response thereto.

5. The system of claim 4, wherein the selected subject has a level of sensation loss in one or both of the selected subject's feet, and wherein the level of sensation loss is determined based upon the selected subject's response to stimulus provided by the haptic actuators, and wherein a foot vibratory perception threshold (VPT) is determined for each foot based upon the sensation loss experienced in each of the selected subject's feet by the selected subject.

6. The system of claim 5, wherein the VPT for each foot is determined by vibrating the haptic actuator of each foot with a selected frequency and amplitude of vibration, and wherein the vibration amplitude is increased over a selected period of time until the selected subject responds to the vibration, at which time the vibration amplitude level is stored indicating the foot vibratory perception threshold (VPT) for each foot.

7. The system of claim 6, wherein the selected frequency of vibration is approximately 60 Hz.

8. The system of claim 6, wherein the VPT for each foot is determined a selected number of times thereby producing an average VPT threshold.

9. The system of claim 5, wherein the VPT for each foot is used as a coefficient that is applied to a safe temperature threshold effectively narrowing a safe temperature range.

10. The system of claim 9, wherein for the selected subject's first foot and the associated and corresponding first footwear, a first temperature sensor is positioned under the selected subject's $1^{st}$ metatarsal (MT) bone, a second temperature sensor is positioned under the subject's $3^{rd}$ MT bone, a third temperature sensor is positioned under the subject's $5^{th}$ MT bone; a fourth temperature sensor is positioned under the subject's big toe, a fifth temperature sensor is positioned under the subject's heel; and a sixth temperature sensor is positioned under the selected subject's foot arch.

11. The system of claim 10, wherein the second footwear includes a plurality of second footwear sensors and elements identical to the sensors and elements included in the first footwear as set forth in claim 10, and wherein the second footwear sensors and elements are positioned in locations under the selected subject's second foot that are similar to the positioning of the associated and corresponding first footwear sensors and elements in locations under the selected subject's first foot, and wherein temperature sensor readings are obtained for the selected user's first and second foot, and wherein the following parameters are considered when determining if neuropathy exists in either of the selected subject's feet:
 (a) a mean temperature recorded by the plurality of temperature sensors;
 (b) temperature differences ($\Delta T$) between associated and corresponding temperature sensors in the first foot and in the second foot; and
 (c) a normalized temperature ($T_N$).

12. The system of claim 11, wherein a shear force component of a ground reaction force (GRF) is determined for both feet, and if any area of either foot exceeds a selected temperature safety threshold, or if the shear force component of the GRF exceeds a selected shear force safety threshold, an alarm message is generated informing of the presence of abnormal foot conditions in one or both of the selected subject's feet.

13. The system of claim 12, wherein the motion, force and temperature sensors are calibrated prior to the analysis.

14. The system of claim 13, wherein the VPT is calibrated by comparing the VPT with a second VPT determined using standard biothesiometer equipment.

15. The system of claim 13, wherein the accelerometer provides a magnitude of horizontal and lateral acceleration vectors, and wherein a magnitude of friction shear component forces is calculated by multiplying a magnitude of the vertical component of GRF by the acceleration vector of the respective axis using Pythagorean based algebraic principles.

16. The system of claim 15, wherein during analysis of the subject's first or second foot, a normalized body weight line is obtained during calibration of the force sensors by subtracting one half of the subject's body weight provided in physical characteristics of the subject's physical parameters from a vertical component of the GRF.

17. The system of claim 16, wherein a ratio between the vertical component of the GRF and shear components of the GRF are monitored over a full gait cycle, and wherein the ratio is compared to a selected first safety threshold, and wherein if the ratio between a maximum shear force falls below the first safety threshold or if the ratio between the maximum shear force and the vertical component falls below a second safety threshold, and if such conditions persist over a time longer than a normalized time for the subject's activity, or if the foot temperature rises monotonically, an alarm message is generated by the system.

18. A method of detecting disorders in a foot of a diabetic subject, wherein a selected subject may experience a loss of sensation in one or both of the selected subject's feet due to the selected subject being a diabetic, the method comprising:
 (a) fitting the selected subject with a first and a second footwear fitted for a selected subject's first and second foot, respectively, wherein the fitting of both the first and the second footwear include:
   (1) placing a 3-axis accelerometer within the first and second footwear;
   (2) placing a 3-axis gyroscope within the first and the second footwear;
   (3) placing a 3-axis magnetometer within the first and the second footwear;
   (4) placing a plurality of force sensors under the selected subject's feet generating associated and corresponding force vectors, and wherein a shear force is applied to both the first and the second foot, and wherein the force vectors and the shear forces are collectively referred to as force information;
   (5) placing a plurality of temperature sensors measuring skin temperature and generating foot temperature information for both of the selected subject's feet;
   (6) placing haptic actuators under the big toe of the selected subject's first and second foot;
   (7) providing a control microprocessor; and
   (8) providing a motion processing element, wherein the motion processing element obtains samples of sensor data during selected sampling periods from the accelerometers, the gyroscopes, the magnetometers, the plurality of force sensors and the plurality of temperature sensors,
     and wherein, at the end of the selected sampling periods, the motion processing element generates motion information including g-force, acceleration information, Euler Angles, Quaternion information and the force vectors;
 (b) analyzing the information generated by the first and the second footwear by performing the following:
   (1) using the motion information, obtaining a natural pronation of the selected subject's feet;
   (2) using the motion information, the force information, and the selected subject's physical characteristics, computing a distribution of ground reaction force (GRF) for each of the selected subject's feet, and determining a shear force safety threshold by computing vertical and horizontal components of the GRF for each of the selected subject's feet;
   (3) using the temperature information:
     a. determining a normalized temperature for each of the selected subject's feet; and
     b. determining normalized temperature safety thresholds based upon a correlation of temperature information between similar locations of the selected subject's feet;
   (4) determining a vibratory perception threshold (VPT) indicating the selected subject's feet neuropathy level, and adjusting the temperature safety thresholds depending on the VPT of the selected subject's feet; and
   (5) determining the shear force applied to each of the selected subject's feet based upon the force information and the GRF for each of the selected subject's feet, and modifying the temperature safety thresholds and the shear force safety thresholds depending on the selected subject's activity; and (c) continuously monitoring the motion information generated by the motion processing element, the GRF, and the foot temperature information to determine variations in the foot temperature information and the shear forces; and comparing variations in the foot temperature information and the shear forces to the foot temperature and the shear force safety thresholds, and wherein if any of the safety thresholds are exceeded, generating a warning alert.

19. The system of claim 1, further comprising:

(c) a computer server, in wireless communication with the analysis device, wherein the computer server includes services and resources unavailable in the analysis device; and (d) a foot scanner, wherein the foot scanner may use a combination of 3D laser scans or a pressure plate to obtain foot volume, pronation, pressure and gait patterns, dynamic knee variation and propulsion indices;

and wherein the selected subject's pronation, pressure, gait pattern, and foot temperature distribution is stored in memory accessible to the computer server, and wherein this information is uploaded to the analysis device via a cellular radio interface.

20. The system of claim 19, wherein the uploaded information may be used to replace the following: pronation; natural gait parameters used to build the selected subject's kinematic model; foot pressure pattern; foot temperature distribution, and calibration parameters previously obtained by the analysis device.

21. A system for detecting foot disorders in diabetic subjects, comprising:

(a) first and a second footwear fitted for a selected subject's first and second foot, respectively, wherein both the first and the second footwear includes the following:

(1) a 3-axis accelerometer;

(2) a 3-axis gyroscope;

(3) a 3-axis magnetometer;

(4) a plurality of force sensors placed under the selected subject's feet generating associated and corresponding force vectors, and wherein a shear force is applied to both the first and the second foot, and wherein the force vectors and the shear forces are collectively referred to as force information;

(5) a plurality of temperature sensors measuring skin temperature and generating foot temperature information for both of the selected subject's feet;

(6) haptic actuators placed under the big toe of the selected subject's first and second foot;

(7) a control microprocessor; and (8) a motion processing element, wherein the motion processing element obtains samples of sensor data during selected sampling periods from the accelerometers, the gyroscopes, the magnetometers, the plurality of force sensors and the plurality of temperature sensors, and wherein, at the end of the selected sampling periods, the motion processing element generates motion information including g-force, acceleration information, Euler Angles, Quaternion information and the force information; and (b) an analysis device, wherein the analysis device performs the following:

(1) using the motion information, the force information, and the selected subject's physical characteristics, computes a distribution of ground reaction force (GRF) for each of the selected subject's feet, and determines a shear force safety threshold;

(2) using the temperature information:

a. determines normalized temperature safety thresholds based upon a correlation of temperature information between similar locations of the selected subject's feet;

(3) determines a vibratory perception threshold (VPT) for each of the selected subject's feet, the VPT indicating the selected subject's feet neuropathy level, and adjusts the temperature safety thresholds depending on the VPT of the selected subject's feet; and (4) determines the shear force applied to each of the selected subject's feet based upon the force information and the GRF for each of the selected subject's feet, and modifies the temperature safety thresholds and the shear force safety thresholds depending on the selected subject's activity;

and wherein the analysis device continuously monitors the motion information, the GRF, and the foot temperature information to determine variations in the foot temperature information and the shear forces; and wherein variations in the foot temperature information and the shear forces are compared to the foot temperature and the shear force safety thresholds, and wherein if any of the safety thresholds are exceeded, a warning alert is generated.

* * * * *